(12) United States Patent
Stavrianopoulos et al.

(10) Patent No.: US 7,256,291 B2
(45) Date of Patent: Aug. 14, 2007

(54) LABELING REAGENTS COMPRISING APHENYLIC ANALOGS OF RHODAMINE DYES

(75) Inventors: Jannis G. Stavrianopoulos, Bayshore, NY (US); Elazar Rabbani, New York, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 448 days.

(21) Appl. No.: 10/763,076

(22) Filed: Jan. 22, 2004

(65) Prior Publication Data

US 2004/0254355 A1     Dec. 16, 2004

Related U.S. Application Data

(62) Division of application No. 10/096,075, filed on Mar. 12, 2002, now Pat. No. 7,166,478.

(51) Int. Cl.
| C07D 215/00 | (2006.01) |
| C07D 417/00 | (2006.01) |
| C07H 19/04 | (2006.01) |
| C07H 21/00 | (2006.01) |

(52) U.S. Cl. .................. 546/16; 546/165; 546/270; 546/271.1; 536/23.1; 536/26.6

(58) Field of Classification Search .............. 536/26.6, 536/23.1; 546/16, 165, 270, 271.1
See application file for complete search history.

(56) References Cited

U.S. PATENT DOCUMENTS

| 4,375,972 A | 3/1983 | Forgione et al. |
| 4,683,202 A | 7/1987 | Mullis et al. |
| 4,707,454 A | 11/1987 | Hendrix |
| 4,711,955 A | 12/1987 | Ward et al. |
| 4,868,103 A | 9/1989 | Stavrianopoulos et al. |
| 4,894,325 A | 1/1990 | Engelhardt et al. |
| 4,952,685 A | 8/1990 | Stavrianopoulos et al. |
| 4,978,614 A | 12/1990 | Bronstein |
| 4,994,373 A | 2/1991 | Stavrianopoulos et al. |
| 5,013,831 A | 5/1991 | Stavrianopoulos et al. |
| 5,047,519 A | 9/1991 | Hobbs et al. |
| 5,118,801 A | 6/1992 | Lizardi et al. |
| 5,130,238 A | 7/1992 | Malek et al. |

(Continued)

FOREIGN PATENT DOCUMENTS

EP          0070685          7/1982

(Continued)

OTHER PUBLICATIONS

Ball, et al., "The use of tailed octamer primers for cycle sequencing," *Nucl. Acids. Res.* 26:5225-5227 (1998).

(Continued)

*Primary Examiner*—Jezia Riley
(74) *Attorney, Agent, or Firm*—Natalie Bogdanos, Esq.

(57) ABSTRACT

This invention provides for labeling reagents, labeled targets and processes for preparing labeling reagents. The labeling reagents can take the form of cyanine dyes, xanthene dyes, porphyrin dyes, coumarin dyes or composite dyes. These labeling reagents are useful for labeling probes or targets, including nucleic acids and proteins. These reagents can be usefully applied to protein and nucleic acid probe based assays. They are also applicable to real-time detection processes.

17 Claims, 15 Drawing Sheets

U.S. PATENT DOCUMENTS

| | | | |
|---|---|---|---|
| 5,132,204 A | 7/1992 | Urdea et al. |
| 5,210,015 A | 5/1993 | Gelfand et al. |
| 5,241,060 A | 8/1993 | Engelhardt et al. |
| 5,248,618 A | 9/1993 | Haces |
| 5,268,486 A | 12/1993 | Waggoner et al. |
| 5,270,184 A | 12/1993 | Walker et al. |
| 5,288,609 A | 2/1994 | Engelhardt et al. |
| 5,455,166 A | 10/1995 | Walker et al. |
| 5,455,175 A | 10/1995 | Wittwer et al. |
| 5,462,854 A | 10/1995 | Coassin et al. |
| 5,464,741 A | 11/1995 | Hendrix |
| 5,494,810 A | 2/1996 | Barany et al. |
| 5,554,516 A | 9/1996 | Kacien et al. |
| 5,578,832 A | 11/1996 | Trulson et al. |
| 5,582,984 A | 12/1996 | Bieniarz et al. |
| 5,599,932 A | 2/1997 | Bieniarz et al. |
| 5,627,027 A | 5/1997 | Waggoner et al. |
| 5,646,264 A | 7/1997 | Glazer et al. |
| 5,707,559 A | 1/1998 | Schaap et al. |
| 5,730,849 A | 3/1998 | Hamby et al. |
| 5,849,480 A | 12/1998 | Cros et al. |
| 5,866,336 A | 2/1999 | Nazarenko et al. |
| 5,891,636 A | 4/1999 | Van Gelder et al. |
| 5,945,283 A | 8/1999 | Kwok et al. |
| 5,945,526 A | 8/1999 | Lee et al. |
| 5,948,648 A | 9/1999 | Kahn et al. |
| 5,994,056 A | 11/1999 | Higuchi |
| 6,001,573 A | 12/1999 | Roalent |
| 6,004,286 A | 12/1999 | Bellhouse et al. |
| 6,008,373 A | 12/1999 | Waggoner et al. |
| 6,110,630 A | 8/2000 | Reddy et al. |
| 6,114,350 A | 9/2000 | Randall et al. |
| 6,174,670 B1 | 1/2001 | Wittwer et al. |
| 6,221,581 B1 | 4/2001 | Engelhardt et al. |
| 6,228,578 B1 | 5/2001 | Impraim et al. |
| 6,323,337 B1 | 11/2001 | Singer et al. |
| 6,338,954 B1 | 1/2002 | Gemen |

FOREIGN PATENT DOCUMENTS

| | | | |
|---|---|---|---|
| EP | 0252683 B1 * | 1/1995 |
| EP | 0667393 | 8/1995 |
| EP | 0917039 | 1/2000 |
| EP | 1275737 | 1/2003 |
| EP | 1344835 | 11/2003 |
| WO | WO 9928500 | 11/1998 |

OTHER PUBLICATIONS

Baranov, et al., "A new technique for the characterization of long-range tertiary contacts in large RNA molecules: insertion of a photolabel at a selected position in 16S rRNA within the *Escherichia coli* ribosome," *Nucl. Acids Res.* 25:2266-2273 (1997).

Dale, R.M., et al., "The synthesis and enzymatic polymerization of nucleotide containing mercury: potential tools for nucleic acid sequencing and structural analysis." *Proc. Natl. Acad. Sci. USA* 70:2238-2242 (1973).

Doan, T.L., et al., "Targeted cleavage of polynucleotides by complementary oligonucleotides covalently linked to iron-porphyrins," *Biochemistry* 25:6736-6739 (1986).

Eglinton, G., et al., "A coupling of acetylenic compounds," *Adv. Organic Synthesis* 4:225-328 (1963).

Ernst, et al., "Cyanine dye labeling reagents for sulfhydryl groups," *Cytometry* 10:3-10 (1989).

Fuhrop, J.H., et al., Chapter 19 in "Porphyrins and Metalloporphyrins," ed. Smith, K.M., Elsevier Science, New York (1975).

Kawase, et al., "Studies on nucleic acid interactions. I. Stabilities of mini-duplexes (dG2A4XA4G2-dC2T4YT4C2) and self-complementary d(GGGAAXYTTCCC) containing deoxyinosine and other mismatched bases," *Nucl. Acids. Res.* 14:7727-7736 (1986).

Kuhlmann, K.F., et al., "Synthesis, DNA-binding and biological activity of a double intercalating analog of ethidium bromide," *Nucl. Acids. Res.* 5:2629-2633 (1978).

Larock, "Organomercurials in Organic Synthesis," *Tetrahedron* 38:1713-1754 (1982).

Lee, L.G., et al., "DNA sequencing with dye-labeled terminators and T7 DNA polymerase: effect of dyes and dNTPs on incorporation of dye-terminators and probability analysis of termination fragments," *Nucl. Acids. Res.* 20:2471-2488 (1992).

Liu, H., et al., "PCR amplification using deoxyinosine to replace an entire codon and at ambiguous positions," *Biotechniques* 16:24-26 (1994).

Liu, D., et al., "Stable human immunodeficiency virus type 1 (HIV-1) resistance in transformed CD4 + monocytic cells treated with multitargeting HIV-1 antisense sequences incorporated into U1 snRNA," *J. Virol* 71:4079-4085 (1997).

Loakes, D., et al., "5-Nitroindole as an universal base analogue," *Nucl. Acids Res.* 22:4039-4043 (1994).

Loakes, D., "The applications of universal DNA base analogues," *Nucl. Acids Res.* 29:2437-2447 (2001).

Maulding, D.R., et al., "Chemiluminescence from Reactions of Electrophilic Oxamides with Hydrogen Peroxide and Fluorescent Compounds," *J. Org. Chem.* 33:250-254 (1968).

Moan, J., et al., "Porphyrin photosensitization and phototherapy," *Photochem. Photobio.* 43:681-690 (1986).

Mujumdar, R.B., et al., "Cyanine dye labeling reagents containing isothiocyanate groups," *Cytometry* 10:11-19 (1989).

Mujumdar, R.B., et al., "Cyanine dye labeling reagents: sulfoindocyanine succinimidyl esters," *Bioconjugate Chemistry* 4:105-111 (1993).

Nichols, et al., "A universal nucleoside for use at ambiguous sites in DNA primers," *Nature* 369:492-493 (1994).

Okayama, H., et al., "High efficiency cloning of full length cDNA," *Mol. Cell. Biol.* 2:161 (1982).

Rieke, R.D., "The preparation of highly reactive metals and the development of novel organometallicreagents," *Aldrichimica Acta* 33:52-60 (2000).

Robins, M.J., et al., "Nucleic Acid Related Compounds. 39. Efficient Conversion of 5-Iodo to 5-Alkynyl and Derived 5-Substituted Uracil Bases and Nucleosides," *J. Org. Chem.* 48:1854-1862 (1983).

Schaap, et al., "Chemical and Enzymatic Triggering of 1,2-Dioxetanes. 1:Aryl Esterase-Catalyzed Chemiluminescence from a Naphthyl Acetate-Substituted 1,2-Dioxetane," *Tetrahedron Letters* 28:935-938 (1987).

Schaap, A.P., et al., "Chemical and Enzymatic Triggering of 1,2-Dioxetanes. 3: Alkaline Phosphatase-Catalyzed Chemiluminescence from an Aryl Phosphate-Substituted Dioxetane," *Tetrahedron Letters* 28:1159-1163 (1987).

Selinger, D.W., et al., "RNA expression analysis using a 30 base pair resolution *Excherichia coli* genome array," *Nature Biotech.* 18:1262-1268 (2000).

Shibahara, S., et al., "Site-directed cleavage of RNA," *Nucl. Acids. Res.* 15:4403-4415 (1987).

Southwick, P.L., et al., "Cyanine dye labeling reagents—carboxymethylindocyanine succinimidyl esters," *Cytometry* 11:418-430 (1990).

Talaat, A.M., et al., "Genome-directed primers for selective labeling of bacterial transcripts for DNA microarray analysis," *Nature Biotech.* 18:679-682 (2000).

Tao, et al., "Genomics: Expression Analysis of *Escherichia coli* Growing on Minimal and Rich Media," *J. Bact.* 181:6425-6490 (1999).

Wieringa, J.H., et al., "Adamantylideneadamantane Peroxide. A Stable 1,2 Dioxetane," *Tetrahedron Letters* 2:169-172 (1972).

Zhu, Z., et al., "Directly labeled DNA probes using fluorescent nucleotides with different length linkers," *Nucl. Acids. Res.* 22:3418-3422 (1994).

* cited by examiner

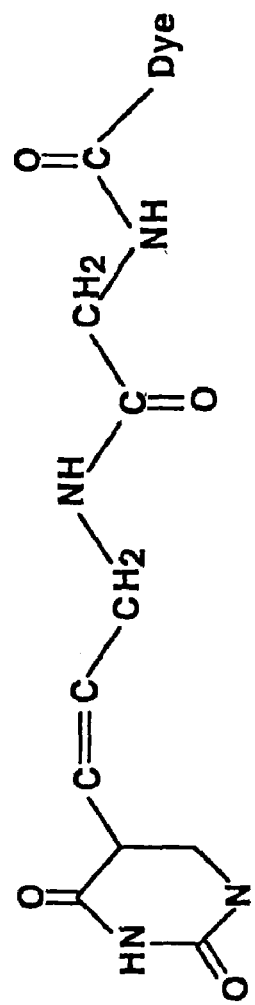
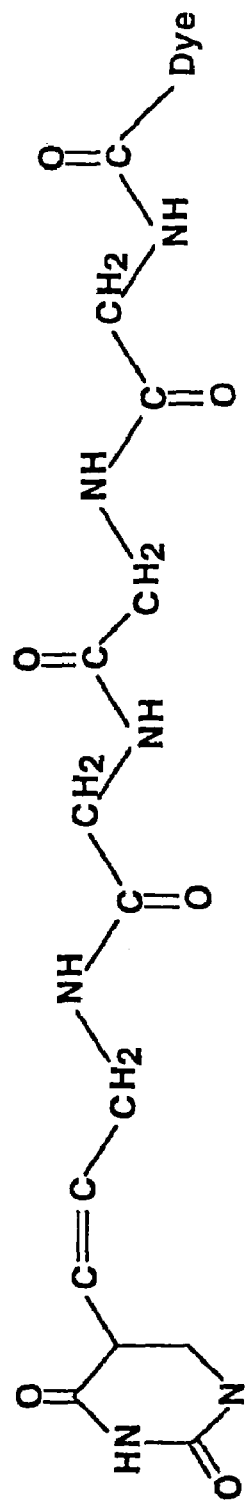
Figure 1

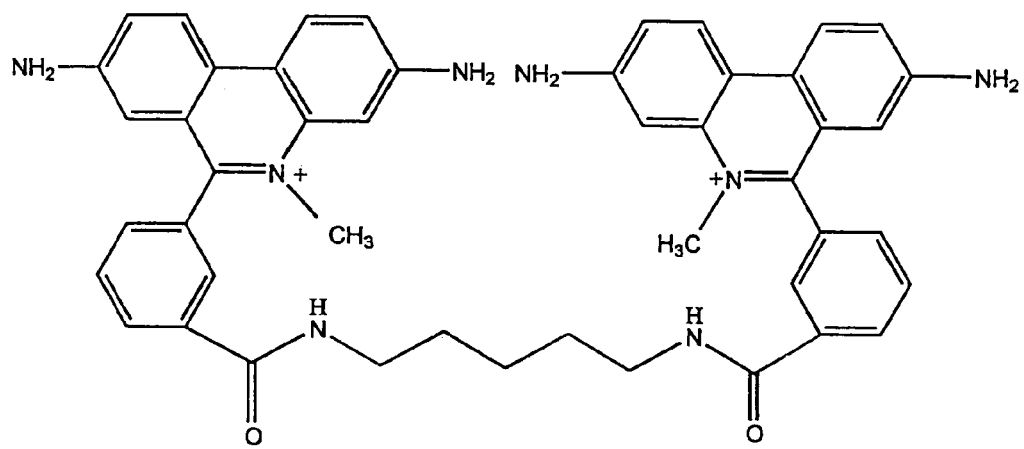
*meta*-EthD
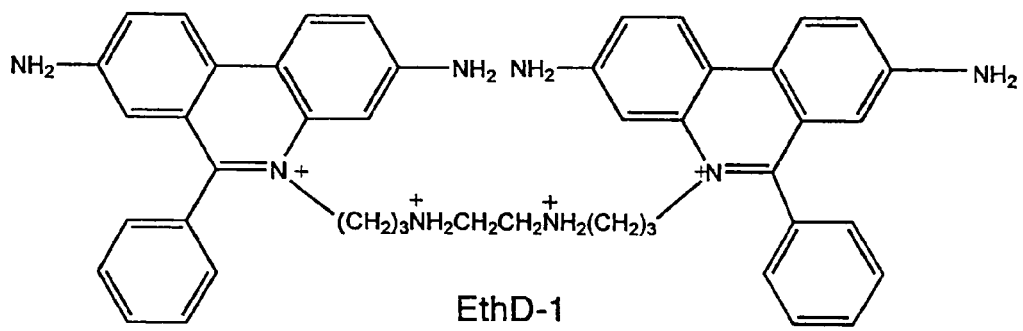
EthD-1
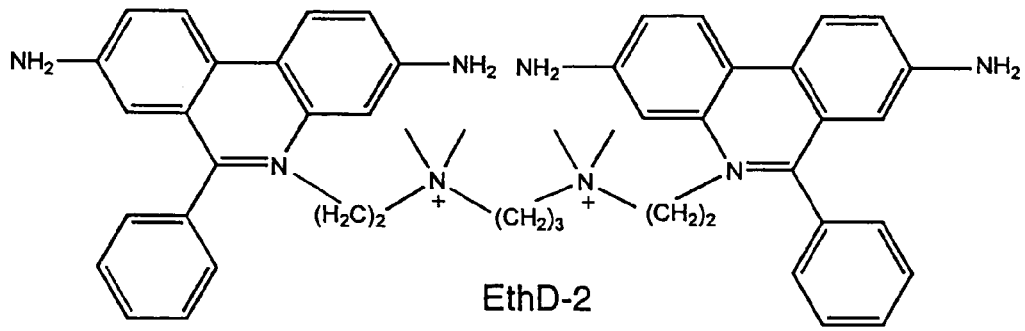
EthD-2
Figure 2

Target Sequence
—GCGACCTGCGAATGCTATGGATCAGGCTAGCCA—
—CGCTGGACGCTTACGATACCTAGTCCGATCGGT—
(A)
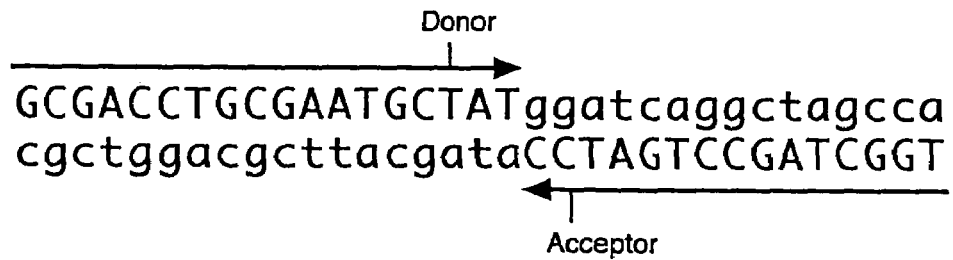
(B)
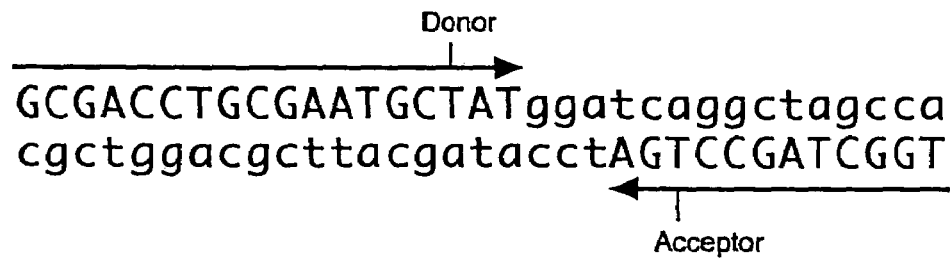
Figure 4

(A) PCR
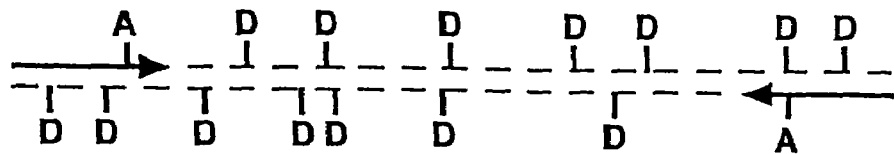
(B) SDA
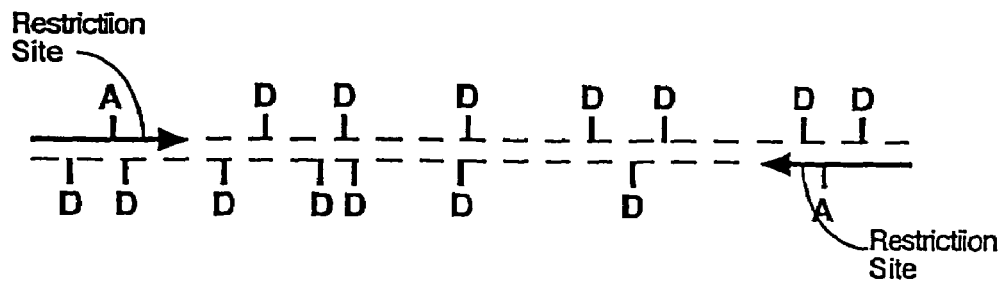
(C) GAP-LCR
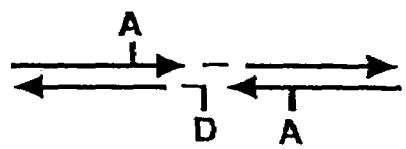
(D) PCR
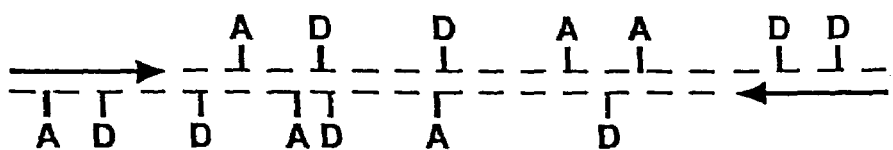
A = Energy Acceptor
D = Energy Donor
Figure 5

Illumination at 472 nM

Illumination at 350 nM

A) Binding of CNAC to poly A tail

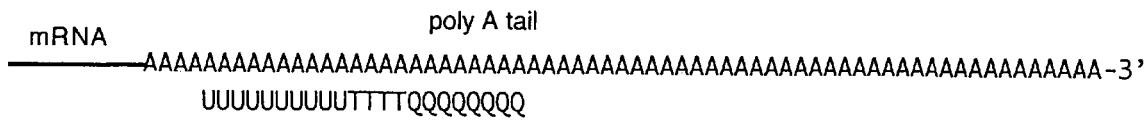

```
mRNA                    poly A tail
————AAAAAAAAAAAAAAAAAAAAAAAAAAAAAAAAAAAAAAAAAAAAAAAAAAAAAAAAAAAAAAA-3'
        UUUUUUUUUUUTTTTQQQQQQQQ
                CNAC
```

U = Uridine (ribonucleotide)
T = Thymidine (deoxyribonucleotide)
Q = Inosine (ribonucleotide)

B) elimination of poly A segment by RNase H

↓ RNase H

```
mRNA
————AAAAAAAAAAAAAA-3'
        UUUUUUUUUUUTTTTQQQQQQQQ
                CNAC
```

C) Incorporation of primer binding site by template dependent extension of analyte ↓ Rerverse Transcriptase

```
mRNA
————AAAAAAAAAAAAAAAAAAACCCCCCCC-3'
        UUUUUUUUUUUTTTTQQQQQQQQ
                CNAC
```

D) Removal of CNAC and binding of primer with promoter sequence

```
mRNA                    GGGGGGGG-promoter-5'
————AAAAAAAAAAAAAAAAAAACCCCCCCC-3'
```

Figure 13

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

```
<220> FEATURE:
<223> OTHER INFORMATION: Description of Combined DNA/RNA Molecule:
      Primer
<220> FEATURE:
<221> NAME/KEY: modified_base
<222> LOCATION: (3)
<223> OTHER INFORMATION: Uridine moiety modified with a non-flourescent
      3-amino xanthene
<220> FEATURE:
<221> NAME/KEY: modified_base
<222> LOCATION: (12)
<223> OTHER INFORMATION: Uridine moiety modified with a non-flourescent
      3-amino xanthene

<400> SEQUENCE: 1
caugatccgg augggaggtg                                                      20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule: Probe
<220> FEATURE:
<221> NAME/KEY: modified_base
<222> LOCATION: (6)
<223> OTHER INFORMATION: Uridine moiety modified with a non-flourescent
      3-amino xanthene
<220> FEATURE:
<221> NAME/KEY: modified_base
<222> LOCATION: (12)
<223> OTHER INFORMATION: Uridine moiety modified with a non-flourescent
      3-amino xanthene
<220> FEATURE:
<221> NAME/KEY: modified_base
<222> LOCATION: (15)
<223> OTHER INFORMATION: Uridine moiety modified with a non-flourescent
      3-amino xanthene

<400> SEQUENCE: 2
gcacauccgg auaguaga                                                        18

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe sequence
<220> FEATURE:
<223> OTHER INFORMATION: Description of Combined DNA/RNA Molecule:
      Synthetic probe sequence
<220> FEATURE:
<221> NAME/KEY: modified_base
<222> LOCATION: (1)
<223> OTHER INFORMATION: Uridine labeled with Texas Red
<220> FEATURE:
<221> NAME/KEY: modified_base
<222> LOCATION: (7)
<223> OTHER INFORMATION: Uridine labeled with Texas Red
<220> FEATURE:
<221> NAME/KEY: modified_base
<222> LOCATION: (17)
<223> OTHER INFORMATION: Uridine labeled with Texas Red
<220> FEATURE:
<221> NAME/KEY: modified_base
<222> LOCATION: (27)
<223> OTHER INFORMATION: Uridine labeled with Texas Red

<400> SEQUENCE: 3
uaatggugag tatcccugcc taactcu                                              27
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      chimeric nucleic acid construct sequence
<220> FEATURE:
<223> OTHER INFORMATION: Description of Combined DNA/RNA Molecule:
      Synthetic chimeric nucleic acid construct sequence
<220> FEATURE:
<221> NAME/KEY: modified_base
<222> LOCATION: (15)..(22)
<223> OTHER INFORMATION: Inosine ribonucleotide

<400> SEQUENCE: 4
uuuuuuuuuu ttttnnnnnn nn                                              22

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5
gcgacctgcg aatgctatgg atcaggctag cca                                  33

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
catgatccgg atgggaggtg                                                 20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
taatggtgag tatccctgcc taactct                                         27

<210> SEQ ID NO 8
<211> LENGTH: 78
<212> TYPE: DNA
<213> ORGANISM: Human immunodeficiency virus

<400> SEQUENCE: 8
catgatccgg atgggaggtg ggtctgaaac gataatggtg agtatccctg cctaactcta     60
ttcactatcc ggatgtgc                                                   78

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
```

```
gcacatccgg atagtgaata ga                                          22

<210> SEQ ID NO 10
<211> LENGTH: 65
<212> TYPE: RNA
<213> ORGANISM: Artificial Sequence
<220> FEATURE:
<223> OTHER INFORMATION: Description of Artificial Sequence: Primer

<400> SEQUENCE: 10
aaaaaaaaaa aaaaaaaaaa aaaaaaaaaa aaaaaaaaaa aaaaaaaaaa aaaaaaaaaa    60
aaaaa                                                               65

<210> SEQ ID NO 11
<211> LENGTH: 14
<212> TYPE: RNA
<213> ORGANISM: Artificial Sequence
<220> FEATURE:
<223> OTHER INFORMATION: Description of Artificial Sequence: Primer

<400> SEQUENCE: 11
aaaaaaaaaa aaaa                                                     14

<210> SEQ ID NO 12
<211> LENGTH: 26
<212> TYPE: RNA
<213> ORGANISM: Artificial Sequence
<220> FEATURE:
<223> OTHER INFORMATION: Description of Artificial Sequence: Primer

<400> SEQUENCE: 12
aaaaaaaaaa aaaaaaaacc ccccc                                        26
```

LABELING REAGENTS COMPRISING APHENYLIC ANALOGS OF RHODAMINE DYES

This is a divisional of U.S. patent application Ser. No. 10/096,075, filed on Mar. 12, 2002 now U.S. Pat. No. 7,166,478.

FIELD OF THE INVENTION

This invention relates to the field of labeling chemistry including labeling reagents, processes for target labeling, labeled targets, processes for preparing labeling reagents, and the like. This invention also relates to the use of such compositions and processes in other processes for nucleic acid and enzymatic activity determinations and analyses.

All patents, patent applications, patent publications, scientific articles and the like, cited or identified in this application are hereby incorporated by reference in their entirety in order to describe more fully the state of the art to which the present invention pertains.

CROSS-REFERENCE TO RELATED APPLICATIONS

This application is related to concurrently filed U.S. patent application Ser. No. 10/096,076, filed Mar. 12, 2002, Rabbani et al., that application being titled "Real-Time Nucleic Acid Detection Processes and Compositions." The contents of the aforementioned Ser. No. 10/096,076 are hereby incorporated by reference in their entirety.

BACKGROUND OF THE INVENTION

For purposes of organization, this background has been divided into seven parts as follows:
(1) Reactive Groups of Labeling Reagents
(2) Llnker Arms for Connecting Labels to Targets
(3) Porphyrin Fluorescent Dyes as Labels
(4) Alterations in Fluorescent Properties
(5) Fluorescent Intercalators
(6) Chemiluminescence
(6) Real Time Detection through Fluorescence
(7) Primer Binding Sequences in Analytes (1) Reactive Groups of Labeling Reagents The use of non-radioactive labels in biochemistry and molecular biology has grown exponentially in recent years. Among the various compounds used as non-radioactive labels, aromatic dyes that produce fluorescent or luminescent signal are especially useful. Notable examples of such compounds include fluorescein, rhodamine, coumarin and cyanine dyes such as Cy3 and Cy5. Composite dyes have also been synthesized by fusing two different dyes together (Lee et al., (1992) Nucl. Acids Res. 20; 2471-2488; Lee et al., U.S. Pat. No. 5,945,526 and Waggoner et al., in U.S. Pat. No. 6,008,373, all of which are hereby incorporated by reference).

Non-radioactive labeling methods were initially developed to attach signal-generating groups onto proteins. This was achieved by modifying labels with chemical groups such that they would be capable of reacting with the amine, thiol, and hydroxyl groups that are naturally present in proteins. Examples of reactive groups that were used for this purpose included activated esters such as N-hydroxysuccinimide esters, isothiocyanates and other compounds. Consequently, when it became desirable to label nucleotides and nucleic acids by non-radioactive means, methods were developed to convert nucleotides and polynucleotides into a form that made them functionally similar to proteins. For instance, U.S. Pat. No. 4,711,955 (incorporated by reference) disclosed the addition of amines to the 8-position of a purine, the 5-position of a pyrimidine and the 7-position of a deazapurine. The same methods that could add a label to the amine group of a protein could now be applied towards these modified nucleotides.

Among the compounds used as fluorescent labels, the cyanine-based dyes have become widely used since they have high extinction coefficients and narrow emission bands. Furthermore, modifications can be made in their structure that can alter the particular wavelengths where these compounds will absorb and fluoresce light. The cyanine dyes have the general structure comprising two indolenine based rings connected by a series of conjugated double bonds. The dyes are classified by the number (n) of central double bonds connecting the two ring structures; monocarbocyanine or trimethinecarbocyanine when n=1; dicarbocyanine or pentamethinecarbocyanine when n=2; and tricarbocyanine or heptamethinecarbocyanine when n=3. The spectral characteristics of the cyanine dyes have been observed to follow specific empirical rules. For example, each additional conjugated double bond between the rings will raise the absorption and emission maximum about 100 nm. Thus, when a compound with n=1 has a maximum absorption of approximately 550 nm, equivalent compounds with n=2 and n=3 will have maximum absorptions of 650 nm and 750 nm respectively. Addition of aromatic groups to the sides of the molecules can shift the absorption by 15 nm to a longer wavelength. The groups comprising the indolenine ring can also contribute to the absorption and emission characteristics. Using the values obtained with gem-dimethyl group as a reference point, oxygen substituted in the ring for the gem-dimethyl group decreases the absorption and emission maxima by approximately 50 nm. In contrast, substitution of sulfur increases the absorption and emission maxima by about 25 nm. R groups on the aromatic rings such as alkyl, alkyl-sulfonate and alkyl-carboxylate have little effect on the absorption and emission maxima of the cyanine dyes (U.S. Pat. No. 6,110, 630).

Cyanine dyes synthesized with arms containing functional groups have been prepared with iodoacetamide, isothiocyanate and succinimidyl esters that react with sulfhydryl groups on proteins (Ernst, et al.,(1989), Cytometry 10, 3-10; Mujumdar, et al., (1989), Cytometry 10, 11-19; Southwick, et al., (1990) Cytometry 11, 4187-430). A new series of modified dyes were prepared which contained a sulfonate group on the phenyl portion of the indolenine ring. (Mujumdar et al., (1993) Bioconjugate Chemistry 4; 105-111 hereby incorporated by reference) that increased the water solubility of the dyes. These dyes were activated by treatment with disuccinimidyl carbonate to form succinimidyl esters that were then used to label proteins by substitution at the amine groups. Other activating groups have since been placed on the cyanine dyes. In U.S. Pat. Nos. 5,627,027 and 5,268,486 (incorporated by reference), cyanine dyes were prepared which comprise isothiocyanate, isocyanate, monochlorotriazine, dichlorotriazine, mono or di-halogen substituted pyridine, mono or di-halogen substituted diazine, aziridine, sulfonyl halide, acid halide, hydroxy-succinimide ester, hydroxy-sulfosuccinimide ester, imido esters, glyoxal groups and aldehydes and other groups, all of which can form a covalent bond with an amine, thiol or hydroxyl group on a target molecule.

In U.S. Pat. No. 6,110,630 (incorporated by reference), cyanine dyes were prepared with a series of reactive groups derived from N-hydroxynaphthalimide. These groups included hydroxysuccinimide, para-nitrophenol, N-hydroxyphtalimide and N-hydroxynaphtalimide all of which can react with nucleotides modified with primary amines. The same chemical reactions that have been described above have also been used in U.S. Pat. No. 6,114,350 (incorporated by reference) but with the constituents reversed. In this disclosure, the cyanine dyes were modified with amine, sulfhydryl or hydroxyl groups and the target molecules were modified to comprise the appropriate reactive groups.

Cyanine dyes containing arms that comprise reactive functional groups have been prepared by the general scheme in which the entire heterocyclic compound comprising the two indolenine structures and the intervening unsaturated chain was synthesized first; the terminal reactive groups or any other functionality necessary to link the dyes to proteins or nucleic acids were then added after the completion of the whole dimeric dye unit.

(2) Linker Arms for Connecting Labels to Targets

Labeled nucleotides have been used for the synthesis of DNA and RNA probes in many enzymatic methods including terminal transferase labeling, nick translation, random priming, reverse transcription, RNA transcription and primer extension. Labeled phosphoramidite versions of these nucleotides have also been used with automated synthesizers to prepare labeled oligonucleotides. The resulting labeled probes are widely used in such standard procedures as northern blotting, Southern blotting, in situ hybridization, RNAse protection assays, DNA sequencing reactions, DNA and RNA microarray analysis and chromosome painting.

There is an extensive literature on chemical modification of nucleic acids by means of which a signal moiety is directly or indirectly attached to a nucleic acid. Primary concerns of this art have been with regard to which site in a nucleic acid is used for attachment i.e. sugar, base or phosphate analogues and whether these sites are disruptive or non-disruptive (see for instance the disclosures of U.S. Pat. Nos. 4,711,955 and 5,241,060; both patents incorporated by reference), the chemistry at the site of attachment that allows linkage to a reactive group or signaling moiety a spacer group usually consisting of a single aromatic group (U.S. Pat. Nos. 4,952,685 and 5,013,831, both hereby incorporated by reference) or a carbon/carbon aliphatic chain to provide distance between the nucleic acid and a reactive group or signaling moiety and a reactive group at the end of the spacer such as an OH, NH, SH or some other group that can allow coupling to a signaling moiety and the nature of the signaling moiety.

Although the foregoing have all been descriptions of the various aspects that are concerned with the synthesis of modified nucleotides and polynucleotides, they have also been shown to be significant factors with regard to the properties of the resultant nucleotides and polynucleotides. Indeed, there have been numerous demonstrations that the modified nucleotides described in the present art have shortcomings compared to unmodified nucleotides.

For instance, these factors can have major impact on the ability of these modified nucleotides to be incorporated by polymerases. A consequence of this is that when using a modified base as the sole source of that particular nucleotide, there may be a loss in the amount of nucleic acid synthesis compared to a reaction with unmodified nucleotides. As a result of this, modified nucleotides are usually employed as part of a mixture of modified and unmodified versions of a given nucleotide. Although this restores synthesis to levels comparable to reactions without any modified nucleotides, a bias is often seen against the use of the modified version of the nucleotide. As such, the final proportion of modified/ unmodified nucleotide may be much lower than the ratio of the reagents. Users then have a choice of either using nucleic acids that are minimally labeled or of decreased yields. When comparable modified nucleotides are used that only comprise a linker arm attached to a base (such as allylamine dUTP) difficulties with incorporation are seldom seen. As such, the foregoing problem is likely to be due to the interactions of the label with either the polymerase or the active site where synthesis is taking place.

Difficulties in the use of polymerases can be bypassed by the use of oligonucleotide synthesizers where an ordered chemical joining of phosphoramidite derivatives of nucleotides can be used to produce labeled nucleic acids of interest. However, the presence of signal agents on modified nucleotides can even be problematic in this system. For instance, a phosphoramidite of a modified nucleotide may display a loss of coupling efficiency as the chain is extended. Although this may be problematic in itself, multiple and especially successive use of modified nucleotides in a sequence for a synthetic oligonucleotide can result in a drastic cumulative loss of product. Additionally, chemical synthesis is in itself not always an appropriate solution. There may be circumstances where labeled nucleic acids need to be of larger lengths than is practical for a synthesizer. Also, an intrinsic part of synthetic approaches is a necessity for a discrete sequence for the nucleic acid. For many purposes, a pool or library of nucleic acids would require an impractically large number of different species for synthetic approaches.

An example of a method to increase the yield of labeled oligonucleotides or polynucleotide is to use a non-interfering group such as an allylamine modified analogue during synthesis by either a polymerase or an oligonucleotide synthesizer. Labeling is then carried out post-synthetically by attachment of the desired group through the chemically reactive allylamine moieties. However, in this case, although incorporation or coupling efficiency may be restored, there may still be problems of the coupling efficiencies of attachment of the desired group to the allylamine. For instance, coupling of labels to allylamine moieties in a nucleic acid is dramatically less efficient for double-stranded DNA compared to single-stranded targets. In addition to potential yield problems, the functionality of the modification may be affected by how it is attached to a base. For instance if a hapten is attached to a base, the nature of the arm separating the hapten from the base may affect its accessibility to a potential binding partner. When a signal generating moiety is attached through a base, the nature of the arm may also affect interactions between the signal generating moiety and the nucleotide and polynucleotide.

Attempts to limit these deleterious interactions have been carried out in several ways. For instance, attachment of the arm to the base has been carried out with either a double bond alkene group (U.S. Pat. No. 4,711,955) or a triple bond alkyne group (U.S. Pat. No. 5,047,519) thereby inducing a directionality of the linker away from the nucleotide or polynucleotide. However, this approach is of limited utility since this rigidity is limited to only the vicinity of the attachment of the linker to the base. In addition, attempts at limiting interactions have been carried out by having the arm displace the active or signal group away from the nucleotide or polynucleotide by lengthening the spacer group. For instance, a commercially available modified nucleotide included a seven carbon aliphatic chain (Cat. No. 42724, ENZO Biochem, Inc. New York, N.Y.) between the base and a biotin moiety used for signal generation. This product was further improved by the substitution of linkers with 11 or even 16 carbon lengths (Cat. Nos. 42722 and 42723, also available from ENZO Biochem, Inc. New York, N.Y.). A comparison was also carried out using different length linker arms and a cyanine dye labeled nucleotide (Zhu et al., 1994 Nucl. Acid Res. 22; 3418-3422). A direct improvement in efficiency was noted as the length was increased from 10 to 17 and from 17 to 24. However, even with the longest linker, it could be seen that there was incomplete compensation for the presence of the fluorescent marker in terms of efficiency. This may be a result of the fact that due to the flexibility of the aliphatic carbon chain used for this spacer segment, the reporter groups will seldom be found in a conformation where they are completely extended away from the nucleotide itself. Thus, although this approach changed the length of the linker, it was not a change in the flexible nature of the spacer.

In an attempt to circumvent this problem, in U.S. Pat. No. 5,948,648, Khan et al. have disclosed the use of multiple alkyne or aromatic groups connecting a marker to a nucleotide. However, this method employs highly non-polar groups in the linker that may induce interaction between the linker and the marker, thereby limiting its effectiveness by decreasing coupling efficiencies or by increasing non-specific binding by labeled compounds that include these groups. In addition, these groups may decrease the water solubility of either the labeled compound or various intermediates used to make the labeled compound.

The continued difficulties in using activated or labeled nucleotides which have incorporated the foregoing features demonstrates that there are still deleterious interactions occurring between the base, oligonucleotide or polynucleotide and the moiety at the end of the arm in methods of the previous art. Although the foregoing has been described with respect to attachment to nucleic acids, these problems are shared with other groups for which it may be useful to attach a marker or label.

(3) Porphyrin Fluorescent Dyes as Labels

Assays that employ fluorescently labeled probes depend upon illumination at one particular wavelength and detection of the emission at another wavelength (the Stokes shift). There exists an extensive literature on the variety of compounds that have various excitation/emission spectral characteristics suitable for such assays. When fluorescent compounds are used for comparative expression analysis, the ability to carry out signal detection simultaneously for each label depends upon how marked is the difference between the labels. Thus, fluorophores such as Cy 3 and Cy 5 are commonly used in expression analysis since they have emission peaks at 570 and 667 respectively. One class of compounds that has not been effectively exploited for this analysis are the porphyrins.

The ability of porphyrins to absorb light energy and efficiently release it has been used in a number of other systems. For example, light induced cleavage of nucleic acids can be carried out by a number of metallo-porphyrins that are either free in solution or attached to a sequence specific oligonucleotide (Doan et al., (1986) Biochemistry 26; 6736-6739). One application of this system has been the targeting and killing of cancer cells through light induced DNA damage after absorption of metallo-phorphyrins (Moan et al., (1986) Photochemistry and Photobiology 43; 681-690). Another example of the high energetic ability of metallo-phorphyrins can be seen with their use as catalytic agents (Forgione et al., U.S. Pat. No. 4,375,972) for non-enzymatic chemiluminescence. Furthermore, there are cases where phorphyrins have been used as labeling reagents, for example Roelant et al in U.S. Pat. No. 6,001,573 and Hendrix in U.S. Pat. No. 5,464,741 (hereby incorporated by reference) where Pd octaethylporphyrins were converted to the isothiocyanate and used as labeling reagents particularly for use in immunoassays. However, in these cases metallic phorphyrins were exclusively used.

The drawback of the use of metallo-phorphyrins is that the destructive abilities of these compounds are counterproductive when used in array analysis or other assay systems which require the maintenance of the integrity of the nucleic acid strands of analytes or probes. Therefore, it would be highly advantageous to be able to utilize porphyrins for their fluorescent and chemiluminescent properties while eliminating their nucleic acid destructive properties.

(4) Alterations in Fluorescent Properties

In previous art, it has been shown that the addition of phenylacetylene groups to anthracene increases the emission maxima 72 nm. (Maulding and Roberts, 1968 J Org Chem ). Furthermore, the Stokes shift, the difference between the absorption and emission maxima, was also increased by the addition of the phenyl acetylene group to the anthracene dye. Specifically the difference of 6 nm was increased to 31 nm following the addition of two phenyl acetylene groups. When the phenyl acetylene group was added to naphthacene the difference between the absorption and emission maxima increased from 7 nm to 32 nm. Furthermore, the quantum yields of anthracene and naphtacene was significantly increased by the addition of the phenyl acetylene groups to them.

The application of this effect was limited to these compounds because the chemistries and reactions used for the addition of these substituents required ketone or aldehyde groups. Also, addition of unsaturated groups to dyes has the undesired effect of potentially decreasing their solubility in aqueous solutions. In addition, the modified anthracene dyes described by Maulding and Roberts lacked any reactive groups that could be used for attachment.

(5) Fluorescent Intercalators

Intercalating dyes have been used for the detection and visualization of DNA in many techniques including the detection of DNA in electrophoresis gels, in situ hybridization, flow cytometry and real time detection of amplification. An intercalating dye with a long history of popular usage is ethidium bromide. Ethidium bromide has the useful properties of high affinity for nucleic acids and an increased fluorescence after binding. This enhancement of fluorescence takes place with both single-stranded and double-stranded nucleic acids with the double-stranded DNA showing a much more marked effect, generally around thirty-fold. Other dyes which exhibit increased fluorescence signal upon binding to nucleic acid have been developed in recent years including such compounds as acridine orange, SYBR Green and Picogreen. There is continually a need, however, for increased signal generation after the binding or intercalation with nucleic acids especially for the use in techniques, such as real time amplification.

(6) Chemiluminescence

The use of chemiluminescent reagents for signal detection has gained wider use in recent years. There are several different classes of compounds that can produce luminescent signals including 1,2-dioxetanes and luminols. 1,2-Dioxetanes are four-membered rings which contain two adjacent oxygens. Some forms of these compounds are very unstable and emit light as they decompose. On the other hand, the presence of an adamantyl group can lead to a highly stable form with a half-life of several years (Wieringa et al. (1972) Tetrahedron Letters 169-172 incorporated by reference). Use can be made of this property by using a stable form of a 1,2-dioxetane as a substrate in an enzyme linked assay where the presence of the enzyme will transform the substrate into an unstable form thereby using chemiluminescence for signal generation. Enzymatic induction of a chemiluminescent signal has been described where an adamantyl dioxetane derivative was synthesized with an additional group that was a substrate for enzymatic cleavage (U.S. Pat. No. 5,707,559, Schaap et al. (1987) Tetrahedron Letters, 28; 935-938; Schaap et al. (1987) Tetrahedron Letters, 28; 1159-1163, all of which are incorporated by reference). In the presence of the appropriate enzyme, cleavage would take place and an unstable compound would be formed that emitted light as it decomposes.

A common design of dioxetane derivatives for this method is attachment of an aryl group that has hydroxyl substituents which contain protecting groups. The removal of the protecting group by the appropriate enzyme results in a negatively charged oxygen. This intermediate is unstable and leads to the decomposition of the compound and the emission of light. Various 1,2-dioxetane derivatives have been developed that can be activated by different enzymes depending upon the nature of the protecting group. Enzymes that have been described as potentially useful for this purpose have included alkaline phosphatase, galactosidase, glucosidase, esterase, trypsin, lipase, and phospholipase among others (for instance, see U.S. Pat. No. 4,978,614, incorporated herein by reference).

Variations of this basic method have also been disclosed. For example, Urdea has disclosed (U.S. Pat. No. 5,132,204, incorporated by reference) stable 1,2-dioxetanes derivatives which require the activity of two enzymes in order to produce a signal. Haces has disclosed a method where the decomposition of the 1,2-dioxetane is triggered by an enzymatic or chemical reaction which releases a terminal nucleophile (U.S. Pat. No. 5,248,618 incorporated by reference). This can now undergo an intramolecular substitution reaction, thereby liberating a phenoxy group which triggers the decomposition of the 1,2-dioxetane. The chain where the intramolecular reaction takes place is made up of single bonds thus allowing complete rotational freedom around all the bonds and relying on a random interaction between the groups participating in the intramolecular reaction.

Despite improvements within the field of chemiluminescent signaling there still exists the need for new substrates and reagents. Many of the substrates that are currently available produce a high level of background due to enzyme independent triggering of the decomposition of the substrate and release of chemiluminescent signal. Therefore, a new type of 1,2-dioxetane which is more stable in the absence of an enzyme would be a desirable reagent.

(7) Real Time Detection through Fluorescence

Amplification of nucleic acids from clinical samples has become a widely used technique. The first methodology for this process, the Polymerase Chain Reaction (PCR), was described by Mullis et al. in U.S. Pat. No. 4,683,202 hereby incorporated by reference. Since that time, other methodologies such as Ligation Chain Reaction (LCR) (U.S. Pat. No. 5,494,810), GAP-LCR (U.S. Pat. No. 6,004,286), Nucleic Acid Sequence Based Amplification (NASBA) (U.S. Pat. No. 5,130,238), Strand Displacement Amplification (SDA) (U.S. Pat. Nos. 5,270,184 and 5,455,166) and Loop Mediated Amplification (U.S. patent application Ser. No. 09/104,067; European Patent Application Publication No. EP 0 971 039 A) have been described, all of which are incorporated by reference. Detection of an amplified product derived from the appropriate target has been carried out in number of ways. In the initial method described by Mullis et al., gel analysis was used to detect the presence of a discrete nucleic acid species. Identification of this species as being indicative of the presence of the intended target was determined by size assessment and the use of negative controls lacking the target sequence. The placement of the primers used for amplification dictated a specific size for the product from appropriate target sequence. Spurious amplification products made from non-target sequences were unlikely to have the same size product as the target derived sequence. Alternatively, more elaborate methods have been used to examine the particular nature of the sequences that are present in the amplification product. For instance, restriction enzyme digestion has been used to determine the presence, absence or spatial location of specific sequences. The presence of the appropriate sequences has also been established by hybridization experiments. In this method, the amplification product can be used as either the target or as a probe.

The foregoing detection methods have historically been used after the amplification reaction was completed. More recently, methods have been described for measuring the extent of synthesis during the course of amplification, i.e. "real-time" detection. For instance, in the simplest system, an intercalating agent is present during the amplification reaction (Higuchi in U.S. Pat. No. 5,994,056 and Wittwer et al., U.S. Pat. No. 6,174,670; both of which are hereby incorporated by reference). This method takes advantage of an enhancement of fluorescence exhibited by the binding of an intercalator to double-stranded nucleic acids. Measurement of the amount of fluorescence can take place post-synthetically in a fluorometer after the reaction is over, or real time measurements can be carried out during the course of the reaction by using a special PCR cycler machine that is equipped with a fluorescence detection system and uses capillary tubes for the reactions (U.S. Pat. Nos. 5,455,175 and 6,174,670 hereby incorporated by reference). As the amount of double-stranded material rises during the course of amplification, the amount of signal also increases. The sensitivity of this system depends upon a sufficient amount of double-stranded nucleic acid being produced that generates a signal that is distinguishable from the fluorescence of a) unbound intercalator and b) intercalator molecules bound to single-stranded primers in the reaction mix. Specificity is derived from the nature of the amplification reaction itself or by looking at a Tm profile of the reaction products. Although the initial work was done with Ethidium Bromide, SYBR Green™ is more commonly used at the present time. A variation of this system has been described by Singer and Haugland in U.S. Pat. No. 6,323,337 B1 (incorporated by reference), where the primers used in PCR reactions were modified with quenchers thereby reducing signal generation of a fluorecent intercalator that was bound to a primer dimer molecule. Signal generation from target derived amplicons could still take place since amplicons derived from target sequences comprised intercalators bound to segments that were sufficiently distant from the quenchers.

Another method of analysis that depends upon incorporation has been described by Nazarenko (U.S. Pat. No. 5,866,336; incorporated by reference). In this system, signal generation is dependent upon the incorporation of primers into double-stranded amplification products. The primers are designed such that they have extra sequences added onto their 5' ends. In the absence of amplification, stem-loop structures are formed through intramolecular hybridization that consequently bring a quencher into proximity with an energy donor thereby preventing fluorescence. However, when a primer becomes incorporated into double-stranded amplicons, the quencher and donor become physically separated and the donor is now able to produce a fluorescent signal. The specificity of this system depends upon the specificity of the amplification reaction itself. Since the stem-loop sequences are derived from extra sequences, the Tm profile of signal generation is the same whether the amplicons were derived from the appropriate target molecules or from non-target sequences.

In addition to incorporation based assays, probe based systems have also been used for real-time analysis. For instance, a dual probe system can be used in a homogeneous assay to detect the presence of appropriate target sequences. In this method, one probe comprises an energy donor and the other probe comprises an energy acceptor (European Patent Application Publication No. 0 070 685 by Michael Heller, published Jan. 26, 1983). Thus, when the target sequence is present, the two probes can bind to adjacent sequences and allow energy transfer to take place. In the absence of target sequences, the probes remain unbound and no energy transfer takes place. Even if by chance, there are non-target sequences in a sample that are sufficiently homologous that binding of one or both probes takes place, no signal is generated since energy transfer would require that both probes bind and that they be in a particular proximity to each other. Advantage of this system has been taken by Wittwer et al., in U.S. Pat. No. 6,174,670 (incorporated by reference) for real time detection of PCR amplification using the capillary tube equipped PCR machine described previously. The primer annealing step during each individual cycle can also allow the simultaneous binding of each probe to target sequences providing an assessment of the presence and amount of the target sequences. In a further refinement of this method, one of the primers comprises an energy transfer element and a single energy transfer probe is used. Labeled probes have also been used in conjunction with fluorescent intercalators to allow the specificity of the probe methodology to be combined with the enhancement of fluorescence derived from binding to nucleic acids. This was first described in U.S. Pat. No. 4,868,103 and later applied to amplification reactions in PCT Int. Appl. WO 99/28500 (both documents incorporated by reference).

Probes have also been used that comprise an energy donor and an energy acceptor in the same nucleic acid. In these assays, the energy acceptor "quenches" fluorescent energy emission in the absence of appropriate complementary targets. In one system described by Lizardi et al. in U.S. Pat. No. 5,118,801, "molecular beacons" are used where the energy donor and the quencher are kept in proximity by secondary structures with internal base pairing. When the target sequences are present, complementary sequences in the Molecular Beacons allow hybridization events that destroy this secondary structure thereby allowing energy emission. In another system that has been termed Taqman, use is made of the double-stranded selectivity of the exonuclease activity of Taq polymerase (Gelfand et al., U.S. Pat. No. 5,210,015). When target molecules are present, hybridization of the probe to complementary sequences converts the single-stranded probe into a substrate for the exonuclease. Degradation of the probe separates the donor from the quencher thereby releasing light.

(8) Primer Binding Sequences in Analytes

One of the characteristics of eucaryotic mRNA is the presence of poly A tails at their 3' ends. This particular feature has provided a major advantage in working with mRNA since the poly A segment can be used as a universal primer binding site for synthesis of cDNA copies of any eucaryotic mRNA. However, this has also led to a certain bias in RNA studies, since the 3' ends of mRNA are easily obtained and thoroughly studied but the 5' ends lack such consensus sequences. Thus, a large number of systems have been described whose major purpose has been to generate clones that have complete representation of the original 5' end sequences. This has also been carried over in array analysis for comparative transcription studies. Since substantially all systems used for this purpose are initiated by oligo T priming at the 3' end of mRNA, sequences downstream are dependent upon the continuation of synthesis away from the 3' starting point. However, it is well known that there is an attenuation effect of polymerization as polymerases frequently fall off of templates after synthesis of a particular number of bases. Another effect is generated by the presence of RNase H that is a component of most reverse transcriptases. Paused DNA strands may allow digestion of the RNA near the 3' end of the DNA thereby separating the uncopied portion of the RNA template from the growing DNA strand. This effect may also occur randomly during the course of cDNA synthesis. As such, representation of sequences is inversely proportional to their distance from the 3' poly A primer site.

Although prior art has capitalized extensively on poly A segments of RNA, it should be recognized that poly A mRNA represents only a portion of nucleic acids in biological systems. Another constraint in prior art is that the use of poly A tails is only available in eucaryotic mRNA. Two areas of especial interest are unable to enjoy this benefit. One area is bacterial mRNA since they intrinsically lack poly A additions. The second are is heterologous RNA in eucaryotic systems. For any particular eucaryotic gene, there is a considerable amount of genetic information that is present in heterologous RNA that is lost by the use of polyadenylated mature forms of transcripts that comprise only exon information.

The lack of primer consensus sequence in these systems has necessitated the use of alternatives to oligo T priming. In prior art, bacterial expression studies have been carried out by random priming with octamers (Sellinger et al., 2000 Nature Biotechnology 18; 1262-1268), a selected set of 37 7-mers and 8-mers (Talaat et al., 2000 Nature Biotechnology 18; 679-682) and a set of 4,290 gene specific primers (Tao et al., 1999 J. Bact. 181; 6425-6490). The use of large sets of primers as represented by random primers and set of gene specific primers requires high amounts of primers to drive the reaction and should exhibit poor kinetics due to the sequence complexity of the primers and targets. I.e. for any given sequence in an analyte, there is only a very minute portion of the primers that are complementary to that sequence. Large sets of random primers also have the capacity to use each other as primers and templates thereby generating nonsense nucleic acids and decreasing the effective amounts of primers available. Attempts to improve the kinetics of priming by increasing the amounts of random oligonucleotides is very limited. First off, there are physical constraints in the amount of oligonucleotides that are soluble in a reaction mixture. Secondly, increases in the amount of primers is self-limiting since increased primer concentrations results in increased self-priming, thereby generating more nonsense sequences and absorption of reagents that would otherwise be used for analyte dependent synthesis. Lower concentrations can theoretically be used by decreasing the complexity (i.e. sequence length) of the primers, but restraints are then imposed upon the stability of hybrid formation. On the other hand, the discrete sub-set of 7-mers and 8-mers described above requires knowledge of the complete genome of the intended target organism. As such, these will only be used with completely sequenced organisms, and a unique set has to be individually developed for each target organism thus limiting its application. Consensus sequences can be enzymatically added by RNA ligation or poly A polymerase but both of these are slow inefficient processes. Thus there exists a need for methods and compositions that can efficiently provide stable priming of a large number of non-polyadenylated templates of variable or even unknown sequence while maintaining a low level of complexity.

Methods have also been described for the introduction of sequences into analytes for the purpose of amplification. For instance, oligonucleotides have also been described that comprise a segment complementary to a target sequence and a segment comprising a promoter sequence where the target is either a selected discrete sequence or a natural poly A sequence (U.S. Pat. Nos. 5,554,516 and 6,338,954 (both patents incorporated by reference)). After hybridization to a target mRNA, RNAse H is used to cleave a segment of the analyte hybridized to the complementary segment and then extend the 3' end of the analyte using the promoter segment as a template. Since the oligonucletotide that is used for these methods has a homogeneous nature, this particular method relies upon the extension reaction being initiated before the endonuclease reaction completes digestion of the complementary segment of the analyte.

SUMMARY OF THE INVENTION

The present invention provides a labeling reagent for labeling a target, the labeling reagent comprising a marker moiety M and a reactive group R

M-R wherein the marker moiety M and the reactive group R are covalently linked together, the M comprising at least one moiety that comprises a ligand, a dye, or both a ligand and a dye; and the reactive group R being capable of forming a carbon-carbon linkage with the target.

The present invention also provides a process for labeling a target, the process comprising the steps of (a) providing: (i) the target; (ii) a labeling reagent comprising a marker moiety M and a reactive group R

M-R wherein the marker moiety M and the reactive group R are covalently linked together, the M comprising at least one moiety that comprises a ligand, a dye, or both a ligand and a dye; and the reactive group R being capable of forming a carbon-carbon linkage with the target; and (b) reacting the target (i) and the labeling reagent (ii) under conditions such that a carbon-carbon linkage forms between the target (i) and the labeling reagent (ii), thereby labeling the target (i) with the marker moiety M.

This invention also provides a labeled target, the target having been labeled by a process comprising the steps of (a) providing: (i) the target; (ii) a labeling reagent comprising a marker moiety M and a reactive group R

M-R wherein the marker moiety M and the reactive group R are covalently linked together, the M comprising at least one moiety that comprises a ligand, a dye, or both a ligand and a dye; and the reactive group R being capable of forming a carbon-carbon linkage with the target; (b) reacting the target (i) and the labeling reagent (ii) under conditions such that a carbon-carbon linkage forms between the target (i) and the labeling reagent (ii), thereby labeling the target (i) with the marker moiety M.

Also provided by this invention is a process for preparing a cyanine dye labeling reagent, the process comprising the steps of (a) providing:

(i) a first intermediate compound comprising:

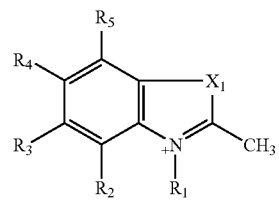

wherein $X_1$ comprises carbon, oxygen, nitrogen or sulfur; and (ii) a second intermediate compound comprising:

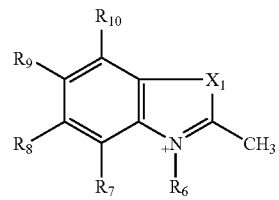

wherein $X_1$ comprises carbon, oxygen, nitrogen or sulfur; wherein at least one of $R_1$ through $R_{10}$ comprises a reactive group capable of forming a carbon-carbon linkage with a target, and (ii) linking reagents suitable for linking the first intermediate compound and the second intermediate compound; (b) forming a reaction mixture comprising the first intermediate compound (i), the second intermediate compound (ii), and the linking reagents under conditions to link (i) and (ii) to form

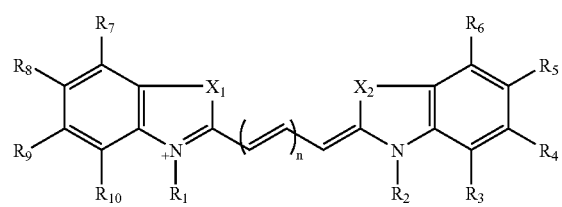

wherein at least one of $R_1$ through $R_{10}$ comprises a reactive group capable of forming a carbon-carbon linkage with a target, and wherein n is an integer of 1, 2 or 3, and wherein $X_1$ and $X_2$ independently comprise carbon, oxygen, nitrogen or sulfur.

Further provided by this invention is a labeling reagent comprising an aphenylic analog of a rhodamine dye, the analog comprising at least one reactive group for attaching the labeling reagent to a target, the at least one reactive group being attached directly to the analog or indirectly through a linker arm.

The present invention also concerns a labeled nucleotide comprising an aphenylic-analog of a rhodamine dye, wherein the dye is attached directly to the nucleotide or indirectly through a linker.

This invention also provides a labeled target comprising

T-L-M wherein T is a target, M is a marker moiety and L is a chemical group covalently linking the M to T, the chemical group L comprising a backbone that comprises at least one rigid group that comprises one or more of:

(a)
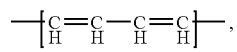

(b)
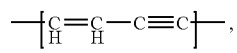

(c)
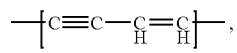

(d) multimers of (a), (b) or (c), and (e) any combinations of (a), (b), (c) and (d).

The present invention also provides a labeling reagent comprising

R-L-M wherein R is a reactive group, M is a marker moiety and L is a chemical group covalently linking the M to R, the chemical group L comprising a backbone that comprises at least one rigid group that comprises one or more of:

(a)
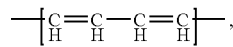

(b)
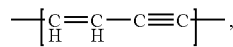

(c)
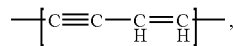

(d) multimers of (a), (b) or (c), and (e) any combinations of (a), (b), (c) and (d).

Also provided is a labeled target comprising

T-L-M wherein T is a target, M is a marker moiety and L is a chemical group covalently linking the M to T, the chemical group L comprising a backbone that comprises at least two consecutive-polar rigid units.

Additionally provided is a labeling reagent comprising

R-L-M wherein R is a reactive group, M is a marker moiety and L is a chemical group covalently linking the M to R, the chemical group L comprising a backbone that comprises at least two consecutive polar rigid units.

The invention herein also provides a labeled target comprising

T-L-M wherein T is a target, M is a marker moiety and L is a chemical group covalently linking the M to T, the chemical group L comprising a backbone that comprises at least two consecutive peptide bonds.

Another aspect of this invention is a labeling reagent comprising

R-L-M wherein R is a reactive group, M is a marker moiety and L is a chemical group covalently linking the M to R, the chemical group L comprising a backbone that comprises at least two consecutive peptide bonds.

Another aspect concerns a labeling reagent comprising a nonmetallic porphyrin, the reagent comprising:

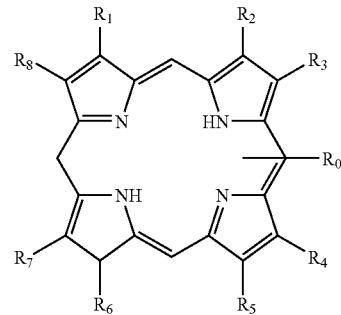

wherein $R_0$ is a reactive group and is attached directly or indirectly to the nonmetallic porphyrin, and $R_1$ through $R_8$ independently comprise hydrogen, aliphatic, unsaturated aliphatic, cyclic, heterocyclic, aromatic, heteroaromatic, charged or polar groups, or any combinations of the foregoing.

Further described and provided is a labeled target comprising a nonmetallic porphyrin, the reagent comprising:

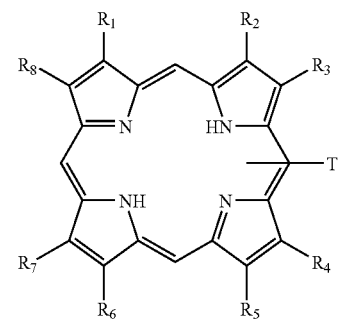

wherein T is a target molecule attached directly or indirectly to the nonmetallic porphyrin and $R_1$ through $R_8$ independently comprise hydrogen, aliphatic, unsaturated aliphatic, cyclic, heterocyclic, aromatic, heteroaromatic, charged or polar groups, or any combinations of the foregoing.

Another part of the present invention is a process for determining the amount of a nucleic acid in a sample of interest, the process comprising the steps of: (a) providing: (i) the sample of interest; (ii) a dye comprising a first phenanthridinium moiety linked to a second phenanthridinium moiety through the phenyl group in each of the first and second phenanthridinium moieties; (iii) reagents for carrying out dye binding, hybridization, strand extension, or any combination thereof; (b) forming a mixture of (i), (ii) and (iii) above, to produce a complex comprising the dye (ii) and any nucleic acid that may be present in the sample of interest (i); (c) illuminating the mixture formed in step (b) at a wavelength below 400 nanometers (nm); and (d) measuring fluorescent emission from the illuminated mixture in step (c), the emission being proportional to the quantity of any nucleic acid present in the sample of interest (i).

The present invention also provides a composition comprising at least one of the following dye structures:

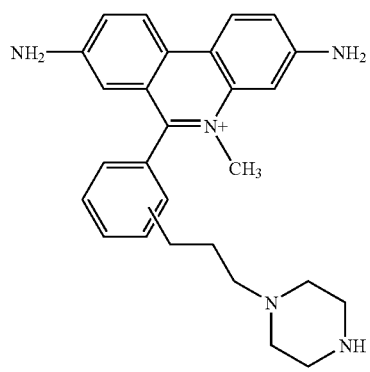
(a)

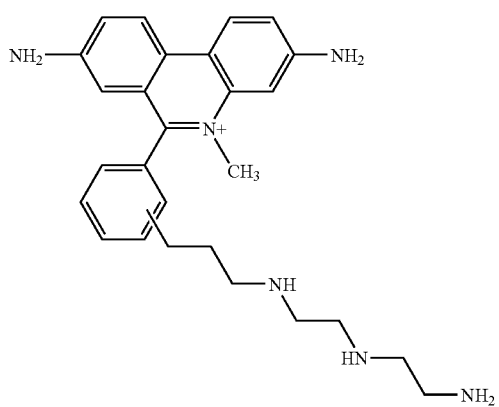
(b)

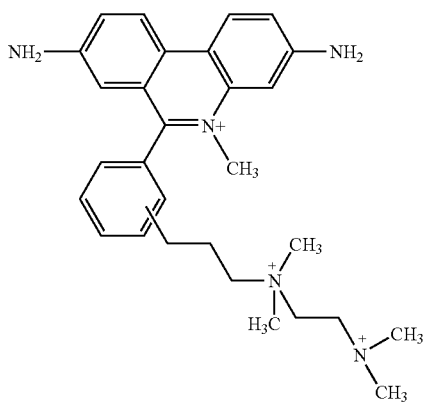
(c)

and

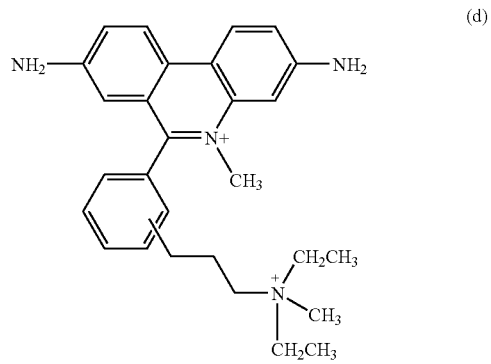
(d)

Also provided by the present invention is the use of the just-described compositions in a process for determining the amount of a nucleic acid in a sample of interest, the process comprising the steps of: (a) providing: (i) the sample of interest; (ii) the dye (a), (b), (c) or (d) from the composition just described; (iii) reagents for carrying out dye binding, hybridization, strand extension, or any combination thereof; (b) forming a mixture of (i), (ii) and (iii) above, to produce a complex comprising the dye (ii) and any nucleic acid that may be present in the sample of interest (i); (c) illuminating the mixture formed in step (b) at a first wavelength; and (d) measuring at a second wavelength any fluorescent emission from the illuminated mixture in step (c), the emission being proportional to the quantity of any nucleic acid present in the sample of interest (i).

This invention provides a heterodimeric dye composition, the composition comprising a first dye that comprises a phenanthridinium moiety; and a second dye that is different from the first dye, the second dye being attached through the phenyl ring of the phenanthridium moiety.

This invention also provides a process for determining the amount of a nucleic acid in a sample of interest -using the last-described composition. The process comprises the steps of: (a) providing: (i) the sample of interest; (ii) the dye last-described; (iii) reagents for carrying out dye binding, hybridization, strand extension, or any combination thereof;

(b) forming a mixture of (i), (ii) and (iii) above, to produce a complex comprising the dye (ii) and any nucleic acid that may be present in the sample of interest (i); (c) illuminating the mixture formed in step (b) at a first wavelength; and (d) measuring at a second wavelength any fluorescent emission from the illuminated mixture in step (c), the emission being proportional to the quantity of any nucleic acid present in the sample of interest (i).

A chemiluminescent reagent is also provided by this invention, the chemiluminescent reagent having the structure:

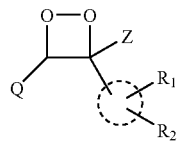

wherein Q comprises a cycloalkyl or polycycloalkyl group attached covalently to the 4-membered ring portion of the dioxetane above directly or indirectly through a linkage group; wherein Z comprises hydrogen, alkyl, aryl, aralkyl, alkaryl, heteroalkyl, heteroaryl, cycloalkyl or cycloheteroalkyl; and wherein $R_1$ and $R_2$ comprise chemical moieties attached to different sites of a cyclic ring attached to the dioxetane, and wherein $R_1$ is enzymatically converted into $R_1^*$ which comprises a chemical reactive group $G_1$, and wherein $R_2$ is attached to the cyclic ring through an oxygen, nitrogen or sulfur atom and comprises a chemical reactive group $G_2$ which reacts with the $G_1$ to convert the dioxetane to an unstable light-emitting dioxetane form.

Using the last-described composition, the invention further provides a process for detecting the presence or quantity of enzymatic activity of interest in a sample. The process comprises the steps of: (a) providing: (i) the sample suspected of containing enzymatic activity; (ii) the chemiluminescent reagent last-described; (ii) reagents and buffers for carrying out chemiluminescent reactions; (b) forming a mixture of: (1) (i), (ii) and (iii); or (2) (ii) and (iii) and contacting the mixture of (ii) and (iii) with (i); (c) enzymatically. converting the chemiluminescent reagent just described (ii) into an unstable light-emitting dioxetane form; and (d) measuring the quantity of light generated by the enzymatic conversion in step (c).

Another chemiluminescent reagent provided by the present invention is one having the structure:

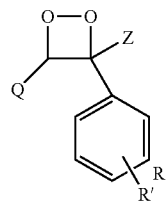

wherein Q comprises a cycloalkyl or polycycloalkyl group attached covalently to the 4-membered ring portion of the dioxetane above directly or indirectly through a linkage group; wherein Z comprises hydrogen, alkyl, aryl, aralkyl, alkaryl, heteroalkyl, heteroaryl, cycloalkyl or cycloheteroalkyl; and wherein R comprises a chemical linker having a reactive site attached to the aromatic ring in the structure; and wherein R' comprises a substrate for an non-cleaving enzymatic process, wherein the product of the enzymatic process leads to further chemical rearrangements that generate an unstable light emitting dioxetane form.

The invention also provides a process for detecting the presence or quantity of enzymatic activity of interest in a sample using the last-described chemiluminescent reagent. The process comprises the steps of: (a) providing: (i) the sample suspected of containing enzymatic activity; (ii) the chemiluminescent reagent last-described; (ii) reagents and buffers for carrying out chemiluminescent reactions; (b) forming a mixture of: (1) (i), (ii) and (iii); or (2) (ii) and (iii) and contacting the mixture of (ii) and (iii) with (i); (c) enzymatically converting the chemiluminescent reagent just described above (ii) into an unstable light-emitting dioxetane form; and (d) measuring the quantity of light generated by the enzymatic conversion in step (c).

A dye composition is also provided by this invention, the dye composition having the formula R-Fluorescent Dye wherein R is covalently linked to the Fluorescent Dye comprises two or more members in combination from a) unsaturated aliphatic groups; b) unsaturated heterocyclic groups; c) aromatic groups; and wherein R is capable of providing a conjugated system or an electron delocalized system with the fluorescent dye.

A labeled target is further provided, the labeled target having the structure

[R-Dye]-target wherein the Dye is a fluorescent dye, wherein R is covalently linked to the Dye, and wherein R comprises two or more members in combination from a) unsaturated aliphatic groups; b) unsaturated heterocyclic groups; c) aromatic groups; and wherein R is capable of providing a conjugated system or an electron delocalized system with the Dye.

Other embodiments and aspects of the present invention are further described below.

BRIEF DESCRIPTION OF THE FIGURES

FIG. 1 illustrates several examples of linker arms made with rigid polar units.

FIG. 2 shows structures of various homodimers of Ethidium Bromide: A) meta-EthD B) EthD-1 and C) EthD-2.

FIG. 4 depicts variations of placement of primers (SEQ ID NO: 5) in a double stranded nucleic acid.

FIG. 5 is an illustration of the use of nucleotides with energy transfer elements.

FIG. 13 shows the use of a CNAC (SEQ ID NO: 4) to eliminate a portion of a poly A tail followed by incorporation of an oligo C primer binding sequence (SEQ ID NOS 10-12).

DETAILED DESCRIPTION OF THE INVENTION

Figure 3:
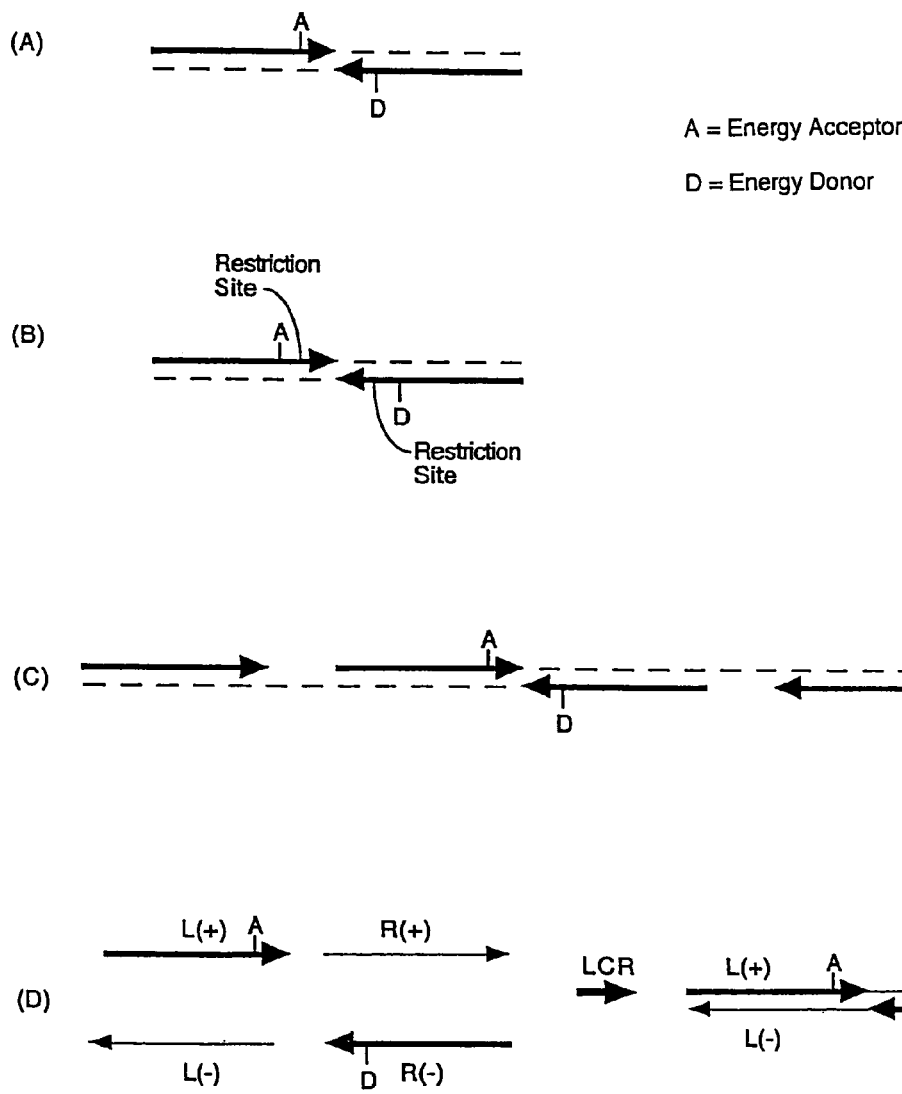
FIG. 3 illustrates the use of primers with first and second energy transfer elements:
  double stranded nucleic acid made from extension of two primers
  double stranded SDA amplicon
  Nested PCR
  Ligase Chain Reaction.

The present invention discloses novel methods and compositions for the preparation of compounds labeled with ligands and dyes. Included within the present disclosure are novel labeling reagents, novel dyes and novel methods that can be used to synthesize the novel reagents of the present invention. The novel methods of the present invention may also be applied to the synthesis of compounds that have been described previously.

1. Labeling Reagents Which Participate in Carbon-Carbon Bond Formation

One aspect of the present invention discloses novel labeling reagents that comprise a reactive group capable of creating a carbon-carbon bond between a marker or label and a desirable target molecule. This is in contrast to labeling reagents described in prior art which employed protein derived chemistries involving formation of a bond between an amine, sulfhydryl or hydroxyl group and an appropriate reactive group. The novel labeling reagent of the present invention should provide a highly efficient means of attaching signal moieties to desirable target molecules. Thus, the novel labeling reagents of the present invention comprise a ligand or dye portion and a reactive group capable of creating a carbon-carbon bond. In addition, it may be desirable to insert a linker arm that separates the ligand or dye portion from the reactive group. This may provide more efficient coupling between the novel labeling reagent and an intended target molecule. The presence and nature of the linker arm may also increase the biological or chemical activity of the labeled target molecule. The novel reagents of the present invention can be used to label any target molecule that is capable of participating in bond formation with the reactive group of the labeling reagent. The target molecule may be in its native state or it may have been modified to participate in formation of a carbon-carbon bond with the novel labeling reagent.

Ligands that may find use with the present invention can include but not be limited to sugars, lectins, antigens, intercalators, chelators, biotin, digoxygenin and combinations thereof. The particular choice of a dye used to synthesize a novel labeling reagent of the present invention may depend upon physical characteristics such as absorption maxima, emission maxima, quantum yields, chemical stability and solvent solubility. A large number of fluorescent and chemiluminescent compounds have been shown to be useful for labeling proteins and nucleic acids. Examples of compounds that may be used as the dye portion can include but not be limited to xanthene, anthracene, cyanine, porphyrin and coumarin dyes. Examples of xanthene dyes that may find use With the present invention can include but not be limited to fluorescein, 6-carboxyfluorescein.(6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4', 5'-dichloro-2,'7'-dimethoxyfluorescein (JOE), 5-carboxy-2', 4',5',7'-tetrachlorofluorescein (ZOE) rhodol, rhodamine, tetramethylrhodamine (TAMRA), 4,7-dichlorotetramethyl rhodamine (DTAMRA), rhodamine X (ROX) and Texas Red. Examples of cyanine dyes that may find use with the present invention can include but not be limited to Cy 3, Cy 3.5, Cy 5, Cy 5.5, Cy 7 and Cy 7.5. Other dyes that may find use with the present invention can include but not be limited to energy transfer dyes, composite dyes and other aromatic compounds that give fluorescent signals. Chemiluminescent compounds that may be used in the present invention can include but not be limited to dioxetane and acridinium esters It should also be understood that ligands and dyes are not mutually exclusive groups. For instance, fluorescein is a well known example of a moiety that has been used as a fluorescent label and also as an antigen for labeled antibodies.

The reactive group of the novel labeling reagents of the present invention is chosen from chemical moieties that are known to be able to participate in carbon-carbon bond formation thereby allowing the novel labeling reagent to attach a label to a suitable target molecule. Examples of such reactive groups can comprise but not be limited to alkenes, alkynes, metallo-organic compounds and halogenated compounds. The metallo-organic and halogenated compounds can comprise aromatic, heterocyclic, alkene, and alkyne groups as well as various combinations thereof. Although such groups have been described previously for synthesis of labeled compounds, these reactive groups were only used in the context of adding amino groups to nucleic acids in order to make nucleotides and polynucleotides look like proteins (U.S. Pat. Nos. 4,711,955 and 5,047,519, both of which are incorporated by reference). In the present invention, the reactive group of the novel labeling reagent can be attached directly to a ligand or dye, at the terminal end of a linking arm or at an internal site within a linking arm. A review of various methods for use of metallo-organic and halogenated compounds is given by Larock (1982, Tetrahedron Report 128; 1713-1754), Robins et al. (J. Org Chem 1983, 48; 1854-1862), Hobbs and Cocuzza (U.S. Pat. No. 5,047,519), Eglinton and McCrae (1963, Advances in Organic Synthesis 4; 225-328) and Rieke (2000, Aldrichimica Acta 33; 52-60) all of which are incorporated by reference.

A linking arm that comprises a portion of the novel labeling reagents can be of any desired length and can be comprised of any suitable atoms that can include but not be limited to carbon, nitrogen, oxygen, sulfur and any combination thereof. Chemical groups that can comprise the linker arm can include but not be limited to aliphatic bonds, double bonds, triple bonds, peptide bonds, aromatic rings, aliphatic rings, heterocyclic rings, ethers, esters, amides, and thioamides. The linking arm can form a rigid structure or be flexible in nature.

The present invention may be used to label a large variety of target molecules. The targets may intrinsically comprise chemical moieties that can participate in formation of a carbon-carbon bond with the reactive group of the novel labeling reagent or the targets may be modified such that they comprise such a group. Examples of chemical moieties on target molecules that can combine with the reactive group of the novel labeling reagent can comprise but not be limited to alkenes, alkynes, metallo-organic compounds and halogenated compounds. The metallo-organic and halogenated compounds can comprise aromatic, heterocyclic, alkene and alkyne groups as well as various combinations thereof. Target molecules that may find use with the present invention can include but not be limited to nucleotides, oligonucleotides, polynucleotides, peptides, oligopeptides, proteins, ligands, synthetic compounds, synthetic polymers, saccharides, polysaccharides, lipids and hormones. Nucleotides that can be labeled by these compounds can include but not be limited to monophosphates, diphosphates or triphospates. They may be ribonucleotides or deoxynucleotides. Modified nucleotides or Nucleotides analogues of any of the foregoing may also be used if desired. Examples of modified nucleotides can include but not be limited to dideoxy nucleotides and nucleotides with 3' amino or 3' phosphate groups. Examples of nucleotide analogues can include but not be limited to peptide nucleic acids, arabinosides, and acyclo versions. These analogues may be used as nucleotides or as components of oligonucleotides or polynucleotides. Synthesis of a labeled oligonucleotide or polynucleotide can be carried out by the use of nucleotides that have been labeled by the novel labeling reagent. Alternatively, modified nucleotides that have chemical groups that can be used for carbon-carbon bond formation with the novel labeling reagents can be used to synthesize oligonucleotides or polynucleotides. In this method, the presence of reactive groups in the oligonucleotide or polynucleotide products allows a subsequent reaction with the novel labeling reagents of the present invention. Additionally, unmodified oligonucleotides and polynucleotides can be chemically treated such that they comprise groups capable of participating in carbon-carbon bond formation.

Attachment of the novel labeling reagents of the present invention to desirable target molecules can be carried out by any of a variety of means, known to those skilled in the art. For instance, the acetoxymercuration reaction is a well known and established procedure for introducing covalently bound mercury atoms onto the 5-position of the pyrimidine ring or the C-7 position of a deazapurine ring (Dale et al., (1975) Biochemistry 14, 2447-2457, Dale et. al. (1973) Proc. Natl. Acad. Sci. USA 70; 2238-2242. The nucleotides are treated with the mercuric acetate in sodium acetate buffer to convert them into mercuric salts. In the presence of $K_2PdCl_4$, the addition of a labeled reagent of the present invention that has been prepared with a terminal double bond will allow a carbon-carbon double bond to be formed between the aromatic ring of the nucleotide and the terminal carbon of the double bond of the labeling reagent thereby attaching the label to the nucleotide. In the case of novel labeling reagents of cyanine dyes with double bonds at the teminus of a linker, the mercuric nucleotide reacts with the double bond at the terminus of the linker arm rather that the aromatic ring or the conjugated double bond between the two rings of the cyanine dye moiety.

In an alternative use of the reaction described above, a novel labeling reagent of the present invention can be prepared where the reactive group is a mercury salt. This compound can now react with an unsaturated bond on the target that is desired to be labeled. This bond may be an intrinsic part of the target molecule or the target molecule may be modified to include such a group. Reactions can also be carried out where both the labeling reagent and the target molecules comprise mercury salts. For instance, Larock (1982 op. cit. Eqns. 146-151) has described how two groups that each have the structure R1—C=C—HgCl can be joined together in the presence of appropriate catalysts.

One advantage of the mercuration and palladium catalyzed addition reactions is that they can be carried out in water with a small amount of organic solvent added to increase solubility if necessary. This procedure can be carried out with the nucleotides in any form, for example with ribonucleotides, deoxynucleotides, dideoxynucleotides and any analogue, as well as with oligonucleotides, oligonucleotide analogues, protein nucleic acid complexes and polynucleotides. Alternatively the novel labeling reagent can be prepared with a reactive arm containing a terminal triple bond or any other substance which is capable of forming the carbon-carbon double bond with the target molecule.

2. Labeling Proteins by Carbon-Carbon Bond Formation

An important use for the novel labeling reagent may also be for attaching signal groups to proteins. In this particular case, modifications of the protein can be made to make them resemble the nucleic acid target described above. For instance, a target protein can be reacted with mercuric acetate thereby forming mercurate compounds at tyrosine, tryptophan or phenylalanine residues in the protein. The protein is now available for reacting with a novel labeling reagent that has an double bond reactive group where displacement of the mercury will take place while attaching the label. If desired, thiol groups in the protein can be protected on the protein by treatment with 2,2'-dipyridyl disulfide prior to the mercuration step.

Amino acids that have primary amines are also sites on a protein that may be used with the novel labeling reagent. For instance, proteins that lack tyrosine groups can be modified with Bolton-Hunter active ester to introduce tyrosine groups onto primary amines. These can then be subsequently used as described above. Alternatively, the protein can be modified with acrylic acid active ester to introduce terminal double bonds into residues that contain primary amines. This modification would allow proteins to be used with novel labeling reagents of the present invention that have mercurate compounds as reactive groups.

3. Dye Precursors With Reactive Groups for Carbon-Carbon Bond Formation

Attachment of a group to a marker that is suitable for participating in a carbon-carbon bond can be carried out by modification of the marker. On the other hand, attachment can take place with an intermediate that is used to synthesize a particular marker. For example, cyanine dye labeling reagents have the following structure:

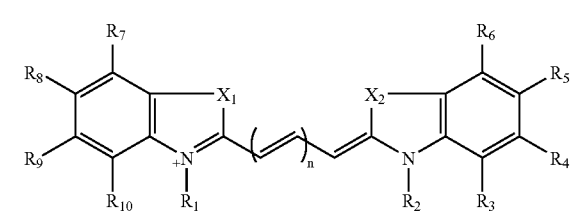

where n=1, 2 or 3; X1 and X2 can be S, O, N, $CH_2$ or $C(CH_3)_2$ and R1-R8 comprises a reactive group that could be used to join the cyanine dye to a desirable target molecule. Cyanine dyes are prepared by linking together two indolenine precursor units with an intervening unsaturated chain. The particular number of units making up the chain determines the particular absorption and emission spectra of the cyanine dye.

According to the method of the present invention, cyanine dyes can be prepared by attaching a linker arm containing a reactive group capable of generating a carbon-carbon bond to the indolenine ring that is a precursor to a cyanine dye. This modified indolenine is a novel compound that can then be used as a reagent in a reaction where it is coupled to a second indolenine ring through an intervening unsaturated alkyl chain to synthesize a cyanine dye with the structure described above. The second indolenine can be the same as the first or it may be an unmodified version that lacks the linker arm and reactive group. The same novel indolenine compound can be used to make a variety of different cyanine dyes depending upon the nature of the second indolenine ring and the particular unsaturated chain joining the two indolenine rings. As a result of this procedure, when the cyanine dye product is formed by joining the precursor rings, it already comprises a linker arm with a reactive group and is ready to be attached to a suitable target molecule.

4. Novel Rhodamine Dyes Without the Phenyl group

In another aspect of the present invention, new dyes and means for their synthesis are disclosed. In previous art, derivatives of rhodamine typically have an aromatic group between the dye and the reactive group that is used to attach the rhodamine to a desirable molecule. In the present invention, it is disclosed that stable nucleotides can be synthesized that comprise rhodamine analogues where the linker arm joining the dye to a base on the nucleotides lacks the aromatic group that is normally present in rhodamine. It is a surprising consequence that incorporation of such nucleotides becomes more acceptable to a polymerase such that the modified nucleotide can be used without mixing it with unmodified nucleotides. As such, the present invention discloses the following novel rhodamine analogues:

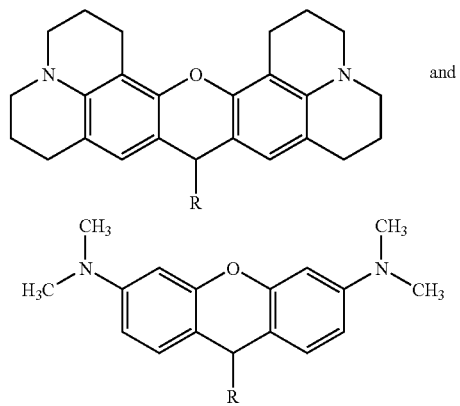

and where R is a reactive group.

5. Rigid Linker Arms

In another aspect of the present invention, methods and compositions are disclosed that enable modified nucleotides to be used more efficiently in enzymatic and chemical means of synthesis and/or allow them to function more efficiently when they are part of a polynucleotide. In one embodiment of the present invention, an increased and directed separation is achieved between a target molecule and the group that has been added to provide a marker or label. In the present invention,: the following novel compositions are disclosed that have the formulas:

T-L-M and R-L-M

In the diagram above, T is a target for attachment of a marker or label; R is a reactive group that may be used for attachment to a target and M is a marker or label.

In one aspect of the present invention, L is a chemical group that covalently connects the M moiety to the T moiety or R moiety and comprises one or more of the following groups:

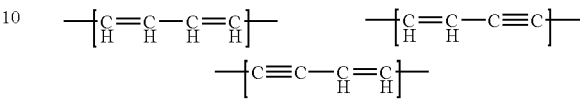

The alkene groups can be in either cis or trans configuration with regard to each other and they may comprise only hydrogen atoms bonded to the carbon atoms or they may be substituted. In a preferred mode, directionality is derived from having one of the groups above immediately linked to the target, separated by no more than a single intervening atom or linked to the target through a rigid polar unit.

In another aspect of the present invention, L is a chemical group that covalently connects the M moiety to the T moiety and comprises at least two consecutive rigid polar units.

Examples of targets that may find use in the present invention can include but not be limited to nucleotides, oligonucleotides, polynucleotides. peptides, polypeptides, cytokines, ligands, haptens, antigens and solid supports. Examples of solid support that may find use with the present invention can include but not be limited to beads, tubes, plastic slides, glass slides, microchip arrays, wells and depressions.

Examples of reactive groups that may find use with the present invention can include but not be limited to isothiocyanate, isocyanate, monochlorotriazine, dichlorotriazine, mono or di-halogen substituted pyridine, mono or di-halogen substituted diazine, aziridine, sulfonyl halide, acid halide, hydroxy-succinimide ester, hydroxy-sulfosuccinimide ester, imido esters, glyoxal groups, aldehydes amines, sulfhydryl groups, hydroxyl groups. Also included are groups that can participate in carbon carbon bond formation as disclosed previously.

In the present invention, a rigid unit is defined as a group of atoms where the spatial relations between the atoms are relatively static.

In the present invention, when two moieties are described as consecutive, the moieties are adjacent or directly next to each other. Additionally, two consecutive moieties can be separated by no more than one atom, i.e. a single atom.

In the present invention, a rigid unit is non-polar when it essentially comprises the same type of atoms. Examples of non-polar rigid units would be alkenes, alkynes, unsaturated rings, partially saturated rings and completely saturated rings that comprise only carbon and hydrogen.

In the present invention, a rigid unit is polar when it comprises at least two or more different atoms thereby distributing the charge unequally through the unit. Examples of an arrangement that could contribute to polarity could include but not be limited to a carbon atom that is bonded to N, S, O, P, or a halogen. The heteroatoms that are bonded to the carbon may be used alone or they may be part of polar or charged functional groups. Examples of the latter can include but not be limited to —OH, —SH, —SO$_3$, —PO$_4$, —COOH and —NH$_2$ groups. The rigid units can comprise backbones that are linear, branched or in ring form. The ring forms that also comprise polar or charged functional groups attached to the rings may be unsaturated rings, partially saturated rings and completely saturated rings. Multimers of two or more such polar rigid units will provide rigid extended arms that create a defined spatial relationship between a target molecule and a marker or signal generating moiety.

In the present invention, unsubstituted heterocyclic aromatic compounds would be considered to be non-polar rigid units due to the electron sharing in the ring. On the other hand, substituted heterocyclic aromatic compounds that comprise polar or charged functional groups attached to the rings would be considered to be polar rigid units.

Examples of linear polar rigid units that would be useful in the present invention can include but not be limited to moieties comprising peptide bonds. Examples of cyclic polar units that have inherent rigidity can include but not be limited to sugars. Examples of groups that would have utility in the present invention that have rigidity derived from the interactions between subunits can include but not be limited to charged components where charge repulsions can maximize distances between subunits. When negatively charged components are used, there can also be repulsion away from the negatively charged polynucleotide itself. The linker may also be designed with bulky side groups that interfere with rotational changes thereby maintaining a discrete spatial structure with regard to the relationship of a base and a signal or reactive group.

The distance of the reactive group or signal moiety from the target molecule would be determined by the number and nature of the rigid units making up the spacer. Thus, a series of three rigid units that comprise an alkene bond followed by two peptide bonds would extend the signal group directly away from the nucleotide as shown in FIG. 1A. This particular example would comprise a non-polar rigid unit as well as two polar rigid units. A series of multiple peptide bonds could still provide rigidity while extending the dye or marker further away from the target molecule as shown in FIG. 1B. In this particular illustration a uracil nucleoside is used as a target and glycine subunits are used to provide a series of peptide bonds. Different amino acids may also have been used if so desired, where the various constituents of the R groups of the amino acids may be chosen to endow other properties such as solubility or charge upon the rigid arm.

A linker that is comprised of rigid units will depend upon the particular relationship between the rigid units for whether the overall structure is rigid or not. For instance, multiple peptide bonds have been used in prior art. However, the beneficial qualities of having such bonds were lost by the inclusion of aliphatic carbon groups in between the peptide. In essence, these were rigid units joined by flexible linkers. As seen in FIG. 1, the present invention allows for at most a single atom between the rigid units, thereby limiting the extent of flexibility between rigid-units. Similarly other groups of a non-carbon nature could be used between groups that would retain an overall rigidity while contributing a potentially desirable directionality. An illustrative example of such a group would be a —S— bond between two rigid units.

As described above, sugar groups may also be used in carrying out the present invention. There are a wide variety of sugars that can be used as individual rigid units and a large number of ways that these sugars can be linked together either enzymatically or chemically has been extensively described in the literature.

Although the present invention makes use of two or more polar rigid units to create a rigid linker arm, it is understood that flexible groups and non-polar rigid units may also be included in the rigid linker arms. For instance, FIG. 1 makes use of an alkene bond between the peptide bonds and the uracil moiety. In addition, additional flexible units, rigid units or combinations thereof may be included between the last peptide bond and the dye molecule in FIG. 1 while retaining the effectiveness of the linker.

In the present invention, the presence of such an extended linkage away from a nucleotide should decrease deleterious effects upon incorporation since the problematic group should be spatially displaced from the active site where enzymatic incorporation is taking place. In addition, after a modified nucleotide is incorporated either enzymatically or synthetically, functionality may also be increased by the use of the present invention. For instance, extension of a hapten or a chemically reactive group further from an oligonucleotide or polynucleotide should provide increased accessibility thereby improving binding or coupling efficiencies. In addition, signal generation groups could also be displaced away from the oligonucleotide or polynucleotide by the use of the present invention if interference effects are caused by proximity.

The particular point of attachment of the linkers described in the present invention may take advantage of previously described art for flexible linkers. As such, the nucleotides may be normal nucleotides or they may be modified nucleotides or nucleotide analogues with various substituents either added or replacing components in the base, sugar or phosphate moieties as disclosed in U.S. Pat. Nos. 4,711,955; 5,241,060; 4,952,685 and 5,013,831; all of which are hereby incorporated by reference). In addition, these modifications may be non-disruptive, semi-disruptive or disruptive. The point of attachment may be the base, sugar or phosphate as described in the previously recited disclosures, but attachment to the base is particularly useful in the present invention.

A further benefit of the present invention is that some of the linkers that have been described may offer beneficial results due to their chemistry as well as structure. For instance, the last peptide in a linker composed of peptide subunits offers an amine group that may be used to attach useful groups such as signal moieties. In prior art, amine groups were located at the ends of aliphatic chains, with pK values of about 11. However, since coupling reactions are usually carried out at around pH 8 values, very little of the amine group is in a reactive form at any given time, thereby limiting the efficiency and kinetics of the reaction. In contrast, the amine group at the end of peptide chain has a pK of about 9, a value that is more compatible with the intended coupling reaction. Thereby, the present invention allows more effective coupling of a nucleotide or polynucleotide to an appropriate group.

Also, although this particular aspect of the present invention has been described in terms of a rigid linker intervening between a nucleotide and a dye, other applications may also enjoy the benefits of the present invention. For instance, labeling of proteins can be improved by using the rigid arm of the present invention between the protein and a signal moiety. Examples of proteins that might enjoy these benefits can include but not be limited to antibodies, enzymes, cytokines and libraries of oligopeptides or polypeptides. As described previously for nucleic acids, the use of the present invention may improve the properties of the labeled compound as well as the efficiency of the labeling itself. Additionally, there are many procedures that involve fixation of a ligand, hapten, protein or a nucleic acid to a solid support. Examples of such supports can include but not be limited to beads, tubes, microtitre plates, glass slides, plastic slides, microchip arrays, wells and depressions. The present invention can be used to generate a directed separation of a ligand, hapten, protein or nucleic acid away from the surface of the support. Examples of proteins that might enjoy these benefits can include but not be limited to antibodies, enzymes, cytokines and libraries of oligopeptides or polypeptides.

6. Non-Metallic Porphyrins With Reactive Groups on Non-Pyrrole Positions

In another aspect of the present invention, a novel labeling reagent is disclosed that comprises a non-metallic porphyrin with a reactive group at a non-pyrrole position. The spectral quality of non-metallic alkylated porphyrins as fluorescent dyes has been described in Hendrix in U.S. Pat. No. 4,707,454 (incorporated by reference) where Stokes shifts over 150 nm were disclosed. However, when describing reactive groups for the porphyrins, the only teachings that were disclosed made use of chemical groups on the pyrrole positions. Therefore, it is a subject of the present invention that non-metallic porphyrins can be derived which independently comprise hydrogen, aliphatic, unsaturated aliphatic, cyclic, heterocyclic, aromatic, heteroaromatic, charged or polar groups on any or all of the eight pyrrole positions and use one of the non-pyrrole positions as a site for attaching a reactive group. This composition has the following structure:

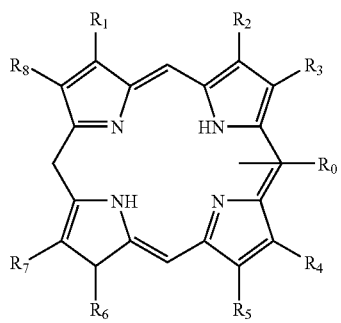

where $R_o$ comprises a reactive group attached directly or indirectly to a non-pyrrole position of the porphyrin (i.e., the α, β, γ, or δ positions) and $R_1$ through $R_8$ are as defined just above.

Any of the reactive groups that have been described previously may find use in the present invention as $R_0$. $R_1$ through $R_8$ may comprise the same groups or they may be different. If desired, the alkyl groups may also further comprise polar or charged groups that may aid in increasing the aqueous solubility of the porphyrin. Also if desired, there may be a linker used to attach a reactive group to the porphyrin. The particular rigid arm used in this aspect of the present invention can be any linker arm that has been previously disclosed or described but it is especially preferred that the rigid linker of the present invention be used. A nitro group can be added to a non-pyrrole position as described by Fuhrhop and Smith "Laboratory Methods" Chapter 19 in Porphyrins and Metalloporphyrins, Kevin M. Smith, editor, Elsevier Scientific Publishing Company, Amsterdam, 1975, hereby incorporated by reference. Reduction of this group to an amine is well known to those skilled in the art and further reaction can be carried out to add a linker or a reactive group by standard techniques.

Any of the previously described targets may be labeled by the non-metallic porphyrins of the present invention. For example, the non-metallic phorphyrins of the present invention may find use by incorporation of a porphryin labeled nucleotide or synthetically by a porphyrin labeled phosphoramidite. Alternatively, oligonucleotide or polynucleotides can be synthesized that have derivatized nucleotides that are suitable for reaction with a chemically compatible derivative of a non-metallic porphyrin in a post-synthetic step. Labeled oligonucleotides and polynucleotides that comprise the non-metallic porphyrin of the present invention should enjoy a large Stokes shift with high efficiency emission. This composition and method of detection will enjoy a high level of sensitivity as well as enabling high level of discrimination from other compounds that may be excited at the same wavelength. For instance, if a library of transcripts is labeled with fluorescein and a second library is labeled with octaethylporphine, illumination can be carried out by a single wavelength of 490 nm. Yet, discrimination between the particular fluorophores is easily distinguishable since the emission peak is 530 nm for fluorescein and the emission peak for octaethylporphine is 620 nm. At the same time, the quantum yield for the octaethylporphine is comparable to that of fluorescein. It is also understood that the non-metallic phorphyrins may be used in conjunction with any of the other novel methods that are disclosed herein.

7. Modification of Dyes by Groups that Participate in the Conjugation and/or Electron Delocalized System In another embodiment of the present invention, methods are disclosed for the synthesis of novel compositions that comprise two or more unsaturated compounds added to a fluorescent dye without a requirement for the presence of kenone groups in an intermediate. In the present invention, these unsaturated compounds can be unsaturated aliphatic groups, unsaturated cyclic compounds, unsaturated heterocyclic compounds, aromatic groups or any combinations thereof. Attachment of such groups allows them to participate in the conjugation and/or the electron delocalized system (Maulding and Roberts, op. cit. incorporated by reference) of the dye and confer changes upon the spectral characteristics of the dye. These changes can include changing the width of the excitation and emission peaks, shifting the positions of the excitation and emission peaks and increasing the quantum yield.

Since addition of:unsaturated groups to the dyes may decrease solubility or result in non-specific hydrophobic interactions, it is an objective of the present invention that this effect can be compensated by a further addition of charged or polar groups. These may be attached to the dye or to the unsaturated compounds. Also, since these novel dyes find use as labeling reagents, they may also comprise reactive groups suitable for attaching the label to desirable target molecules. The reactive groups can be directly or indirectly linked to the dye, to the unsaturated compounds or to the charged or polar modification groups.

The novel composition of this aspect of the present invention has the following structure:

R-Dye where Dye is a fluorescent dye; R is covalently linked to the Dye and R comprises two or more unsaturated compounds which can be unsaturated aliphatic groups, unsaturated cyclic compounds, unsaturated heterocyclic compounds, aromatic groups or combinations thereof. Furthermore, one or more members of R participates in the conjugation and/or electron delocalized system of the Dye. The unsaturated compounds can be substituted or unsubstituted. The unsaturated aliphatic group can comprise an alkene or an alkyne.

The aromatic group can comprise a phenyl group, an aryl group, or an aromatic heterocycle. When the groups are substituted, the substituents can include but not be limited to alkyl groups, aryl groups, alkoxy groups, phenoxy groups, hydroxyl groups, amines, amino groups, amido groups, carboxyl groups, sulfonates, sulfhydryl groups, nitro groups, phosphates or any group that can improve the properties of the dyes. In the case of an aromatic group, it may also be substituted by being part of a fused ring structure. Examples of such fused rings can include but not be limited to naphthalene, anthracene, and phenanthrene.

Groups that can be used as all or part of R can also be described as follows:

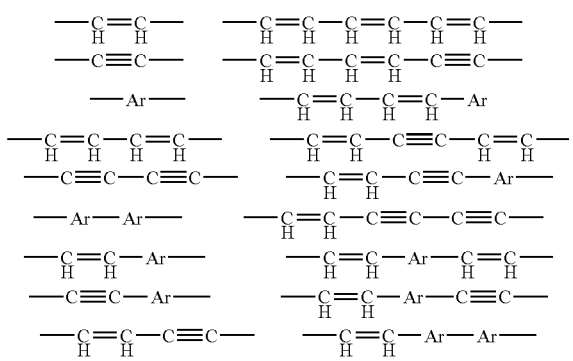

In the diagram above, Ar is an unsaturated cyclic compound, an unsaturated heterocyclic compound or an aromatic group. As described previously, the groups above may be substituted or unsubstituted.

Fluorescent dyes that may find use with the present invention can include but not be limited to anthracene, xanthene, cyanine, porphyrin, coumarin and composite dyes. In the case where anthracene is used as the Dye with an alkyne joined to the center ring and a phenyl group attached to the alkyne, the phenyl group will be substituted.

In another aspect of the present invention, a novel composition has the following structure:

where R and Dye are as described previously and where $R_1$ is covalently joined to R, Dye or to both R and Dye. $R_1$ further comprises one or more charged or polar groups to provide additional solubility. This may useful when the dye or the dye with the R modification has limited aqueous solubility or problems with non-specific hydrophobic interactions.

In another aspect of the present invention, a novel composition has the structure

where R, Dye and $R_1$ are as described previously and where $R_2$ is covalently attached to R, Dye, $R_1$ or any combination thereof and where $R_2$ further comprises a reactive group that can be used to attach the dye to a suitable target molecule. $R_2$ can comprise any of the reactive groups previously described including sulfhydryl, hydroxyl and amine groups, groups capable of reacting with sulfhydryl, hydroxyl and amine groups, and groups capable of forming a carbon-carbon bond. $R_2$ can further comprise a linker arm that that separates the reactive group from the dye. The linker arm can be of any desirable length and can comprise a backbone of carbon as well as non-carbon atoms. Non-carbon atioms that may find use can include but not be limited to sulfur, oxygen and nitrogen. The linker arm can comprise saturated, unsaturated or aromatic groups and may also comprise the rigid arms described previously.

In another aspect of the present invention, a novel labeled target comprises the structure:

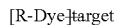

where R and Dye are as described previously. Targets that may find use with the present invention can include but not be limited to a protein, a peptide, a nucleic acid, a nucleotide or nucleotide analog, a receptor, a natural or synthetic drug, a synthetic oligomer, a synthetic polymer, a hormone, a lymphokine, a cytokine, a toxin, a ligand, an antigen, a hapten, an antibody, a carbohydrate, a sugar or an oligo- or polysaccharide. The labeled target can also further comprise $R_1$ covalently joined to R, Dye or to both R and Dye. $R_1$ further comprises one or more charged or polar groups to provide additional solubility. This may useful when the labeled target or an intermediate used for making the labeled target has limited aquaeous solubility or problems with non-specific hydrophobic interactions. The labeled target can also further comprise a linker arm as described above separating the dye from the target.

8. Intercalators

In another aspect of the present invention, a novel method is disclosed that provides enhanced discrimination between an intercalating dye that is bound to a target compared to dye that remains unbound. As described previously, ethidium bromide has been a popular reagent for detection and visualization of DNA in a number of formats. To investigate the effect of a second-phenanthridinium ring system on affinity to nucleic acids, a homodimeric form of ethidium bromide was synthesized and tested (Kuhlmann et al., (1978) Nucleic Acids Research, 5; 2629-2633). This compound, N,N-Bis[3-(3,8-diamino-5-methylphenanthridinium-6-yl) benzoyl]1,5-diaminopentane dichloride (meta-EthD) exhibited a much higher affinity to nucleic acids than the monomeric form. However, when fluorescence was measured at the standard wavelength of 493 nm, the increase in fluorescent emission after binding to nucleic acids was essentially the same as seen earlier for the ethidium bromide monomer.

It was a surprising. and unexpected result that when meta-EthD was used in a different manner than the standard format, a greatly enhanced discrimination between bound and unbound was observed. The present invention discloses that when two ethidium bromide molecules are joined together through their phenyl groups, excitation at a wavelength below 400 nm can result in an increase of over 150 fold in fluorescent emission upon the binding of DNA to the homodimer as opposed to the 6 fold increase seen when the samples are excited at 493 nm.

Two other homodimeric ethidium bromide compounds (EthD-1 and EthD-2) are commercially available from Molecular Probes, Inc. (Eugene, Oreg.). However, in contrast to the results with meta-EthD, the discrimination between bound and unbound dye was not substantially changed by exciting at wavelengths below 400 nm. It should be pointed out that although meta-EthD, EthD-1 and EthD-2 are all ethidium bromide dimers, they are chemically dissimilar. As shown in (FIG. 2), meta-EthD is comprised of two phenanthridinium rings linked together through the meta position of the phenyl rings through amide bonds. In contrast, the phenanthridinium rings of EthD-1 and EthD-2 dimers are joined together through the nitrogen of the center rings rather than through the phenyl rings. The intervening chain is comprised of an alkyl chain with two amine attachment groups which are secondary in EthD-1 and methylated to give the quaternary salts for EthD-2. The inability of the EthD-1 and EthD-2 compounds to exhibit the same results seen with meta-EthD demonstrates that the method of the present invention was not a predictable property of ethidium dimers per se.

The method of the present invention may find use in many methods that had been previously described for ethidium bromide, ethidium bromide homodimers and other intercalators. Of especial use, is the application of the present method towards real time analysis of nucleic acid amplification and probes labeled with meta-EthD. The large increase in fluorescence after illumination at wavelengths under 400 nm will allow a better signal to noise ratio than previous methods. Thereby, the present invention should enjoy a higher sensitivity of detection of the synthesis of nucleic acids during such amplification procedures.

In previous art, ethidum bromide has also been modified through the center ring by attaching other intercalators (U.S. Pat. No. 5,646,264) and fragments of intercalators (U.S. Pat. Nos. 5,582,984 and 5,599,932) for improved performance of binding to double-stranded DNA. Modification groups similar to those disclosed in U.S. Pat. No. 5,582,984 have also been added to the central ring of ethidium bromide to improve performance with RNA (U.S. Pat. No. 5,730,849). In light of the results with the meta-EthD, it is disclosed that the modifications in U.S. Pat. Nos. 5,646,264; 5,582,984; 5,599,932; and 5,730,849; all of which are incorporated by reference, may also be used to synthesize novel compounds by replacing the center ring with the phenyl ring as an attachment site. These may also be used in many of the applications previously described for ethidum bromide, ethidium bromide dimers, ethidum bromide heterodimers, modified ethidium bromide compositions and other intercalators.

9. Novel Chemiluminescent Reagents

In another embodiment of the present invention, novel 1,2-dioxetanes compounds are disclosed that when used as substrates for selected enzymes result in an intramolecular reaction between two groups attached to different sites of an aromatic ring thereby leading to chemiluminescent signal generation. In another aspect of the present invention, the novel 1,2-dioxetanes compounds are disclosed that are substrates for modification enzymes rather than degradative enzymes where the modification event can lead to chemiluminescent signal generation.

a. Enzyme Dependent Interactions Between Two Groups Attached to Different Sites on a Cyclic Ring In another aspect of the present invention, novel 1,2-dioxetane reagents are disclosed that comprise two groups attached to different sites of a cyclic ring where after catalysis by an appropriate enzyme, the reagent undergoes an intramolecular reaction thereby leading to chemiluminescent signal generation. The reagents of this aspect of the present invention have the structure:

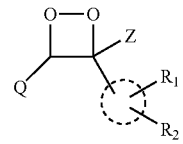

where Q comprises a cycloalkyl or polycycloalkyl group located on one side of the dioxetane and R1 and R2 are located on different sites of a cyclic ring that is bonded to the other side of the 1,2-dioxetane. Z can comprise hydrogen, alkyl, aryl, alkaryl, heteroalkyl, heteroaryl, cycloalkyl, or cycloheteroalkyl groups. In a preferred embodiment, Q comprises an adamantyl group. In another preferred embodiment, the two sites where R1 and R2 are attached are adjacent to each other on an aromatic ring. R1 comprises a chemical group that is a substrate for an enzymatic activity. In the presence of the appropriate enzyme, R1 is catalytically converted into R1* which comprises a chemically reactive group G1. R2 is attached to the ring through an oxygen atom and comprises a chemical group G2 that is capable of interacting with the G1 group that is produced by the conversion of R1 into R1*. Due to the rigidity imparted by the ring, G1 is in close proximity to G2 thereby endowing the interaction to take place with favorable kinetics. This interaction leads to formation of an unstable dioxetane thereby producing chemiluminescence.

R2 can comprise an aliphatic group, substituted aliphatic group, an aromatic group or any combination of the foregoing. In the cases where R2 comprises a substituted aliphatic group, the substituents can be halogens, nitrate, sulfur or nitrite. The aliphatic group can be substituted at one position or in several positions. The substituents at each position can be the same or different.

As described above, after the enzymatic conversion of R1 into R1*, a chemically reactive group G1 is formed. Chemically reactive atoms that may find use as part of G1 may include but not be limited to nitrogen, sulfur or oxygen. Enzymes that may find use with present invention can include but not be limited to amidases, esterases, acetylcholinesterases, acid and alkaline phosphatases, decarboxylases, lipases, glucosidase, xylosidase, fucosidase, trypsin and chymotrypsin. Enzymatic substrates that may find use as constituents of R1 can include but not be limited to amides, esters, phosphates, carboxylic acid, fatty acids, glucose, xylose, fucose or amino acids.

Although it is not essential, R1 can also be designed such that after the enzymatic conversion of R1 into R1* the interaction between G1 and G2 creates a 5 or 6 membered ring which is known to be an especially stable conformation. An example of formation of such an intermediate is shown below using oxygen as the connection of R2 to an aromatic ring:

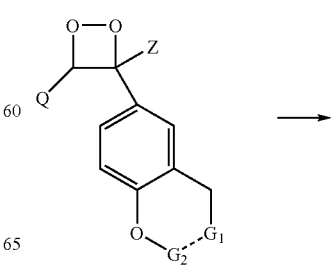

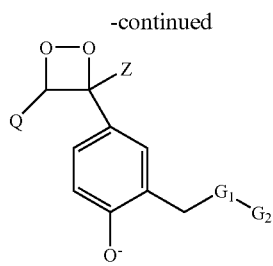

As shown above, the intermediate structure can undergo an internal substitution reaction that transfers the G2 group to the G1 group of the R1* moiety thereby releasing the oxygen and creating an unstable phenoxy ion leading to an unstable form of dioxetane and production of a chemiluminescent signal. The juxtaposition of the G1 and G2 groups caused by locating each group on a segment of a rigid structure should allow efficient interaction and subsequent substitutions and rearrangements to form the light producing intermediate after production of G1 by enzymatic activity.

b. Chemiluminescence Generation Derived from Modification Enzymes

In another aspect of the present invention novel 1,2-dioxetane derivatives are disclosed in which the triggering event that leads to the decomposition and production of chemiluminescent signal is an enzyme modification of a specific group of the structure. This is in direct contrast to previous examples in which the triggering event is the cleavage of a substituent. In a preferred mode, the modification of the substitutent is dependent upon an enzymatic reaction. An example of such a composition is given below:

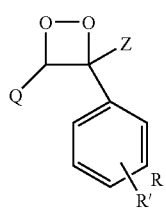

In the diagram above, Q and Z are defined as described previously and R can comprise a chain of atoms consisting of C, N, O, S or any other atoms required. R can also comprise saturated or unsaturated groups. Furthermore, R' can include but is not limited to alcohols or carboxylic groups. The modification reaction that can lead to light production reaction can include but not be limited to oxidation and reductions. Enzymes that can be used in this aspect of the present invention can include but not be limited to oxidases and reductases.

A representative example of this process is given below where a dioxetane derivative comprising a terminal alcohol is enzymatically converted to an aldehyde by the action of alcohol dehydrogenase.

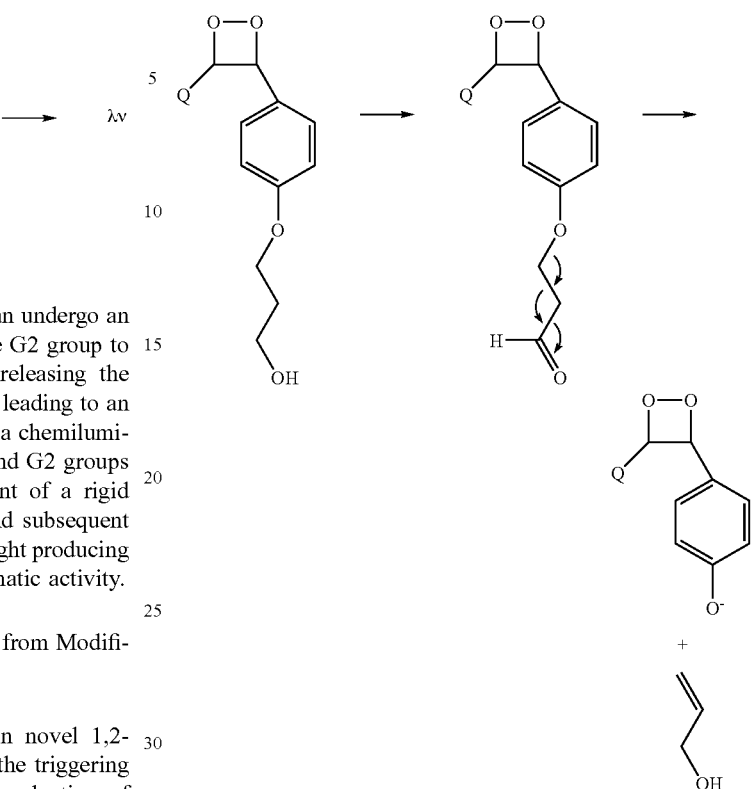

This resulting product can then undergo β elimination that then results in the unstable phenoxide ion that triggers the decomposition of the 1,2-dioxetane resulting in the chemiluminescent signal.

10. Real-Time Signal Generation

The present invention discloses a method of signal generation that can be used for labeling either discrete nucleic acids or a library of multiple sequences. The present invention provides methods and compositions for specifically labeling analytes of interest in the presence of other nucleic acid sequences. The present invention may also be used for the detection of the presence and/or amount of nucleic acids of interest during the course of using such nucleic acids as templates for further nucleic acid synthesis. This can be carried out either by post-synthesis analysis or real-time analysis during the course of such synthesis. In the present invention, nucleic acids are synthesized that comprise at least one first element of an energy transfer pair and at least one second element of an energy transfer pair. When a first energy transfer element is capable of acting as an energy donor, the second energy transfer element is capable of acting as an energy transfer acceptor. Conversely, the first element can be an energy transfer acceptor and the second element can be an energy donor. This second element comes into association with the first element by virtue of either being incorporated into the same nucleic acid strand that comprises a first element or by binding to a nucleic acid strand. In the absence of nucleic acid synthesis or a binding event, there is little or no energy transfer from the donor to the acceptor. However, by the appropriate designs, the present invention allows energy transfer from a donor to an acceptor during or after nucleic acid synthesis.

Various embodiments of the present invention use labeled primers, probes, nucleotides, nucleic acid binding agents and solid supports as sources of energy transfer elements. In the present invention, a probe and a primer share the common characteristic of binding to complementary sequences with the proviso that a primer has the additional property of being able to be extended. Nucleic acid constructs may also be used in the present invention as primers, probes or templates. In the present invention a nucleic acid construct comprises a nucleic acid with sequences that are either identical or complementary to all or a portion of a nucleic acid of interest and may further comprise at least one non-natural or artificial element.

Examples of non-natural or artificial elements that could comprise a nucleic acid construct can include but not be limited to promoter sequences, capture sequences, identity tag sequences, consensus sequences, protein binding sequences, artificial primer binding sequences, modified nucleotides, nucleotide analogues, abasic sites, labels, ligands, peptides and proteins. Furthermore nucleic acid constructs may comprise analytes. These analytes can be individual specific sequences or a library of sequences. They may be the original analyte itself or a copy thereof. They can be derived from chromosomes, episomes or fragments thereof. Examples of episomes can include but not be limited to plasmids, mitochondrial DNA, chloroplast DNA and viruses.

a. Energy Transfer Between Labeled Primers

In one embodiment of the present invention, the first and second energy transfer elements are components of at least two primers or nucleic acid constructs that can be extended in the presence of appropriate nucleic acids. At least one of these primers or nucleic acid constructs will comprise sequences that are complementary to sequences that are present in a portion of a nucleic acid of interest. At least one other primer or nucleic acid construct will comprise sequences that are identical to sequences that are present in another portion of the nucleic acid of interest. In this way, a nucleic acid of interest can be used as a template for binding and extension of the primer or nucleic acid constructs. Separation or displacement of the extended primer from the target allows the target strand to be used for another primer binding/extension event. In addition the extended primer can itself be used for a primer binding/extension event. Thus one would create a product that comprises two extended primers hybridized to each other. In this aspect of the present invention, the primers used for the preceding sequential primer binding/extension events comprise either a first energy transfer element or a second energy transfer element. If the primers in each strand are in sufficient proximity to each other, they would be capable of allowing an energy transfer event from a donor to an acceptor. This process can be used to create a double-stranded labeled nucleic acid. Of especial utility for diagnostic purposes, the extent of the signal generated by this process can be used to identify the presence and quantity of the particular nucleic acids used as templates.

The amount of signal can also be increased by introduction of amplification processes. For instance, the use of a primer for each strand of a desirable nucleic acid target is the basis of many target amplification procedures where strand extension of each primer generates templates for further synthetic events. These methods can depend upon discrete steps such as those employed in PCR (U.S. Pat. No. 4,683,202) or they can be continuous isothermal methods such as SDA (U.S. Pat. Nos. 5,270,184 and 5,455,166) and Loop Mediated Amplification (U.S. patent application Ser. No. 09/104,067; and European Patent Application No. EP 0 971 039 A) (all the foregoing incorporated by reference). Thus, although the present invention can be used for post-synthesis assessment of the amount of synthesis of appropriate nucleic acids, it can also be used during the multiple synthetic steps that take place during the course of amplification, i.e. real time analysis. Amplification can be carried out under the same conditions used in the absence of labeled primers or an additional step can be included that can increase the efficiency or selectivity of signal generation. For instance, for real time analysis of an isothermal reaction, monitoring can take place continuously or at chosen intervals. In the latter method, an extra step can be carried out where either a sample is removed for analysis or a thermal step is introduced that promotes signal generation or reading at a particular state but does not substantially interfere with the continuation of the reaction.

In previous art, the design of primer locations for double stranded synthetic nucleic acid products for diagnostic purposes has been to have the primers for each strand located sufficiently apart that additional sequences are incorporated in between them that can be used for hybridization with probes or characterization by restriction enzymes. Thus, the sequences of double stranded synthetic nucleic acid products would be derived from two sources. First, there would be intrinsic sequences derived from the primers and their complements. These will be present independent of what particular target segment was used as a template. Secondly, there would be the sequences between the primer segments. These would be totally dependent upon the nature of the particular nucleic acid segment used as a template for nucleic acid synthesis. Depending upon the nature of the design of the primers, the conditions of the reaction and the particular nucleic acid sequences in the sample used in the amplification reaction, only a particular desirable sequence may be synthesized or other non-desirable sequences may also be synthesized. For diagnostic purposes, the segments between the primers have then been used as a target for a labeled probe to generate a signal that would be dependent upon the presence and amount of only the desirable sequences.

In this particular embodiment of the present invention, the requirement for extended sequences between the primer segments is abrogated since probes are not used for the detection of the amplification product. In fact, the present invention discloses that a proximity between the primers at each end of an amplicon is a desirable arrangement that can be used for a novel means of signal generation. By including a first element into a primer for one target strand and a second element into a primer for the complementary target strand, proximity of these two primers in a double stranded amplicon allows energy transfer to take place from the element that acts as a donor to the element that acts as an acceptor even though each element is on a different strand.

As described previously, various amplification systems that are based upon a series of primer extension reactions that result in double stranded amplicons with incorporated primers will be able to enjoy this particular embodiment of the present invention. For instance, FIG. 3 shows potential amplification products for a) PCR and b) SDA. Details of the processes that can be used for these amplification methods can be seen in numerous publications including the original patent for each of these methods (Mullis et al. in U.S. Pat. No. 4,683,202 and Walker et al., in U.S. Pat. Nos. 5,270,184 and 5,455,166; incorporated herein by reference). Even though these methods employ different principles, the presence of a labeled primer or nucleic acid construct in each strand of an a double-stranded nucleic acid allows the use of the present invention. In addition, other methods that have been previously disclosed may find use with the present invention including multiprimer amplification (U.S. patent application Ser. Nos. 08/182,621; filed Jan. 13, 1994; Ser. No. 09/302,816, filed Mar. 31, 1998; and Ser. No. 09/302,818, filed Feb. 3, 1998; and Ser. No. 09/302,817, filed Apr. 16, 1999) and amplification with inverted oligonucleotides (U.S. patent application Ser. No. 5,462,854) all of which are hereby incorporated by reference.

As described previously, this particular embodiment of the present invention depends upon a proximity between the primers or nucleic acid constructs on each strand. In terms of an extended strand made from a first primer or nucleic acid construct, this can also be described as the proximity between the segment derived from the incorporated first primer or nucleic acid construct and the segment that can be used as a binding site for the second primer or nucleic acid construct to synthesize the complementary strand. For instance, proximity can be achieved by having these two segments being immediately adjacent to each other on an extended strand. In such a case, the nucleic acid sequences of the extended strands would be entirely derived from the sequences of the primers or nucleic acid construct and their complements. To depict this more clearly, an arbitrary sequence is shown in FIG. 4 with potential primer arrangements that could be used in the present invention. In FIG. 4(A) the sequences chosen for primers are immediately adjacent to each other on each strand. Alternatively, there can be a gap between the primer segment and the primer binding segment on one strand as long as there is sufficient proximity for energy transfer between the donors and acceptors in the amplification product. An example of a longer spacing using the same target sequence is shown in FIG. 4(B).

It should also be noted that in addition to allowing a novel system of signal generation, the reduction of the amplicon size such that it comprises little more than primer binding regions should confer advantages over the more traditional longer amplicons. These should include shorter extension times, sharper melting points, and overall higher efficiency in each round of amplification since the amount of synthesis is of a minimal nature. Also, the choice of appropriate energy transfer elements and detection systems can allow multiplex amplification to monitor more than one target sequence.

In the presence of the appropriate target sequences, signal generation should increase as more labeled primers become incorporated into double-stranded nucleic acids. This signal generation should be specific and proportional to the presence of appropriate target molecules in the sample. Thus, in the absence of nucleic acid synthesis, there should be little or no energy transfer between donor and acceptor molecules since each element is located on a separate primer or nucleic acid construct. Secondly, signal generation can be carried out under reaction conditions that allow little or no nucleic acid synthesis in the absence of appropriate target templates. One way that this can be carried out is by appropriate design of the primers themselves such that primer-dimer formation is minimized, for instance by selecting primer sequences that have no overlap between their 3' ends. On the other hand, if non-target nucleic acids are present that have sequences present which have some similarity to the primer binding sequences, nucleic acid synthesis may take place, but the nucleic acid product is unlikely to have the primers incorporated into the appropriate lengths for energy transfer to take place. Another way that target-specific signal generation can be increased is by the use of what has been termed "nested PCR". In this method, the majority of amplification is carried out by a second set of primers that flank the labeled primers. This is shown in FIG. 3(C). The labeled primers can be present in reduced amounts, require different annealing conditions or be used in separate short amplification reactions. This should reduce the involvement of the labeled primers in amplification of either primer-dimers or non-target sequences. In this particular instance, it may even be possible to successfully generate target dependent signals with labeled primers or nucleic acid constructs that have some degree of overlap between their 3' ends. Lastly, target independent products should have a different length and/or base composition thereby allowing a differentiation between target specific double-stranded nucleic acids and inappropriate products by their thermal profiles. As described previously, this profile can be obtained as part of the process or a separate step may be introduced to obtain such a profile.

Although this particular embodiment of the present invention has been described in terms of incorporation of nucleotides, there are also means for extending primers that depend upon the addition of polynucleotides rather than individual nucleotides. As such, two of these methods, LCR (U.S. Pat. No. 5,494,810) and GAP-LCR (U.S. Pat. No. 6,004,286), may also enjoy the benefits of the present invention. These methods depend upon the use of two sets of adjacent oligonucleotides where each set is complementary to one particular strand of a target nucleic acid. In the present invention, a first energy transfer element will be in one or more oligonucleotides complementary to one strand and a second energy transfer will be in one or more oligonucleotides complementary to the other strand. An illustration of the use of the present invention with this method is shown in FIG. 3(D).

b. Energy Transfer Between a Labeled Primer and Nucleotide(s)

In another embodiment of the present invention, one or more primers or nucleic acid constructs that comprise a first energy transfer element are used in conjunction with at least one nucleotide that comprises a second energy transfer element. After target template directed addition of nucleotides to the primer or nucleic acid construct, energy transfer can then take place by interaction between a first energy transfer element in one primer or nucleic acid construct and a second energy transfer elements in an incorporated nucleotide. The labeled primer or nucleic acid construct and the labeled nucleotide or nucleotides can be on the same strand if only a single primer or nucleic acid construct is used during primer extension events. Linear amplification can also be carried out where the primer or nucleic acid construct is used for successive rounds of binding/extension events.

On the other hand as described previously, the inclusion of one or more primers or nucleic acid constructs that can use the extended primers or extended nucleic acid constructs as templates can allow further synthesis. In this case, the second energy transfer elements that are introduced by nucleotide incorporation can be in both the extended strand and its complementary copy. FIG. 5 shows potential amplification products made by various amplification processes that illustrate this particular embodiment of the present invention. In FIGS. 5(A), 5(B) and 5(C), one or more of the primers used for amplification contain an energy transfer element. Although this Figure shows the acceptor element (A) being present in primers and the donor elements (D)

being present in the nucleotides incorporated during amplification, the opposite arrangement may also be used. In this particular aspect of the present invention, the spacing between the primers can be of any desired length that is appropriate for carrying out the amplification.

As described previously, various methods may be employed to selectively generate signal from only appropriate targets. These can include primer design, thermal profiling of double-stranded nucleic acids and nested amplification. This particular embodiment of the present invention is also amenable to multiplex formats. For instance, if various primers are used such that more than one extended primer species is synthesized, they can be distinguished from each other by using a common energy transfer donor in the nucleotides and different energy transfer acceptors in each of the primers. Each of the individual nucleic acid products can then be identified by the spectral characteristics of the acceptor on the primer.

Previous art has described the dual use of both a primer that comprises a first energy transfer element and a dideoxyribonucleotide that comprises a second energy transfer element (Kwok and Chen U.S. Pat. No. 5,945,283). The present invention differs from this art in using nucleotides that are not strand terminators in the reaction mix thereby a) allowing for the possibility of multiple incorporation events and b) allowing sufficient synthesis that the extended strand could be used as a template for synthesis of a complementary nucleic acid if desired.

c. Energy Transfer Between Labeled Nucleotides

In another embodiment of the present invention, it is disclosed that signal generation can take place during synthesis with labeled nucleotides only. In this particular embodiment, synthesis is carried out in the presence of at least one nucleotide that comprises a first energy transfer element and at least one nucleotide that comprises a second energy transfer element. The nucleotides that comprise first and second energy transfer elements may be the same nucleotide, for instance by using a mixture of dUTP, where some are labeled with an energy transfer donor and some are labeled with an energy transfer acceptor. On the other hand, they may be different nucleotides, for instance by using a mixture that has dUTP labeled with an energy transfer donor and dCTP labeled with an energy transfer acceptor.

As described above, incorporation of nucleotides that comprise first and second energy transfer elements can take place during a single round of strand extension, multiple rounds of extension of one strand for linear amplification, or by the provision of at least one second primer or nucleic acid construct for exponential amplification. FIG. 5(D) shows a PCR amplification product where both donors and acceptors have been incorporated through labeled nucleotides. In the absence of incorporation, there will be little or no energy transfer between one nucleotide to another. However, once they have been incorporated into nucleic acid strands, they are in position to be able to allow energy transfer to take place. This can be through intrastrand interactions in the same strand or through interstrand interactons between nucleotides on complementary strands. A particular nucleotide base may consist entirely of labeled nucleotide or there may be a mixture of labeled and unlabeled nucleotides.

Although methods such as PCR and SDA produce double-stranded amplicons as their major product, there are systems such as NASBA that alternate between double-stranded DNA and single-stranded RNA forms. In these amplification methods, the present invention finds use by providing either energy transfer labeled deoxyribonucleotides for labeling the DNA or energy transfer labeled ribonucleotides for labeling RNA products. In the latter case the presence of both donor-labeled and acceptor-labeled ribonucleotides in the RNA strands would allow intrastrand energy transfer. As described previously, various methods may be employed to selectively generate signal only from appropriate amplicons. These can include primer design, thermal profiling of double-stranded amplicons and nested amplification. Additionally, since signal generation in this particular embodiment of the present invention is derived from the energy transfer between incorporated nucleotides, the method described, by Singer and Haugland (U.S. Pat. No. 6,323,337 B1) can also be used where the primers comprise energy quenchers. Quenchers that may be used for this purpose can include non-fluorescent derivatives of fluorescein, rhodamine, rhodol or triarylylmethane dyes as described by Singer and Haugland (op. cit.).

d. Energy Transfer Between a Fluorescent Intercalator and a Labeled Primer or Nucleotide(s)

The previous embodiments of the present invention have utilized primers and nucleotides as energy transfer elements. Another embodiment of the present invention discloses that nucleic acid binding agents can be used as energy transfer elements after strand extension. It has previously been described in U.S. Pat. No. 4,868,103 that energy transfer can be used in a hybridization assay that involves a labeled probe and an intercalator. In contrast to this art, a labeled primer or nucleic acid construct with a first energy transfer element is extended to synthesize nucleic acids that can be bound by a nucleic acid binding agent that comprises a second energy transfer element and is substantially sequence independent. Binding can take place while the extended strand is still base-paired with its template or after separation from the template i.e. the extended strand is in double-stranded or single-stranded form. The nucleic acid binding agent can be a protein or a chemical that has a high affinity for nucleic acids. An example of proteins that may find use with the present invention may include but not be limited to T4 gene 32 protein, SSB protein, histones and antibodies. The T4 gene 32 protein and SSB protein have affinities for single-stranded nucleic acids and the histones have an affinity for double-stranded nucleic acids. Antibodies specific for nucleic acids and for RNA/DNA hybrids have been described in the literature (U.S. Pat. Nos. 6,221,581 and 6,228,578). Methods for attaching fluorescent labels to proteins have been widely described in the art. An example of a chemical that has a preferential affinity for single strand nucleic acids can include but not be limited to SYBR™ Green II. An example of a chemical that has a preferential affinity for double-stranded nucleic acids can include but not be limited to intercalators. Examples of intercalators that may find use with the present invention can include but not be limited to Acridine, Ethidium Bromide, Ethidium Bromide Homodimers, SYBR™ Green I, TOTO™, YOYO™, BOBO™ and POPO™. The binding agent can comprise a energy transfer element directly or indirectly. Proteins labeled with an energy transfer element would be examples of indirect means. The intercalators listed above would be examples of direct means.

Also, energy transfer to or from nucleic acid binding agents can be carried out by labeled nucleotides instead of labeled primers if desired. When the nucleic acid is in double-stranded form, this embodiment of the present invention can take advantage of the ability of some intercalators to have enhanced fluorescence upon binding to double-stranded nucleic acids. As has been mentioned earlier, this effect has been used by itself to monitor real time nucleic acid synthesis during amplification reactions. However, when used alone, this method suffers from the amount of background exhibited by the dye alone or by dye binding to single-stranded primers. This deficiency may be overcome by the present invention since unbound dye should be unable to undergo an energy transfer interaction with unincorporated labeled nucleotides. As such, the present invention should enhance the selectivity of signal generation compared to using a labeled nucleic acid binding agent alone.

As described previously, various methods may be employed to selectively generate signal from only appropriate target molecules. These can include primer design, thermal profiling of double-stranded amplicons and nested amplification.

e. Energy Transfer Between a Labeled Probe and Nucleotide(s)

There may be circumstance where the specificity contributed by nucleic acid probes may desirable. Therefore, another aspect of the present invention, discloses novel means of signal generation where at least one nucleic acid probe that comprises a first energy transfer element is used in conjunction with either nucleotides that comprise second energy transfer elements. Previous art has described the use of an energy transfer labeled primer and an energy transfer labeled sequence specific probe (Wittwer et al. in U.S. Pat. No. 6,174,670). In contrast to this art, the present method is not constrained to the use of a probe that is in proximity to the primer alone but allows the use a probe designed to anneal to any location on the nucleic acid strand that is desirable. In addition, the present invention conveys the ability to use multiple energy transfer probes by using various segments of the extended nucleic acids as probe targets. Thus, when using nucleotides that comprise energy transfer elements, signal generation should take place after hybridization of labeled probes to the labeled nucleic acid strand.

For instance, after strand-extension, the separation or removal of the template strand can allow the binding of a probe to a single-stranded extended strand and thereby allowing energy transfer to take place between first energy transfer elements in the probe and second energy transfer elements that have been incorporated into the extended strand. Energy transfer to or from first elements in the probe can be derived from the segments that are hybridized to the probe, or if they are in sufficient proximity, they may be from adjacent single-stranded regions. Another illustrative example of the present invention makes use of loop-mediated amplification (U.S. patent application Ser. No. 09/104, 067; European Patent Application Publication No. EP 0 971 039 A). One of the structures generated by this system is a single-stranded loop adjacent to a double stranded stem. Therefore, as disclosed in the present invention, a probe can be bound to sequences in the loop region and undergo an energy transfer reaction with incorporated nucleotides.

In this embodiment of the present invention, specificity is generated by two factors. First, the strand extension events should be dependent upon the specificity of the primer binding/extension reactions themselves. Secondly, the probes are blocked at their 3' ends and only participate by binding to appropriate sequences when these are synthesized as a result of the primer extension reactions.

The various embodiments of the present invention that have been disclosed above can be used in homogeneous assay systems. However, there are also advantages that are offered by the use of solid supports with the present invention. Fixation to solid supports can take place prior to initiation of extension reactions, during strand extensions, and after completion of strand extensions. Examples of solid supports that may find use with the present invention can include but not be limited to beads, tubes, microtiter plates, glass slides, plastic slides, microchip arrays, wells and depressions. Fixation to the support can be carried out either directly or indirectly. As an example of indirect fixation, a capture agent may be attached to the solid support. This capture agent may be a nucleic acid with sequences that are complementary to sequences that are present in a primer, a nucleic acid construct, an analyte or a copy of an analyte thereby allowing fixation through hybridization . Another example of a capture agent could be an antibody that has an affinity for a nucleic acid. (U.S. Pat. Nos. 4,994,373; 4,894, 325; 5,288,609; 6,221,581 B1; and 6,228,578; all of which are incorporated by reference).

As an example of direct fixation, many of the previous embodiments employ a primer for strand extension. Therefore if desired, these primers could be covalently attached to a solid support prior to carrying out any extension reactions. In the presence of the appropriate nucleic acids, strand extension can then occur as described previously thereby resulting in strand extension products that are also directly attached to the solid support. First and second energy transfer elements can be in the primers fixed to the solid support and/or they can be in nucleotides, probes or nucleic acid binding agents as described in the various embodiments disclosed above. An illustrative example of this would be the use of amplification on a microarray as described in Rabbani et al., U.S. patent application Ser. No. 09/896,897, filed on Jun. 30, 2001 (incorporated by reference) with at least one set of primers at a locus comprising a first energy transfer element and nucleotides comprising second energy transfer elements. With the appropriate apparatus, each locus on the chip could then be separately monitored for the extent of synthesis during the course of the amplification. Another example of direct attachment would be the use of primers that comprise ligands and solid supports that comprise the appropriate ligand receptors. An illustrative example of this arrangement could be the use of poly T primers that have been labeled with biotin and using beads that are coated with avidin or strepavidin for fixation. Nucleotides that comprise first energy transfer elements can be incorporated into a cDNA copy made with the poly T primer and the complex of a cDNA bound to its RNA template can bind intercalators that comprise second energy transfer elements. In this example, attachment of the primers to the beads can take place before, during or after the strand extensions.

f. Solid Supports Comprising Energy Transfer Elements

Figure 6:
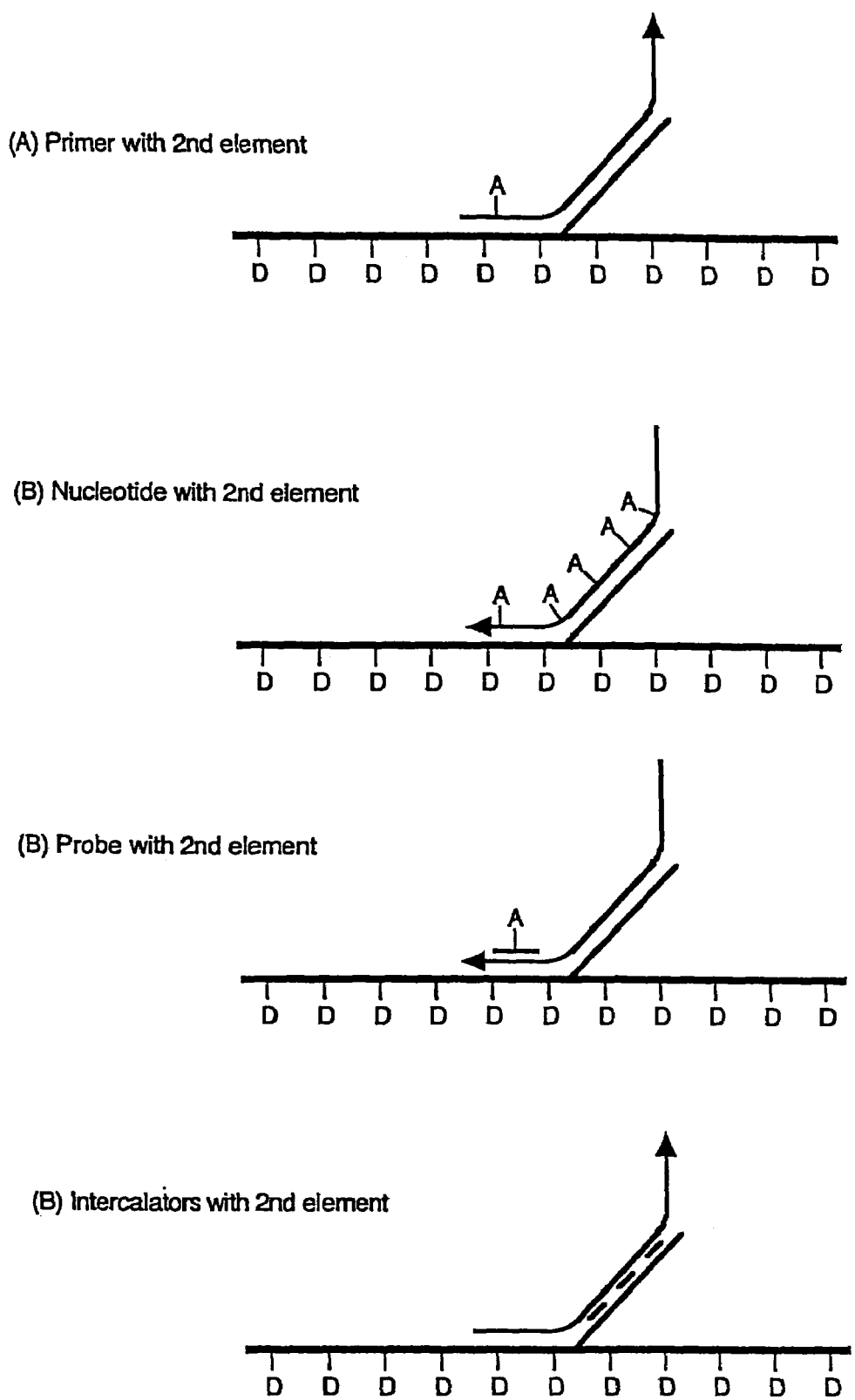
FIG. 6 shows the use of matrix with energy transfer elements.

In addition, a solid support is not relegated to only a passive role. In another embodiment of the present invention, a solid support comprises a first energy transfer element. Fixation of a nucleic acid to the support can then bring a second energy transfer element into sufficient proximity for a signal to be generated. In this embodiment of the present invention, the second energy transfer element can be part of a nucleotide, primer, probe or nucleic acid binding agent. As an illustrative example, a matrix is made with a selection of nucleic acid probes on an array. The matrix is then treated such that first energy transfer elements are fixed to the surface as well. In the presence of appropriate templates or analytes, synthesis of a group of nucleic acids with second energy transfer elements is then carried out as described previously. Hybridization of the labeled nucleic acids to the array brings the second energy elements into proximity with the surface bound first elements. Signal should then be generated by energy transfer that corresponds to the amount of nucleic acids that are bound to a particular locus on the array. An illustration of this principle as well as some of the other embodiments described previously is depicted in FIG. 6. Solid supports with capture elements can also be used in methods where no extension reactions are required. For instance, a solid support, a capture oligo or an antibody specific for nucleic acids can comprise a first element. Signal generation can then occur after binding of an unlabeled analyte in either single stranded or double stranded form to the support where the presence of the second element is dictated by the presence and amount of the analyte that becomes bound to the support. For instance, the second element can be part of the complex in the form of a probe or a nucleic acid binding agent.

g. Previous Processes (a Through f) Used for Labeling

Generation of signal from first and second energy transfer elements after target dependent strand synthesis can be used for the purpose of detecting the presence or amount of a nucleic acid of interest in a sample. When signal generation is dependent upon the specificity of the priming events, the procedures are carried out under conditions where target independent primer extension is minimized or as described previously, methods are included that can distinguish between target derived nucleic acids and spurious strand extension products. On the other hand, inclusion of a step that uses the discretionary power of nucleic acid hybridization can limit or even obviate the need for primer specificity. For example, an entire library of poly A mRNA sequences can be converted into a library of cDNA copies by the use of a universal poly T primer. The library of cDNA strands can then be indiscriminately used as templates for second strand synthesis. Inclusion of a promoter into either the first strand primer (U.S. Pat. No. 5,891,636) or second strand primer (Rabbani et al., U.S. patent application Ser. No. 09/896,897, filed on Jun. 30, 2001) (both documents incorporated by reference) allows synthesis of multiple RNA copies of each individual original mRNA. When either this product or a cDNA copy is labeled, hybridization with a microarray of nucleic acids can be used to determine the amounts of any particular species in the original sample. The present invention can be employed with such methods by including first and second energy transfer elements in primers, nucleotides, probes, nucleic acid binding agents or the matrix itself.

On the other hand, the nucleic acids of interest may be supplied by the user in known quantity and the embodiments of the various invention disclosed above may be used to synthesize labeled probes. For instance, a single purified species of a nucleic acid of interest might be provided as a template for labeling reactions with one or two primers. When a discrete group of varied nucleic acids is desired to be labeled, the primer sets can be expanded accordingly. Labeled probes can then be created by inclusion of first and second energy transfer elements by any of the means disclosed previously. These probes can then be used to identify the presence or quantity of unlabeled nucleic acids in samples in any of a variety of formats that are well known to those skilled in the art.

h. Analytes as Primer Extension Substrates

It should also be noted that the nucleic acids of interest or copies of the nucleic acids of interest may also be used directly in strand extension reactions either as substrates for terminal transferase addition, ligation or by acting as primers. For example, terminal transferase can be used for the template independent addition of first energy transfer elements onto the 3' ends of either individual nucleic acids or a library of nucleic acids. Second energy transfer elements can then be included as part of the terminal addition reaction or they can comprise primers, probes, nucleic acid binding agents or solid supports. In another illustrative example, restriction digestion. of DNA can be followed by terminal addition of a mixture of nucleotides with first and second energy transfer elements. Various individual species of nucleic acids can then be hybridized to various capture sequences on discrete loci of an array to measure the presence or amount of individual labeled sequences.

It is also a subject of the present invention that analytes or copies of analytes can be used as primers in template dependent labeling reactions. In this context, incorporation in itself may be used as an assay since template directed synthesis should be dependent upon the presence of discrete sequences in the analytes that correspond to their complements in appropriate hybridized templates. Thus a desired nucleic acid sequence can be specifically labeled in the presence of other nucleic acids that may be present in a mixture. Although at least one segment of the template is designed to match the desired analyte sequence, the segment of the template that is used direct the sequences added onto the analyte can be either a natural sequence or an arbitrary sequence.

As an illustrative example of this method, a library of polyA mRNA can be labeled in the presence of total RNA by using a probe that comprises a first segment that comprises Poly T and a second segment that can be used as a template. When bound to the poly A sequences of the mRNA through the first segment, the 3' end of the mRNA can be extended using the second segment as a template. The nucleotides that are incorporated using the second segment as a template can be either labeled or unlabeled. Examples of artificial sequences that may find use as second segments can include primer binding sites, RNA promoter sequences. Another illustrative example is a series of probes that comprise first segments complementary to the 3' ends of discrete bacterial RNA species. For each particular species-specific segment, a discrete template sequence can be used. After specific priming by the RNA present in a sample, evaluation can be carried out with an array that has capture sequences complementary to the extended sequences thereby separating out the individual extended RNAs. And lastly, cDNA copies can be made from a pool of mRNA using standard techniques. Each cDNA that represents a full copy of the original mRNA should have a discrete 3' end that represents the 5' end of the original mRNA. Template/Probes could then be used for each cDNA that is desired to be quantified. In these illustrative. examples of using an analyte as a primer in template dependent extensions, labeling may take place by incorporation of a single labeling species as described in previous art or the methods that have been disclosed above may be employed using first and second energy transfer elements.

11. Fragmentation and/or Incorporation of Desirable Nucleic Acid Segments a. Template Dependent Addition of Desirable Nucleic Acid Sequences to the Ends of Analytes It is another aspect of the invention to provide novel compositions and methods for the template dependent addition of desirable nucleic acid sequences to analyte or target nucleic acids. In prior art, poly A sequences have been relied upon as the basis for most methods of manipulation of mRNA. Furthermore, the utility of mRNA has derived from its use as a template to carry out any and all such manipulations. For instance, Poly A has been used as a primer binding site for making cDNA copies and carrying out linear or exponential amplification of mRNA. However, as described previously, this feature is not universally shared among all RNA targets. Furthermore, it is a selective feature for the 3' end of mRNA. In contrast to this art, the present invention overcomes the limited scope of analysis of nucleic acids by viewing and using an analyte or target nucleic acid not as a template but as a substrate for strand extension, i.e. as a primer. As such, the nucleic acid constructs that are provided for these processes are not used as primers but rather they serve as templates to enable analyte or target nucleic acids to incorporate any arbitrary sequence that is desired by the user. Such sequences can comprise promoters, primer binding sites or signal generating moieties.

In the present invention, methods that may be directed for use with nucleic acid analytes may also be used with any desirable nucleic acid target as well. Analytes can comprise single desirable sequences or they may be a library of various sequences. Analyte or target nucleic acids may be comprised of RNA or DNA as well as copies of RNA or DNA. The analyte or targets nucleic acids may be extracted from biological samples or they may have been produced in vitro. They may also have undergone procedures and processes such as digestion, fragmentation, amplification, extraction and separation.

The present invention discloses that the ends of nucleic acids can be hybridized to complementary chimeric nucleic acid constructs (CNACs) that comprise two segments. The first segment comprises nucleotides or nucleotide analogues that are capable of binding or hybridizing to the 3' ends of the analytes. The second segment comprises nucleotides or nucleotide analogues that can be used as a template for extension of the 3' end of the analyte. In contrast to prior art, methods are disclosed that do not rely upon the presence of a selected sequence such as a poly A segment at the ends of the anlyte, but rather the present invention discloses methods where any and all sequences that may be present at the 3' end of an analyte or library of analyte are sites for binding and template-dependent extension reactions. In the present invention, template-dependent strand extension can take place either by incorporation of individual nucleotides (polymerization) or by addition of pre-synthesized oligonucleotides (ligation). It should be pointed out that although the inventions are commonly described in terms of 3' extension since this is a characteristic of polymerase driven processes, when ligation is used instead, the 5' end is also a suitable substrate for template dependent strand extension. The ability to introduce arbitary nucleic acid sequences into the 3' end of a target or analyte nucleic acid provides a simple and powerful vehicle for transforming an analyte into a probe or a nucleic acid construct that could be used for further manipulations. A library of nucleic acids with various sequences can also be converted into a library with universal sequences that could be later used for further manipulation directly in a controlled and measured manner for signaling purposes, priming events, capture events or amplification events.

In one particular embodiment of the present invention, a set of CNACs is used where the first segment comprises all the potential permutations of nucleotide sequences. Thus, if the first segments of the set of CNACs comprise 6 variable nucleotides, the first nucleotide ($N_1$) can be G, A T or C, the second nucleotide ($N_2$) can be G, A T or C etc. and the set itself will comprise $4^6$ (4,096) different CNACs. In this sense, it has similarity to the use of random primers for synthesis of nucleic acid copies. However the present invention differs from random priming in that the CNACs are not extended themselves (i.e., act as primers) but provide complementary binding to the analytes such that the second segment of the CNAC can be used for template dependent extension of the analyte. For this purpose, it is preferred that the ends of the CNACs be blocked. Thus although the present invention uses random sequences, the side reaction of random primers using each other as primers and templates is completely avoided. The present invention also differs in that the binding of random primers to any particular site of an anlyte allows an extension event. In the present invention, it is only when the CNAC binds to a complementary sequence at the end of an analyte that an extension event takes place. Although, there will be random binding and disassociation of the CNACs at multiple sites on the analyte strands, this is not a true equilibrium situation since there is actually a dynamic favoring of binding to the ends. For instance, juxtaposition of a 3'OH in the analyte and a complementary CNAC can bind a polymerase and form a complex that would be more stable than a CNAC bound to an internal site. In addition to providing a longer half-life of binding of the CNAC to the terminus by complex formation, the complex generates an even more stable form by extending the analyte, thereby increasing the number of bases that are complimentarily base paired. This disequilibrium can be carried out in an isothermal reaction, or if preferred, the reaction temperature can be raised to promote dissociation of CNACs from non-productive binding sites followed by a return to the same reaction temperature to promote another round of binding of CNACs to analytes. If desired, these variable conditions can be recycled multiple times to optimize the amount of analyte ends that undergo template-dependent addition.

It is a further objective of the present invention to disclose novel compositions and methods that utilize CNACs synthesized with universal bases i.e., bases that can base pair with more than one complementary base. Nucleotides or nucleotide analogues that comprise universal bases can contribute stability without adding complexity. Therefore, in this aspect of the present invention, a novel CNAC is disclosed that comprises two segments as described above, but instead of using permutations of nucleotides, universal bases that lack sequence specificity are used in the first segment. For instance, an example was given above with a set of CNACs that comprised permutations in 6 positions thus requiring 4,096 different CNACs. By the use of universal bases, only a single CNAC species is required for providing template-dependent addition of desirable nucleic acid sequences to any analytes or set of analytes irrespective of the sequences at their ends. Since universal bases do not always display a complete lack of discrimination and the ability to bind to a particular nucleotide, it would be possible and even desirable to use a set of CNACs that comprise different universal bases or universal base analogs, or different mixtures of universal bases and universal base analogs. As described previously, this method can involve a self-selecting process where CNACs undergo a series of binding and dissociation events of the universal bases to random segments of the analytes until the CNAC binds to a 3' end. In this particular embodiment, base pairing at the end is not a problem since each CNAC possesses universal base pairing capability and productive extension should be mostly related to the relationship between the 3' end of the analyte and the second segment of the CNAC. Efficient strand extension can take place where the beginning of the second segment of the CNAC is aligned with the 3' end of the analyte such that the first base synthesized will be the complement of the first base of the second segment. On the other hand, universal bases also have some capacity for use as templates and as such, hybrids where the 3' end of the analyte is not perfectly adjacent to the junction between the first and second segments of the CNAC should also be able to carry out strand extension of the analyte.

It is a further objective of the present invention to disclose novel compositions and methods where CNACs comprise universal bases in combination with permutations of nucleotides. In this particular embodiment, the CNAC can be considered to comprise three different segments wherein a first segment comprises universal bases, a second segment represents permuted series of discrete nucleotides at one or more positions and the third segment comprises a nucleic acid that can be used as a template for extension of 3' ends. Thus the present invention should be able to enjoy the stability without complexity of the universal bases in the first segment in conjunction with selectivity and further stability contributed by specific base pairing by a permutational second segment anchor. Thus, if a universal base used in the first segment of a CNAC has approximately half of the binding affinity as a base pairing between normal nucleotides, a set of CNACs that comprised 4 variable nucleotide positions and 4 universal bases would have the same average Tm as random hexamers, but would require only $4^4$ or only 256 different CNACs. This is compared to the 4,096 different CNACs required with a hexamer permutational first segment. Similarly a CNAC with 4 universal bases and 6 variable positions would comprise 4,096 different CNACs but would have binding properties analagous to CNACs with random octamer first segments that would require $4^8$ permutations (i.e. 65,536 different CNACs).

Therefore, one would cover all possible permutational combinations that could exist in the terminal end of any analyte regardless of its derivation, while at the same time enjoying reasonably high binding efficiency and capabilities because the universal sequences in the first segment provide the additional binding stability without imposing any further specificity. Thus for the same number of CNAC molecules in a reaction mixture, there would effectively be a 16 times higher concentration of CNACs that could bind to a particular 3' end of an analyte in the examples cited above. This should provide superior kinetics and efficiency compared to CNACs with only permutational segments.

Universal bases, i.e., bases that can base pair with more than one complementary base, were first used in oligonucleotides to maintain stable hybridization with target nucleic acids that had ambiguity in the identity of their nucleotide sequence. A well-known example of this is the substitution of inosine in PCR primes (Liu and Nichols, (1994) Biotechniques 16; 24-26). Inosine has the property of being able to base pair efficiently with. either G, A, T or C in a complementary strand (Kawase et al., 1986, Nucl. Acids Res. 19; 7727-7736). The melting temperature is less than a normal base pairing but still higher than a mismatch. When used as a template, inosine is recognized as if it was effectively G and a C is preferentially incorporated into the complementary copy. Other analogs of nucleotides that can act as universal bases have also been described. For instance, 5-nitroindolenine and 3-nitopyrrole analogues have also been described as universal bases (Loakes and Brown, 1994, Nucl. Acids Res. 22; 4039-4043, Nichols et al., 1994, Nature 369; 492-493 both of which are incorporated by reference). The use of these and other universal bases are reviewed by Loakes (2001) in Nucl. Acids Res. 29; 2437-2447 (incorporated by reference). The ability of universal bases to add stability without adding to the complexity of primers has been described by Ball et al., (1998, Nucl. Acids Res. 26; 5225-5227, incorporated by reference) where the addition of 5-nitroindolenine residues at the 5' end, improved the specificity and signal intensity of octamer primers used for cycle sequencing. Thus, these and other universal bases may all find use in the present invention.

As described above, the present invention allows any nucleic acid or nucleic acid fragment to be used for template-dependent extension and obviates dependency upon poly A tails. The desirable nucleic acid (or nucleic acid of interest) that is incorporated into an analyte strand can transform any nucleic acid or nucleic acid fragment into a form that provides a primer binding sequence that can carry out functions previously enjoyed by polyadenylated nucleic acids. Linear amplification can be carried out by incorporating a promoter as the desirable nucleic acid (or nucleic acid of interest) in a CNAC and exponential amplification can be carried out with desirable primer binding nucleic acid sequences using any of the methods previously described for poly A targets. Additionally, it is contemplated that template-dependent incorporation of a nucleic acid into an analyte also presents the opportunity to directly label the analyte or analytes by using a labeled nucleotide or oligonucleotide in the incorporation step.

Research studies have had a focus on poly A mRNAs due to its accessability and convenience as a substrate. The present invention allows non-polyadenylated nucleic acids to be manipulated with the same ease of use previously accorded to poly, A mRNA. Thus, the present invention can be used with DNA, hnRNA, snRNA, tRNA, rRNA, bacterial mRNA or any RNA lacking a poly A sequence. Even poly A mRNA may find use with the present invention. The reliance upon the 3' poly A tail has led to a bias towards the information contained in this end. In most methods of prior art, sequences at the other end of mRNA were still dependent upon the efficiency with which a priming event at the 3' took place. Accordingly, any interruptions in the copying process or a scission between the 5' end and the poly A end reduced the amount of 5' sequences that were available for study or manipulation. Thus, even a single nick in a large mRNA molecules eliminated the use of the 5' end of the molecule and numerous reports and even commercial products are dedicated towards the preservation of the continuity between the 5' and 3' ends of mRNA during its isolation. Since the present invention discloses methods that are independent of poly A, fragments of poly A RNA that have become separated from the poly A region remain available for use and study.

In fact, such a fragmentation process can be advantageous since all segments of the poly mRNA can be independently and efficiently used with no bias derived from their relationship to the 3' end. This fragmentation will be especially useful for hnRNA which has remained an underutilized area of research. This neglect has stemmed from two characteristics of hnRNA: the lack of poly A as a handle and the very large average size. Although the introns that are present in hnRNa lack coding sequences for the final gene product, there are likely to be a large number of sequences that do not appear in the final product that are important in control, regulation and interaction with other genes and gene products. The present invention will allow the sequences present in hnRNA to be as completely accessible as the polyA mRNA sequences had been previously.

Although many of the embodiments of the present invention are described in terms of RNA analytes, it should be pointed out that many of these processes can easily be applied to DNA fragments as well. Methods that can be used for the fragmentation processes described above can be physical or enzymatic. Physical means can encompass any chemical process as well as mechanical shearing and sonication. Enzymatic processes for fragmentation that may find use with the present invention can include but not be limited to endoucleases such as S1 nuclease, mung bean nuclease, RNase, DNase and restriction enzymes. It is a further point of the present invention that analytes can be treated with phosphatases if required, to provide an extendable 3' end. The CNAC of the present invention can comprise DNA, RNA or any combination thereof and the nucleotides may be modified or unmodified as desired. The CNACs may comprise standard nucleotides or they may comprise nucleotide analogs, sugar analogs and phophate analogs. Examples of each of these are peptide nucleic acids (PNAs), arabinosides and phosphorothioate linkages.

b. CNAC for Site Specific Fragmentation

The utility of universal bases to providing stability without adding complexity finds application in other processes as well. Another aspect of the present invention discloses compositions and methods for controlled fragmentation of an analyte or library of analytes. A novel CNAC is disclosed that comprises two segments, a first segment that comprises universal nucleotides to provide non-specific binding and a second segment with a discrete selected sequence that will generate a complex that provides endonucleolytic digestion. Under appropriate hybridization conditions, the CNAC will create an endonuclease susceptible site at each location in the analyte that is sufficiently complementary to the second segment of the CNAC. The size and nature of the selected sequence will determine the average spacing between endonuclease sites and therefore the particular average size of fragments. For example, a CNAC that comprises. a second segment with 4 or more deoxyribonucleotides should form a complex that is a substrate for RNase H. This should lead to a scission at each site in the analyte that is complementary to the second segment. On average, a given 4 base sequence should appear about every 250 bases. A smaller size distribution can also be obtained by the use of more than one CNAC thereby increasing the number of potential digestion sites. If preferred, a larger second segment can be used and hybridization/digestion conditions applied such that the complex is formed at more infrequent intervals and hence a larger average distribution in fragment sizes. Specificity may also be increased by the addition of discrete bases in either the first or third segments and using conditions such that stable hybrids are only formed with stability generated by proper base pairing of these bases as well.

The same method can also be applied to digestion of single-stranded DNA. The second segment of a CNAC can be designed with a recognition site for a restriction enzyme. Since most restriction sites are only 4 to 6 bases, the presence of the universal bases in the CNAC should provide a much more stable hybrid than using a 4 to 6 base segment alone. Although in this particular embodiment of the present invention, the second segment is used for fragmentation, it may also be used as a template for strand extension for incorporation of a desirable nucleic acid sequence into a fragmented analyte after endonucleolytic digestion. As described previously, this can provide a means for template-dependnent incorporation of a labeled nucleotide or oligonucleotide to label the analyte fragments at their terminus.

If preferred, the CNAC disclosed above can further comprise a third segment. For instance, the third segment can comprise another set of universal bases flanking the other side of the discrete bases in the second segment. This CNAC could be represented by the formula "$U_n$-$D_p$-$U_q$" where the "n" represents the number of universal bases in the first segment, "p" represents the number of discrete bases in the second segment and "q' represents the number of universal bases in the third segment. The additional third segment can provide additional stability or it may make the hybridized second segment a more efficient enzyme substrate for endonucleolytic digestion. Alternatively, the first and second are as described above and the third segment is a discrete nucleic acid sequence that provides a template for incorporation of one or more labels or a desirable nucleic acid sequence as described previously. Since the universal bases allow for indiscriminate binding, the reactions can take place under conditions where only hybridization events that include proper alignment with the discrete bases in a CNAC form stable hybrids between the CNAC and the analyte. Alternatively, thermocycling can be carried out to dissociate CNACs that are non-productively bound and allow additional binding events that lead to site-specific fragmentation until substantially all of the desired sites on the analyte have been digested.

c. CNACs for Digestion/extension

In another aspect of the present invention, novel CNACs are disclosed that comprise at least two segments where the first segment is complementary to a first analyte nucleic acid sequence and the second segment is complementary to a second analyte nucleic acid sequence. The CNAC is designed such that after mixing it with. an analyte nucleic acid, hybridization of a first segment to a first analyte nucleic acid sequence forms a first complex that is resistant to a particular endonuclease, while hybridization of a second segment to a second analyte nucleic acid sequence forms a second complex that is a substrate for the endonuclease. Furthermore, the second complex is capable of asymmetric cleavage such that only the analyte strand is subject to nicking or removal of nucleotides by the endonuclease. This treatment generates a new 3' end in the analyte strand that can then be used for the template dependent addition of nucleotides or oligonucleotides to the analyte strand.

The CNAC may further comprise a third segment that may or may not be complementary to a third analyte nucleic acid sequence. The third segment of a CNAC is distinguished from a second segment in that a third segment does not generate a third complex that is sensitive to endonucleolytic digestion. When the third segment is not complementary to the third analyte nucleic acid sequence, a third complex is never formed. On the other hand, when the third segment is complementary to a third analyte nucleic acid sequence, a third complex is formed, but endonuclease resistance is endowed by any of the means that can be employed to render a first complex resistant. After endonuclease digestion, the sequences in the second and third segments may act as templates for strand extension from a 3' end that has been generated by action of the endonuclease. The strand extension may be carried out by a template-dependent polymerizing enzyme (DNA polymerase or reverse transcriptase), or a template dependent ligation enzyme (DNA ligase). Fragments generated by endonuclease digestion may be further be subjected to kinase or phosphatase treatment, in order to add or remove phosphate groups at the 3' or 5' end as may be desired.

Analytes that may find use in the present invention can be either be DNA or RNA depending upon the nature of the CNAC and the endonuclease. Sequences in the analytes that may be used in the present invention may be discrete individual sequences, consensus sequences, or generic sequences that are present in all or most of a library of analytes. Examples of RNA that may find use with the present invention can include but not be limited to hnRNA, rRNA, mRNA, tRNA, or snRNA. Examples of DNA that may find use with the present invention can include but not be limited to chromosomal, single-stranded, plasmid, viral, bacterial DNA. Digestion of the second complex can be carried out by endonucleases such as RNase H and restriction enzymes. Prior to hybridization with the CNAC, the target nucleic acid or analyte nucleic acid may also have undergone pre-treatments including, digestion, fragmentation, extraction and separation. These fragmentation pre-treatments can include physical means, such as shearing, sonication or chemical treatment. Pre-treatments may also include endonuclease or exonuclease digestions. Examples of endonucleases that might find use in the present invention for pre-treatment can include but not be limited to S1 nuclease, mung bean nuclease, restriction enzymes, DNAse, ribonuclease H and other RNases.

The various segments of chimeric nucleic acid construct polymer may be comprised of the same or different backbones. For example, a first segment of a CNAC can comprise oligo-ribonucleotides and the second segment can comprise oligo-deoxyribonucleotides. Generally, the sugar-phosphate backbone may comprise a natural element, such as phosphate, ribose, or deoxyribose, or it may comprise analogs of phosphates such as phosphorothioates, or analogs of sugars such as. arabinosides. If desired, the 3' or 5' end of a CNAC may be blocked to prevent it from acting as a primer or from participating in ligation. The segments of a CNAC may further be comprised of a synthetic backbone, such as a polypeptide. Any synthetic polymer can be used as backbone as long as bases can be added in the proper orientation so that base pairing can take place. A prominent example of such a synthetic polymer that has this capability and usefulness is a peptide nucleic acid (PNA). The bases may be comprised of natural purine and pyrimidine bases as well as modified versions thereof. The bases may also comprise analogs of natural bases. For instance, the universal bases discussed previously may also find use in this embodiment of the present invention. Different segments of a CNAC may comprise the same or different backbones and comprise any base structures or elements, depending on the desirable function. Thus, one can construct a desired CNAC from the various components and elements provided above. The particular choice of components will depend upon the nature of the analyte and the endonuclease to be used.

For example, if the analyte is an RNA molecule, RNase H can be used as the endonuclease when the backbone of the first segment comprises an oligo-ribonucleotide and the backbone of the second segment comprises oligo-deoxyribonucleotides. Consequently, hybridization of the first segment to an RNA analyte creates a double-stranded RNA first complex that is resistant to ribonucleaseH and an RNA-DNA second complex which is a substrate for Rnase H activity. Treatment with RNase H would asymmetrically cleave all or some of the portion of the RNA analyte involved in the second complex but leave the RNA-RNA hybrid of the first complex and the second segment of the CNAC intact. As described above, a CNAC may also comprise a third segment. In the example above, if the third segment is complementary to the RNA analyte, the third segment may also comprise an oligo-ribonucleotide such that hybridization to the analyte forms an RNA-RNA hybrid that is resistant to the action of RNase H. Alternatively as described above, the third segment is not complementary to the RNA analyte and no hybrid is formed.

The choice of the particular endonuclease used to carry out this aspect of the present invention depends upon a number of factors. The primary factor is the nature of the analyte since the endonuclease must be able to utilize the analyte as a substrate for nicking or removal of nucleotides. Secondly, the endonuclease must allow circumstances where such nicking or removal is substantially asymmetric and takes place in the analyte strand. Thirdly, the endonuclease must allow circumstances where a first or third complex can remain substantially resistant to the action of the endonuclease. Lastly, the endonuclease must have sufficient specificity that it acts only upon the portion of an analyte that participates in formation of a second complex with the CNAC. It can be seen that the illustrative example with RNase H described above fulfills all of these criteria.

Another illustrative example would be to utilize an endonuclease that intrinsically provides an asymmetric cleavage. For example, digestion of double stranded DNA with the restriction enzyme N.BstNB I results in a nick in only one strand 4 bases downstream from the recognition sequence 5' GAGTC 3'. Thus, one could design the second segment of a chimeric nucleic acid construct with an oligo-deoxyribonucleotide sequence that is complementary to this sequence and a first segment that is complementary to sequences that are adjacent to the binding site for the second segment. In such a manner, when a second complex is formed by hybridizing the CNAC to the analyte, the double-stranded DNA is a substrate for this specific restriction enzyme and only the analyte sequence will undergo cleavage. As described previously, the CNAC can comprise a third segment that can serve as a template for introduction of a novel nucleic acid sequence by addition to the 3' end of the nick created by the endonuclease digestion. This example also serves as an illustration that a CNAC can still be considered "chimeric" even when it is a chemically homogeneous molecule. For instance, the CNAC above can be synthesized with three segments that comprise only oligo-deoxyribonucleic acids. In the present invention, this would still be a chimeric molecule since each segment has a different functional property, i.e., the first segment provides complementary base pairing and stability; the second segment provides for endonuclease susceptibility and the third segment provides a template for strand extension. This method may also be combined with other embodiments of the present invention that have been disclosed previously. For instance, a CNAC with two segments can comprise universal bases with specific nucleotides only in the sites that are required for recognition and digestion by the asymmetric endonuclease described above.

Another illustrative example of how this aspect of the present invention could be carried out would be by the use of an artificial or synthetic second segment where the constituents are modified or comprise analogs. Any such modification or analog may be used for this purpose as long as a) they allow hybridization to occur between the second segment and the analyte b) hybridization with the analyte forms a complex that is susceptible to endonuclease digestion and c) the second segment remains substantially resistant to the action of the endonuclease. For example, a second segment could comprise phosphorothioate linkages between bases. It has previously been shown that when a restriction enzyme site in a double stranded molecule comprises an unmodified segment and a phosphorothioate segment, only the unmodified segment undergoes a cleavage event (U.S. Pat. Nos. 5,270,184 and 5,455,166; incorporated herein by reference). Thus a CNAC with one or more phosphorothioate linkages in a restriction enzyme sequence in a second segment can be hybridized to a complementary segment of an analyte and only the analyte strand should be subject to endonuclease digestion.

Generally, the third segment may contain any arbitrary sequence segment, either related or non-related to a target nucleic acid. The third segment provides a template upon which the cleaved target nucleic acid or the analyte can act as a primer and thereby allow the introduction of any desirable nucleic acid sequence into an analyte. Through such a template dependent sequence introduction to an analyte, a signaling moiety or other elements such as primer binding sequences can be introduced directly to an analyte. Furthermore, through such a method, universal sequences could be introduced to an analyte nucleic acid that could act at a later stage as a template for the introduction of a universal primer or primer directed promoter system to prepare copies of the analytes as described in U.S. Pat. No. 5,891,636 and Rabbani et al., in U.S. patent application Ser. No. 09/896,897; both of which are incorporated by reference. The fact that nucleic acid fragments can be converted to such a construct through such a method could provide for an even amplification of nucleic acid libraries without prejudice to 3' end sequences. Further, such a sequence or sequences could be used for priming or capturing events directly or after amplification. Optionally, if endonuclease cleavage does not leave free 3'-OH in the remaining analyte, then the remaining analyte could be treated with phosphatase so that a 3'-OH is generated which can facilitate a priming event. Washing, melting or separation steps can be employed when and where desirable. Generally, with a chimeric nucleic acid construct with three sequence segments, one can introduce at will desired nucleic acid sequences at any location into an analyte nucleic acid sequence, including any possible internal sequence sites.

The various teachings in the present invention allows introduction of desirable specific sequences in a template directed manner into an analyte and thus empowering the analyte or set of analytes with diverse properties and capabilities including: acting as a probe; as a template; as a primer. The CNAC and/or an analyte labeled by means of a CNAC can be directly or indirectly immobilized onto a solid support which may include: tubes, cuvettes, plates, microtiter wells, beads, magnetic beads, and chips. Methods and compositions for carrying out this particular embodiment are described in U.S. Pat. Nos. 4,994,373; 4,894,325; 5,288,609; and 6,221,581 B1; 5,578,832; and 5,849,480 (all of which are incorporated by reference). This immobilization can take place either before or after strand extension and labeling of an analyte. For instance, such capabilities could be used in nucleic acid array analysis, in which instead of probing the analyte, the analyte acts as a primer on a matrix comprising an array of CNACs that can provide templates for strand extension of diverse analytes. Depending upon the particular embodiment of the present invention, hybridized analytes may be extended directly or undergo an endonuclease step prior to extension. One or more labels or signaling moieties could be incorporated directly or indirectly with such an array to indicate a specific hybridization of analytes to a site on the array.

d. CNAC for Partial Removal of Homopolymeric Sequences

Another aspect of the present invention discloses novel compositions and methods for the partial removal of a homopolymer sequence. Homopolymeric sequences are naturally present in poly A messenger RNA and are artificially present in many methods used for cloning. An example of the latter is poly C and poly G tailing of double-stranded cDNA molecules (Okayama and Berg, 1982 Mol. Cell. Biol. 2;161). Although the presence of these homopolymeric tracts provide beneficial effects for universal primer binding and cloning, only a small segment is usually necessary and the presence of large segments may actually be problematic. For instance, in a transcription template made from a cDNA copy of mRNA, long homopolymeric segments may induce premature terminations.

As such, the present invention discloses a CNAC that comprises two segments. The first segment is complementary to a chosen homopolymeric sequence and is designed such that a complex formed between the homopolymeric sequence and the first segment forms a first complex that is resistant to the action of a particular endonuclease. The second segment also comprises a sequence complementary to the homopolymeric sequence, but forms a second complex-that allows endonuclease digestion of the homopolymer. Thus although each of the segments comprise sequences complementary to the same target sequence, they differ in the properties they will confer after hybridization.

For instance, a CNAC that comprises a first segment made of rU and a second segment comprised of dT can hybridize to any segment of a polyA tail of mRNA. Digestion with RNase H will only eliminate poly A segments hybridized to the second segment. The CNAC can be recycled multiple times either by using thermal cycling or a temperature where the hybridization through a first segment or a segment alone is insufficient for stable hybridization. For instance, a CNAC that is comprised of 10 rU and 10 dT bases would be able to efficiently hybridize to a 20 base poly A segment at 37° C. Elimination of rA bases in this segment through RNAse H activity should destabilize the CNAC, enabling it to bind to a new segment. This process should continue until the mRNA molecules have has less than 20 rA bases left at their 3' ends. The remaining small poly A segment can then be used as a primer binding site by using appropriate hybridization conditions. If the CNAC or a DNA primer containing olgo T is used for this purpose, it is preferred that the RNase H activity used for the digestion be eliminated prior to priming.

The CNAC described above for generating resistant and sensitive complexes is meant only to exemplify the present invention and other sizes may be used for first and second segments. For instance, a deoxyribonucleotide segment of four bases have been shown to be sufficient for forming complexes that are substrates for Rnase H activity. The size of the segments of the CNAC should be designed such that there is efficient complex formation prior to endonuclease digestion and a sufficient portion of the homopolymeric target remains intact under the condition used for endonuclease digestion.

Furthermore, the CNACs of the present invention can comprise a third segment that may or may not be complementary to the homopolymeric target sequence. As described previously, if the third segment is complementary, the nature of the endonuclease and third segment is such that a third complex remains resistant to digestion by the endonuclease. The third segment can be homopolymeric or heteropolymeric depending upon its intended purpose. The nucleotides in the various segments of the CNAC may be comprised of natural bases or analogs thereof, universal bases or combination thereof that may provide either a weaker or strengthened hybrid formation with a desired sequence. For instance, the use of universal bases in a third segment can allow synthesis of a complementary segment that has a weaker than normal binding. Thus, if the new segment on the analyte is desired to be used as a primer binding site, a primer with normal base that were complementary to the primer binding site would have a competitive edge over re-annealing by the universal bases in the CNAC.

It will be readily appreciated by those skilled in the art that any of the compositions, solid supports, reagents, dyes, primers, nucleic acid constructs, and the like, can be formulated as kits, which can be employed for carrying out any of the processes described or claimed herein, and variations of such processes. For example, kits can be formulated as protein or nucleic acid labeling kits, nucleic acid processing kits, kits for incorporating desired nucleic acid sequences, amplification kits for amplifying targets, analytes and even a library of analytes. Post-synthetic and real time amplification kits can also be formulated from the compositions, solid supports, reagents, dyes, primers; nucleic acid constructs, and the like.

The following examples are offered by way of illustration and not by way of limitation to the present invention.

DESCRIPTION OF THE PREFERRED EMBODIMENTS

Example 1

Preparation of Cy 3 Labeling Reagent (a) Preparation of Compound I (2,3,3-Trimethylindolinium 5-Sulfone)

P-Hydrazinobenzenesulfonic acid (250 g) was mixed with glacial acetic acid (750 ml) and 3-methyl-2-butanone (420 ml) and heated at reflux for 3 hr. The solution was poured into a 2 L beaker and allowed to cool overnight. The resultant suspension was filtered, washed with acetic acid and lyophilized to remove residual acetic acid. The resultant solid was dissolved in methanol (1.5 L) and a saturated solution of potassium hydroxide in 2-propanol (900 ml) was slowly added. The color of the solution turned progressively lighter as the potassium salt of 2,3,3-trimethylindolinium 5-sulfone precipitated. The precipitate was filtered by suction, washed with 2-propanol and lyophilized to dryness to give 238 g of Compound I.

(b) Preparation of Compound II (1-Ethyl-2,3,3-Trimethylindolenineninium 5-Sulfone)

A portion (78 g) of Compound I synthesized in step (a) was suspended in 1,2-dichlorobenzene (700 ml). Ethyl iodide (250 ml) was added and the mixture was heated at 90-100 C. for 12 hr while stirring. The mixture was poured into 3 L of a 1:1 mixture of ethylacetate/ether and stirred for 2 hours. The resulting precipitate was filtered, washed with a 1:1 mixture of ethylacetate/ether and air-dried to give 68 g of product, Compound II.

(c) Preparation of Compound III (6-Bromohexanoyl Allyl Amide)

6-Bromohexanoic acid (20 g) and N-hydroxysuccinimide (15 g) were dissolved in 200 ml of anhydrous dimethylformamide (DMF). Dicyclohexylcarbiimide (22 g) in anhydrous DMF (50 ml) was added and the mixture was left at room temperature overnight. The precipitated urea was removed by filtration and the DMF solution containing the product, N-hydroxysuccinimide-6-bromohexanoate, was cooled to −10 to −20° C. An equimolar amount of allylamine in $H_2O$ (11 ml) was first brought to pH 8-9 with glacial acetic acid and then added slowly with stirring to the active ester. Solid sodium bicarbonate (10 g) was added slowly to avoid excessive foaming and the mixture was left without covering until the temperature was raised to −10° C. in two hr. The mixture was poured into $H_2O$ (1 L) and the product was extracted twice with chloroform (300 ml). The extracts were washed once with 1 N HCl in $H_2O$, once with 5% $NaHCO_3$ (300 ml) and three times with 10% NaCl in water. The chloroform phase was dried by addition of solid $MgSO_4$ and leaving it overnight under stirring. The chloroform was removed by evaporation under vacuum leaving a liquid that was used without any further purification for the next step.

(d) Preparation of Compound IV (Addition of Linker Arm to Compound III)

Compound I (11 g) from step (a) and Compound III (15 g) from step (c) were dissolved together in 1,2-dichlorobenzene (100 ml) and heated at 110° C. for 12 hours while stirring under argon. The mixture was slowly poured into ethylacetate a 1:1 mixture of ethylacetate/ether (700 ml) and after 30 minutes the solid precipitate was filtered, washed with a 1:1 mixture of ethylacetate/ether, air-dried and set aside. A glassy solid that was formed at the bottom of the flask was crushed in a mortar, triturated with a 1:1 mixture of ethylacetate/ether, filtered, washed with 2-propanol, dried in vacuum and combined with the precipitate from above to give Compound IV which was used without any further purification.

(e) Synthesis of Cy 3 Labeling Reagent (Compound V)

A portion of Compound II (12 g) from step (b) and N,N'-diphenylformamidine (10 g) in acetic acid (60 ml) were heated at 100-110° C. for 90 min with stirring. During the reaction the absorption at 286 nm and 415 nm was measured. The ratio of 415/286 increased during the first 60 minutes then remained constant at 2.2 for the next 20 minutes. After 90 minutes, the hot mixture was poured slowly into 700 ml of a 1:1 mixture of ethylacetate/ether. The resultant solid precipitate was collected with a pressure filter funnel, washed with 1:1 mixture of ethylacetate/ether and dried by passing argon through the cake. The precipitate was collected from the pressure filter funnel and slowly added to a mixture of 6.5 g of Compound IV from step (d), 50 ml of pyridine and 50 ml of acetic anhydride. The progress of the reaction was monitored by the decrease of absorbance at 385 nm and an increase in absorbance at 550 nm. The reaction was carried out overnight under stirring at room temperature. The absorbance at 550 nm increased with time followed by a drop in absorbance as the product precipitated out of solution. At the end of the reaction, the brown precipitate was collected and put aside. The liquid portion was treated by the addition of a seven-fold volume of ethylacetate. The precipitate that formed was collected and combined with the first precipitate. Since pyridine would interfere with a later palladium catalyzed step, any remaining pyridine was removed by dissolving the combined precipitate in 100 ml of 0.5M Triethylammonium carbonate, pH 8.0 (TEAC). The TEAC was then removed by evaporation under vacuum leaving a solid pellet. This product (Compound V) was then dissolved in $H_2O$ and kept at −70° C. until ready to be used.

Example 2

Preparation of Cy 5 Labeling Reagent (Compound VI)

Compound II (8 g) from step (b) of Example 1 and malonyl aldehyde dianil hydrochloride (10 g) were dissolved in 100 ml of a 1:1 mixture of glacial acetic acid and acetic anhydride followed by heating at 110° C. for two hours. The mixture was slowly poured into 500 ml of a 1:1 mixture of ethylacetate/ether and the precipitate was filtered, washed with a 1:1 mixture of ethylacetate/ether and dried by argon as above. The precipitate was then slowly added to a mixture of 12 g of Compound IV dissolved in 150 ml of a 1:1 mixture of pyridine/acetic anhydride while stirring. The mixture was transferred to an oil bath maintained at 90-100° C. for 30 minutes while continuing to stir. If desired, this step could have been extended up to 90 minutes. The reaction mixture was then cooled to room temperature and the precipitate was processed further as described previously for the Cy 3 labeling reagent in Example 1.

Example 3

Attachment of Cy 3 (Compound V) to dUTP

Mercurated dUTP (30 umoles) prepared as described in U.S. Pat. No. 5,449,767 was dissolved in 1 ml of 1M Lithium acetate and the Cy 3 labeling reagent (60 umol, 0.6 ml) prepared in Example 1 (Compound V) was added with stirring. Potassium tetrachloropaladate (30 umol in 0.5 ml $H_2O$) was added under argon. The reaction was monitored by HPLC and was complete after 1 hr at 40° C. Overnight incubation did not increase the yields. Four volumes of acetone were added to the reaction mixture and left overnight at −20° C. The next day, the precipitate was collected by centrifugation.

The pellet was dissolved in 0.1M Lithium acetate (pH 4) and loaded onto a DEAE Sephadex $A_{25}$ column. The column was developed by passing through a linear gradient of 0.1-0.7 M LiCl in 0.1M Lithium acetate. The fractions were examined by HPLC and the fractions which contained a single late peak were collected and set aside. Another group of fractions exhibited two peaks: the late peak described above and an earlier peak. These fractions were combined, adjusted to 0.1M LiCl, reloaded onto a DEAE Sephadex $A_{25}$ column and refractionated as above. Again the fractions containing a single late peak were collected and set aside. Although it was not done in this example, the fractions that contained two peaks after the second chromatography could have been combined and put onto the column another time to increase the yield of the single peak product. The fractions that had exhibited a single late peak by HPLC were combined together and the $H_2O$ was removed by evaporation in vacuum. The last traces of $H_2O$ were removed by resuspension of the semi-solid residue in 50 ml of 100% ethanol followed by evaporation. The alcohol step was repeated once more. The residue was resuspended in 30 ml of ethanol and 1 ml of 3M lithium acetate was added. The solution was mixed well and left overnight at −20° C. to facilitate complete precipitation of the Triphosphate. The precipitate was collected by centrifugation, redissolved in $H_2O$ and partially lyophilized to remove remnants of the ethanol. The amount of product was measured by absorbance at 550 nm and a molar extinction value of 150,000. The solution was then readjusted to a stock concentration of 10 mM and stored at −70° C.

Although the procedure above describes the preparation of Cy3 labeled dUTP, the same steps could be carried out for the preparation of Cy 5 labeled dUTP by the substitution of the Cy5 labeling reagent (Compound VI from Example 2) instead of the Cy3 labeling reagent (Compound V from Example 1) used in the example above.

Example 4

Preparation of a Labeled Nucleotide with a Rigid Arm Linker and an Aphenylic TAMRA Analogue (a) Preparation of Compound VII (3,6-Bis-(Dimethylamino)-Xanthene-9-Propionic Acid)

Figure 7:
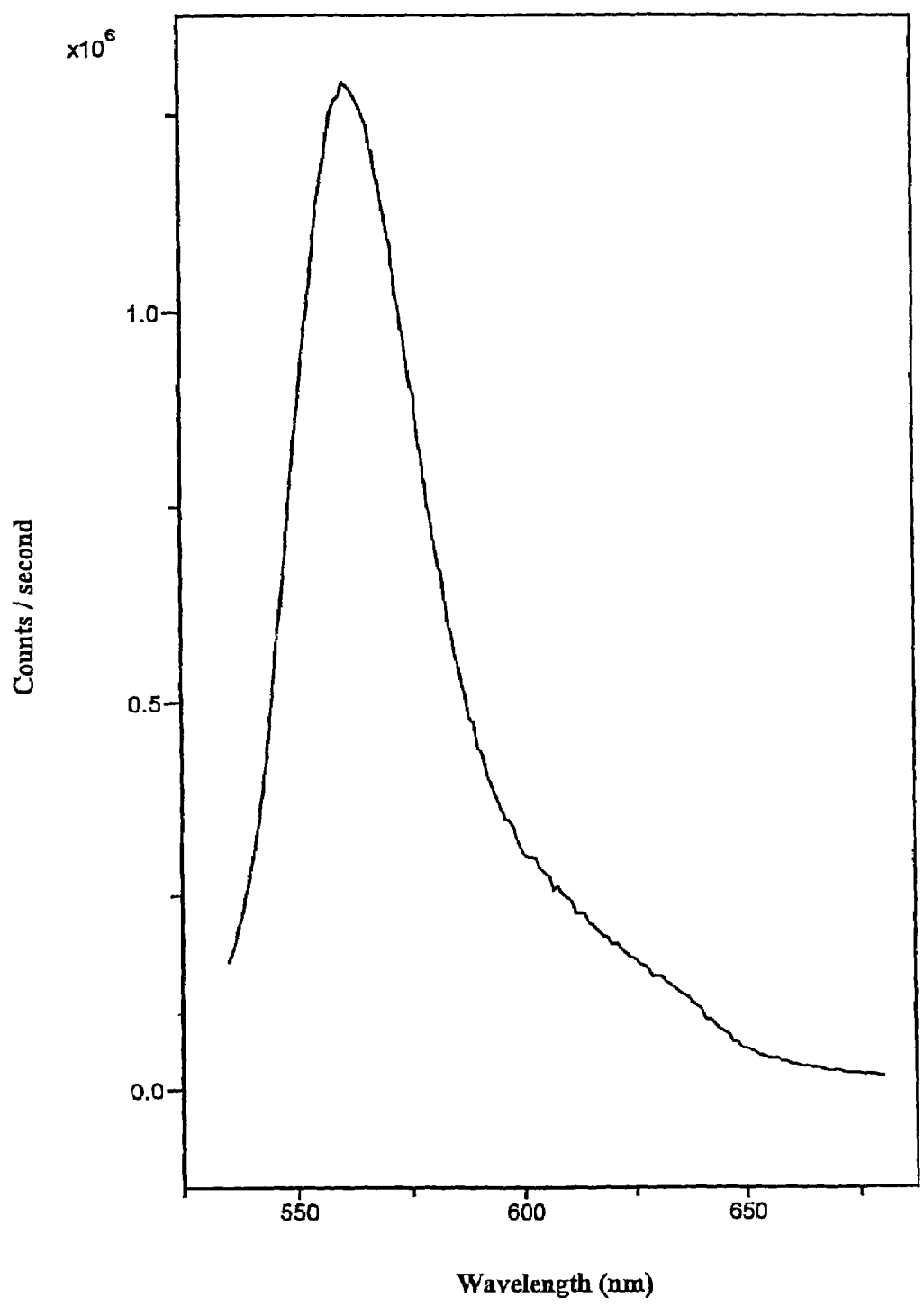
FIG. 7 is the spectrum of aphenylic analog of TAMRA.

3-(Dimethylamino)phenol (5.8 g) was mixed with succinic anhydride (2.1 g) and heated at 120° C. for 90 minutes with stirring under argon. The mixture was cooled, $H_2O$ (80 ml) was added and the mixture was heated at reflux for 10 minutes. The water phase was discarded, leaving behind a dark brown gummy material. This substance was dissolved by the addition of $H_2O$ followed by an adjustment to pH 10 with 1M NaOH while stirring. The pH of the clear solution was then brought down to 2 by the addition of 1M HCl. The dye was salted out by the addition of NaCl to a final concentration of 2.5 M. The precipitate was filtered, washed with NaCl (2.5 M) and dried by lyophilization to give 1.2 g of Compound VII. The fluorescence spectrum of Compound VII is shown in FIG. 7.

(b) Preparation of Compound VIII (Active Ester of Compound VII)

Compound VII from step (a) was dissolved in chloroform (200 ml) and N-hydroxysuccinimide (1.5 g) was added with stirring. After the N-hydroxysuccinimide went into solution, 1-ethyl-3-(3-dimethylaminopropyl) carbodiimide (2 g) was added and the mixture was stirred overnight in the dark. The mixture was extracted with $H_2O$ (80 mL) and the chloroform phase containing Compound VIII was dried with anhydrous magnesium sulfate and stored at −20° C.

(c) Preparation of Compound IX (Free Acid Form of Glycerlyglycine)

13 g of glycylglycine was suspended in a mixture of an equimolar amount of triethylamine in 300 ml of anhydrous methanol and mixed with a 1.5 molar excess of methyltrifluoro acetic ester. The suspension was refluxed until a homogeneous solution was achieved. The methanol was removed by rotary evaporation and the residue was suspended in 100 ml of $H_2O$. The pH was then adjusted to 10.0 to allow the trifluoroglycerylglycine to go into solution. The pH was then brought down to 1-2 with Hydrochloric acid whereupon the free acid form of the trifluoroglycerylglycine precipitated out of solution. This mixture was left overnight at 4° C. to allow complete precipitation of the product. The next day, the precipitate (Compound IX) was collected by filtration and then dried.

(d) Preparation of Compound X (NHS Ester of Glycerylglycine)

15 g of Compound IX from step (c) was dissolved in 100 ml of DMF and a 2 fold molar excess of N-hydroxysuccinimide was added under stirring. A 1.1 fold molar excess of dicyclohexylcarbodiimide dissolved in 10 ml of DMF was then added and the mixture was left overnight at room temperature to produce the NHS ester (Compound X).

(e) Preparation of Compound XI (dUTP with Glycylglycine Linker)

10 uMoles of allylamine dUTP were. dissolved in 0.5 ml of 0.3M $NaHCO_3$ followed by addition of 15 uMoles of Compound X from step (d) and incubation at room temperature for 2 hours to form Compound XI. LiAc was then added to a final concentration of 0.5M and the nucleotide product (Compound XI) was precipitated by addition of 5 volumes of ethanol and leaving the solution overnight at −20° C. The amine was deprotected by dissolving the precipitate in 1 M LiOH for 1 hour at room temperature. The solution was neutralized with glacial acetic acid in the cold and the Triphosphate was precipitated with ethanol as above.

(f) Preparation of Compound XII (dUTP with Tetraglycyl Linker)

Compound XI from step (e) was further treated by repeating step (e) to add an additional glycylglycine linker unit thereby forming 5'-allylamido-(tetraglycyl) amine dUTP (Compound XII). The amine was deprotected and the Triphosphate precipitated as described above in step (e).

(g) Preparation of Compound XIII (Attachment of Aphenylic TAMRA Analogue to dUTP)

20 umoles of Compound XII from step (f) was dissolved in 2 ml of $NaHCO_3$ (0.3M) and LiCl (0.7 M) and cooled on ice. The active ester of the dye (40 umoles) in chloroform from step (b) (Compound VIII) was dried in vacuum and dissolved in DMF (2 ml). This solution was then added to the ice cold dUTP solution and the mixture was stirred in the dark overnight at room temperature. The mixture was diluted with 20 ml water and loaded onto a DEAE-Sephadex $A_{24}$ (20 ml) column at 4° C. The column was washed with TEAC (0.1 M, pH 7.8, 50 ml) and the product was eluted with a linear gradient of 0.1-0.8 M TEAC, pH 7.8. The fractions that were pure by HPLC were combined. The TEAC was removed in vacuum by repeated evacuations following the addition of water. The residue was dissolved in lithium acetate (4 M) and precipitated with 4 volumes of absolute ethanol, then dissolved in water and stored at −70 to give 13.6 mg of Compound XIII.

It should be noted that the example cited above used a tetraglycyl rigid arm linker. The same methods that were described above could have been used to synthesize compounds with other lengths. For instance, compound XII (dUTP with tetraglycyl arm) from step (f) could have been manipulated further by a repetition of step (e) and adding another glycylglycine unit therby creating a hexaglycyl arm. Similarly, the activation steps described for preparation of glycylglycine (steps c and d) could also been carried out with glycine as the starting material thereby allowing addition of single glycyl units.

Example 5

Preparation of a Labeled Nucleotide with a Rigid Linker Arm and an Aphenylic Texas Red Analogue (a) Preparation of Compound XIV (3,6-Bis-Julolidinoxanthen-9-Propionic Acid)

Figure 8:
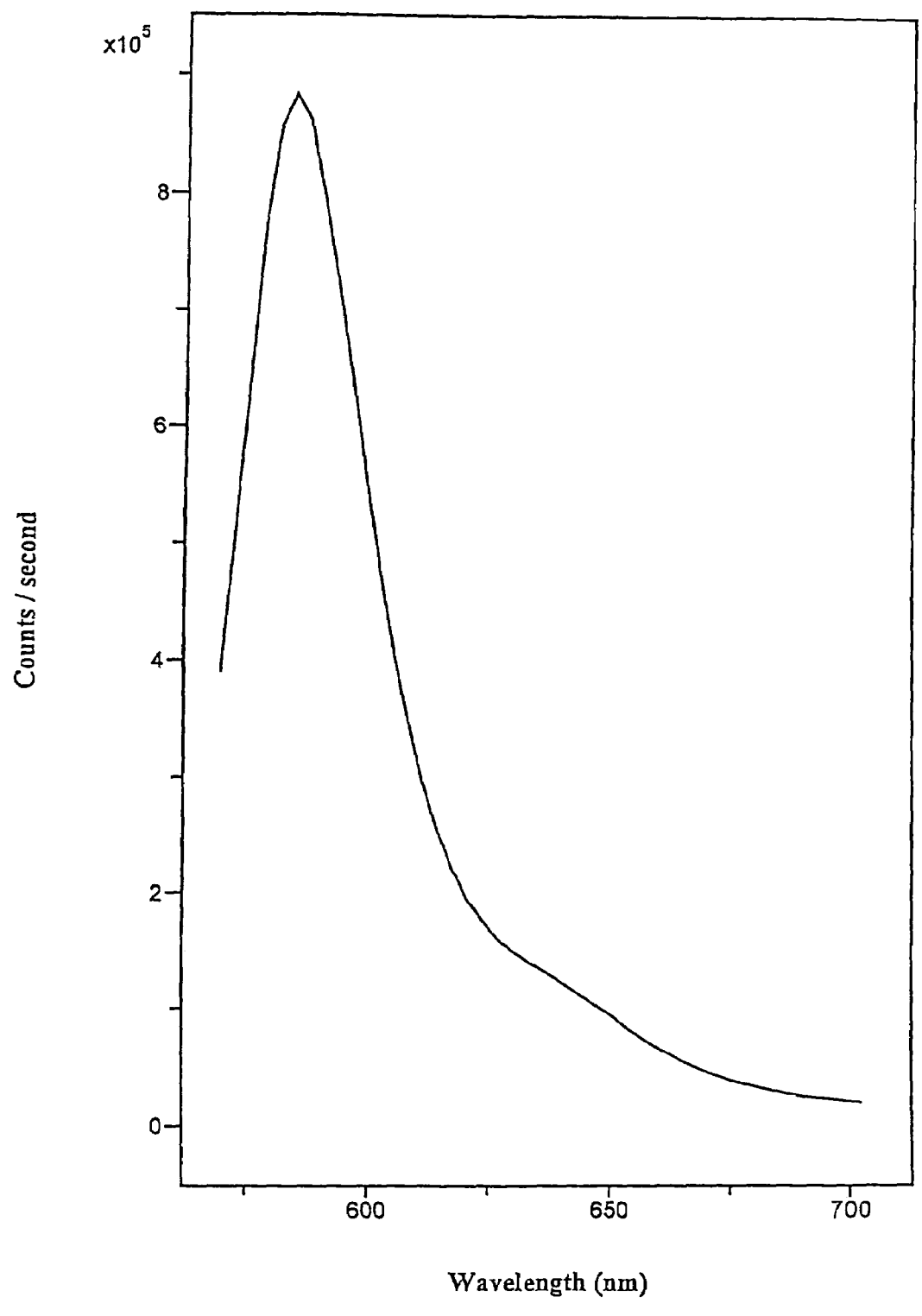
FIG. 8 is the spectrum of aphenylic analog of Texas Red.

8-Hydroxyjulolidine (10 g) and succinic anhydride (2.6 g) were combined under argon and heated at 130° C. for 2 hours with stirring. The mixture was cooled, H$_2$O (150 ml) was added and the mixture was refluxed for 15 minutes and then cooled. The water layer was discarded and the glassy dark brown residue was dissolved by the addition of H$_2$O followed by an adjustment to pH 10 with 1M NaOH while stirring. The pH of the solution was then brought down to 2 by the addition of 1M HCl at which point the product precipitated again. The mixture was centrifuged, the supernatant was discarded and the pellet was washed by suspending it in water and recentrifuging, The pellet was then lyophilized to give 3.6 g of product (Compound XIV). The fluorescent spectrum of Compound XIV is shown in FIG. 8.

(b) Attachment of Label to a Nucleotide

Subsequent steps for the preparation of the active ester of Compound XIV and attachment to dUTP with a rigid linker arm were carried out as described in Example 4.

Example 6

Preparation of Cyanine Dyes with a Rigid Linker Arm (a) Preparation of Compound XV [(2,3,3, Trimethyl-3-H-indol-5-yl) Acetic Acid]

110 g of 4-Hydrazinobenzoic acid were mixed with 450 ml of glacial acetic acid and 250 ml of 3-methyl-2-butanone under stirring. The mixture was heated at 128° C.-130° C. for 6 hours and left to cool overnight at room temperature. The glacial acetic acid and 3-methyl-2-butanone were removed under vacuum and the solid was triturated with 300 ml H$_2$O, filtered and washed again with 300 ml H$_2$O. The cake was subsequently dried under vacuum. The solid was then recrystalized from ethyl acetate resulting in Compound XV.

(b) Preparation of Compound XVI (Diglycylallylamine)

Compound X from step (d) of Example 4 was reacted with a 1.2 fold excess of allylamine acetate in a 50:50 mixture of DMF/H$_2$O. The solution was maintained at pH 8 by the addition of triethylamine and the reaction was carried out for 4 hours at room temperature. The solution was dried under vacuum and the mixture was triturated with H$_2$O to remove triethylamine salts. The slurry was filtered, washed with cold H$_2$O, lyophilized and dried resulting in Compound XVI (c) Preparation of Compound XVII [(2,3,3 Trimethyl-3-H-indol-5yl) Acetamido Diglycylallylamine]

20.6 g of Compound XV prepared in Example 7 were dissolved in 100 ml of DMF followed by addition of 20 g of N-hydroxysuccinimide under stirring. A mixture of 22 g of dicyclohexyl carbodiimide dissolved in 30 ml of DMF was then added. The mixture was left at room temperature overnight and the next day, urea was removed by filtration. 30 g of Compound XVI from step (a) was dissolved in 100 ml of 50:50 mixture of ethanol and 1M LiOH in H$_2$O to liberate the amine. This solution was neutralized with acetic acid to pH 8 and added to the filtrate above. An equivalent amount of triethanolamine was slowly added to the solution over a 1 hour period. The mixture was left at room temperature overnight and the resultant precipitate was filtered and extracted with 500 ml of chloroform to produce Compound XVII.

(d) Preparation of Compound XVIII [(2,3,3 Trimethyl-3-H-indol-5yl) Acetamido Diglycylallylamido Ethylammonium Iodide]

Chloroform was removed from Compound XVII by vacuum. The glassy residue was dissolved in 200 ml of DMF followed by removal of the DMF by vacuum. The residue was mixed with 150 ml dichlorobenzene and 100 ml ethyliodide and refluxed at 16 hour at 100° C. After cooling, the solvent was removed by decantation. The glassy residue was triturated with ether to produce Compound XVIII.

(e) Preparation of Cyanine dyes and Cyanine Dye Labeled Nucleotides

Compound XVIII was used without any further purification to synthesize the cyanine dyes as described in Examples 1 and 2. The structure of a Cy 3 analogue made with Compound XVIII is given below.

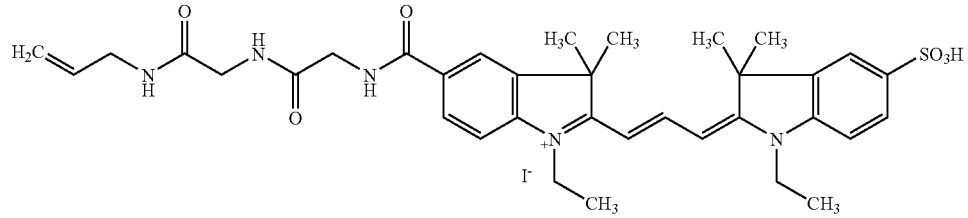

The presence of the terminal alkene bond allowed labeling of dUTP as described in Example 3. When tested in a conventional cDNA synthesis assay, significantly higher incorporation was seen with dUTP labeled with Compound XVIII as compared to a commercially available Cy-3 labeled dUTP (Cat. No. PA 530220) from Amersham Biosciences Corp., Piscataway, N.J.

Example 7 meta-EthD, with and without DNA a) Synthesis of meta-EthD

Figure 9:
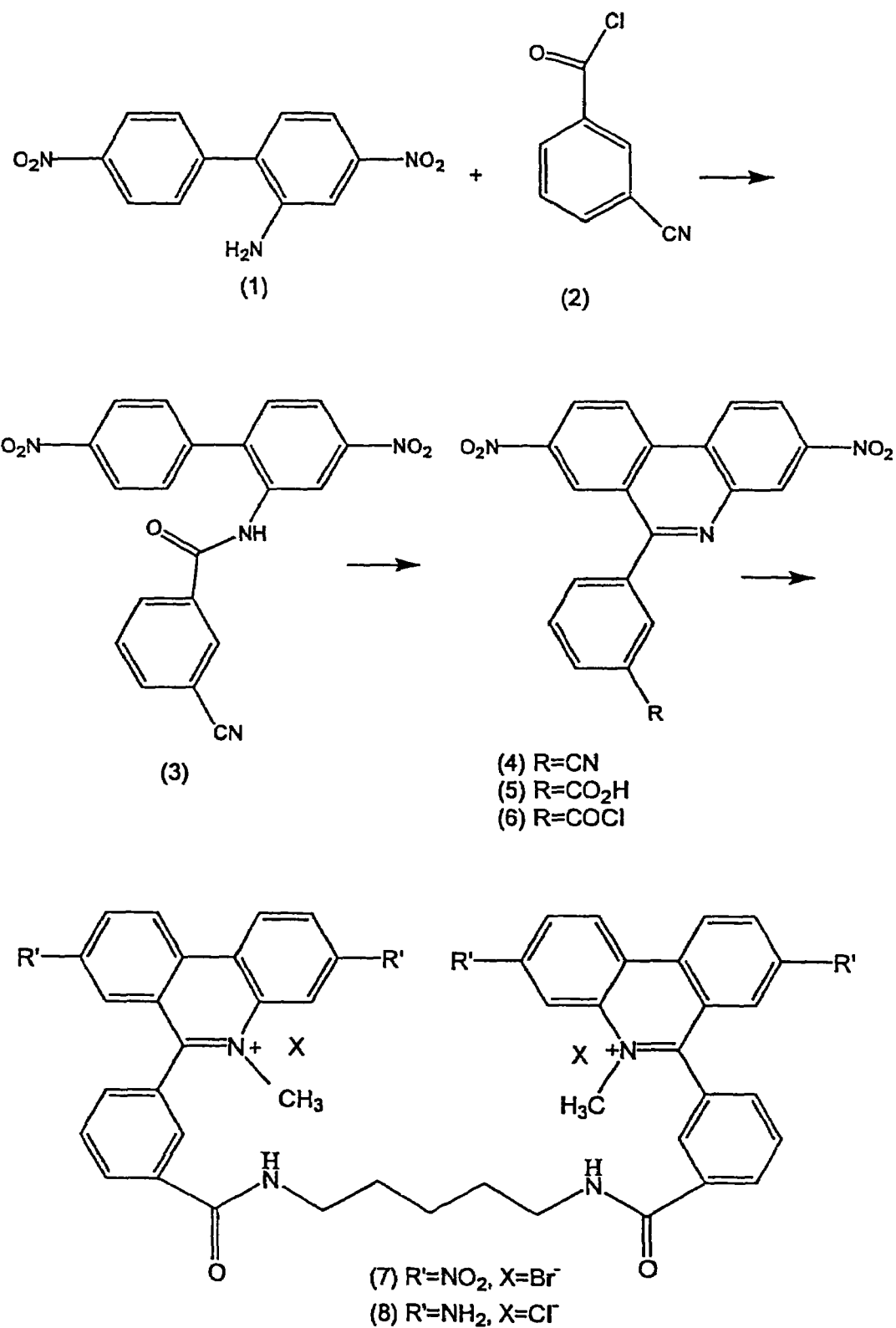
FIG. 9 is an outline of method for synthesizing a homodimer.
Figure 10:
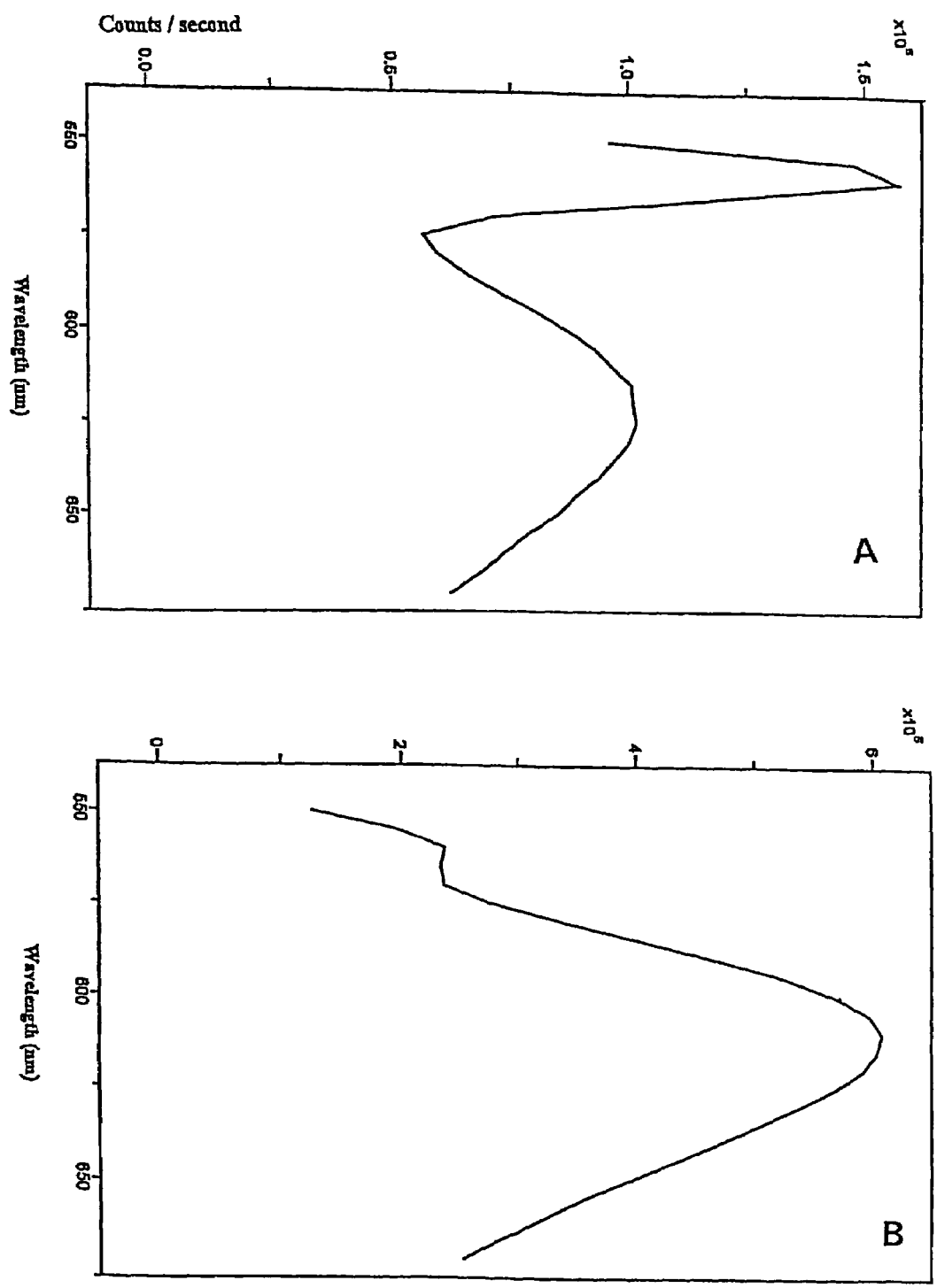
FIG. 10 depicts the results of illuminating meta-EtBr at 493 nm in the presence and absence of DNA.
Figure 11:
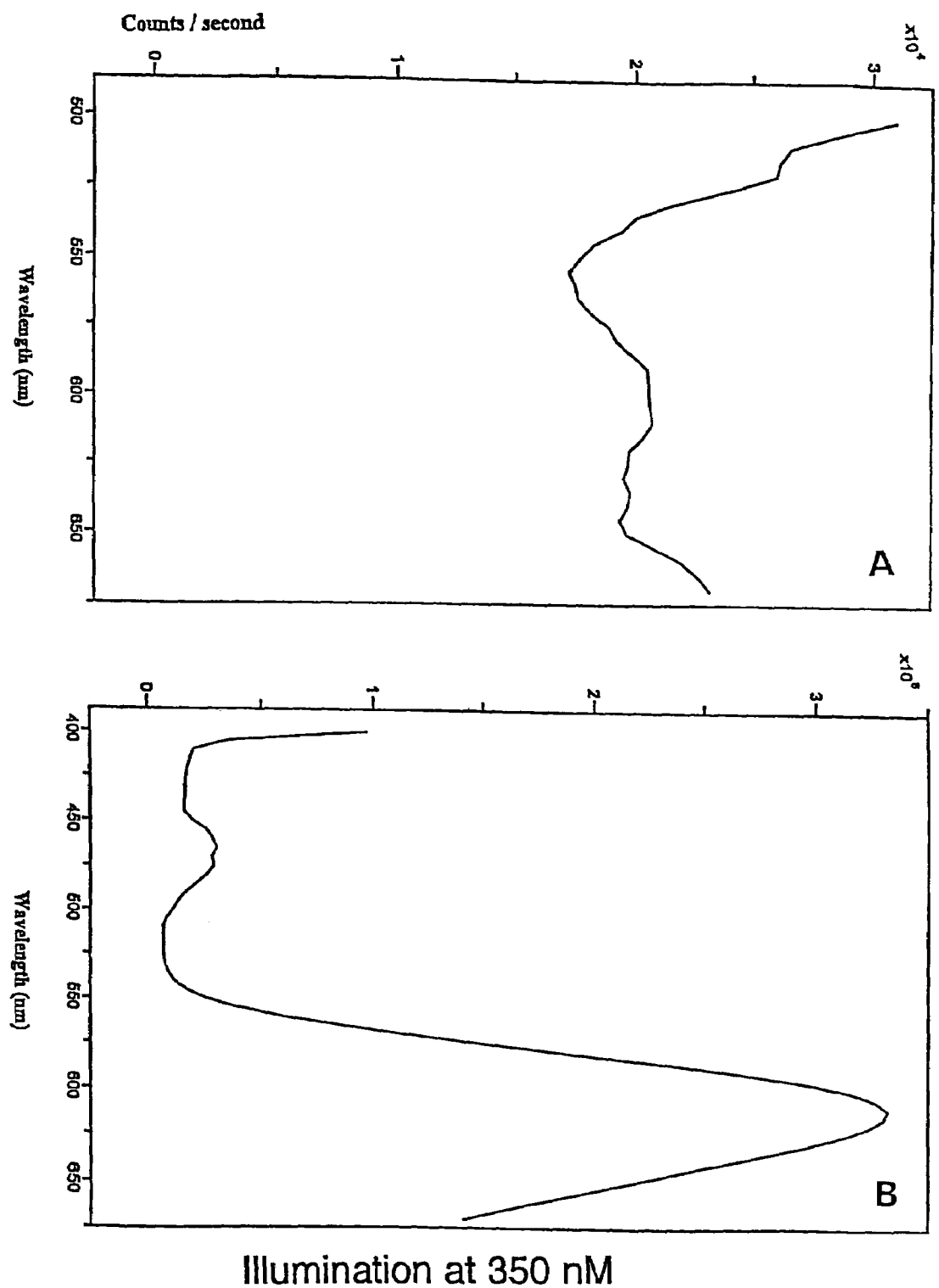
FIG. 11 shows the results of Illuminating meta-EtBr at 350 nm in the presence and absence of DNA.

The synthesis of meta-EthD was carried out according to the method described by Kuhlmann et al., supra. A diagram of the synthetic steps is given in FIG. 9. In this procedure, the 2-amino-diphenyl-compound (1) was condensed with acid chloride (2) to give the amide (3) which was then converted to a cyclic form to give the phenanthridine (4). This compound (4) was hydrolyzed to give the acid (5), converted to the acid chloride (6) and then condensed with 1,5-diamino-pentane to give the homodimer. The homodimer was methylated to give (7) which was reduced to give the final product (8) meta-EthD whose structure is given in FIG. 2.

b) Spectral Analysis meta-EthD was excited at 493 nm and gave emission of $1\times10^5$ counts/second at 617 nm (FIG. 10A). When double stranded DNA was added, the emission increased to $6\times10^5$ (FIG. 10B). In contrast, when excited at a wavelength of 350 nm, the emission at 600 nm was $2\times10^4$ counts/second that increased to approximately $3.25\times10^6$ counts/second upon the addition of DNA (FIG. 11).

Example 8

Energy Transfer Between a Donor Nucleotide and an Acceptor Nucleotide

Figure 12:
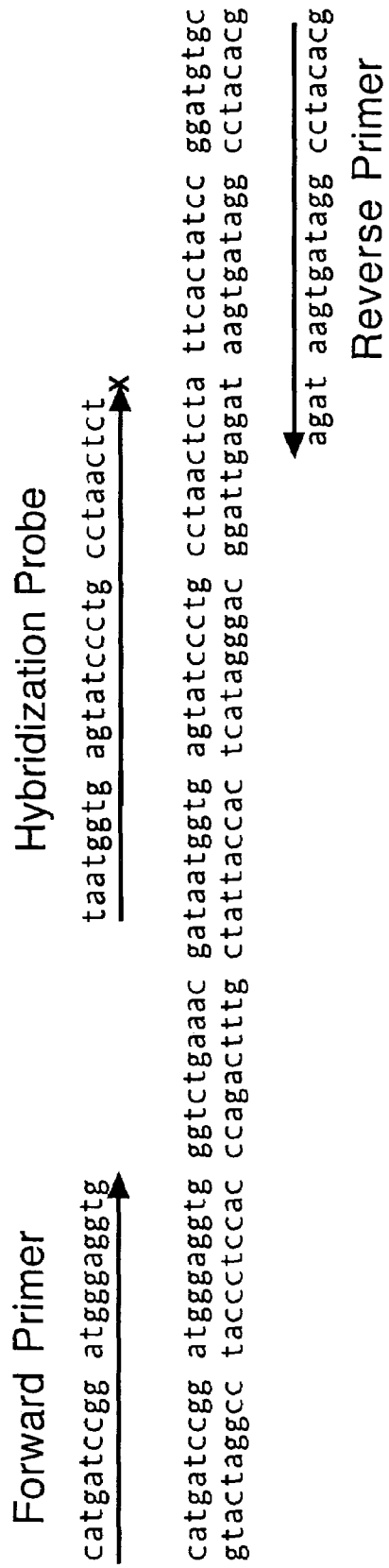
FIG. 12 shows the sequence of an HIV antisense amplicon (SEQ ID NO: 8) and sequences of two primers (SEQ ID NOS 6 & 9) and one probe (SEQ ID NO: 7) used in the examples below to illustrate the novel use of energy transfer in the present invention.

The sequence of an amplicon that can be made from an HIV antisense construct is given in FIG. 12. A description of the derivation of this construct is given in Liu et al., (1997) J. Virol 71; 4079-4085. PCR of target analytes in a sample can be carried out in the presence of a mixture of dUTP labeled with fluorescein as an energy donor and dUTP labeled with Compound XIII from Example 4 as an energy acceptor using the primers shown in FIG. 12. During the course of amplification, nucleic acid strands are synthesized that incorporate each of these labels. Illumination at a wavelength appropriate for fluorescein. followed by detection at a wavelength appropriate for the emission of Compound XIII should result in signal generation whenever donor nucleotides and acceptor nucleotides are in sufficient proximity. Either single strands or double strands could be analyzed for this purpose.

Example 9

Energy Transfer Between an Intercalator and an Incorporated Dye

PCR is carried out using the same primers as used in Example 8. However, in this example, the reaction is carried out in the presence of SYBR Green and a labeled dUTP from Example 7. As incorporation proceeds, double-stranded DNA begins to accumulate that has Compound XVIII labeled nucleotides incorporated. As described previously, SYBR Green displays enhanced fluorescence after binding to double-stranded DNA. Since SYBR Green maximally emits at 521 nm and Compound XVIII maximally absorbs at 550 nm, fluorescence from Compound XVIII should increase as synthesis proceeds due to energy transfer form SYBR green donors to Compound XVIII as an acceptor thus indicating successful amplification of target sequences.

Example 10

Energy Transfer Between an Intercalator and an Incorporated Dye with Primers that Comprise Quencher Moieties This example is carried out as describe in Example 9 except that the primers are labeled with quenchers as follows:

5' CAU*GATCCGGAU*GGGAGGTG 3' (SEQ ID NO:1) and

5' GCACAU*CCGGAU*AGU*AGA 3' (SEQ ID NO:2)

where U* are uridine moieties modifed with a non-fluorescent 3-amino xanthene as described by Singer and Haugland in U.S. Pat. No. 6,323,337 that absorb at about 530 nm. PCR is carried out with these primers in the presence of a labeled dUTP from Example 7 and SYBR Green as described above. Fluorescence from the intercalated SYBR Green can be absorbed either by Compound XVIII or by the quencher. If Primer-dimers are formed, these comprise only primers and their complements. As such energy transfer should most efficiently take place with the quenchers and thereby reduce spurious signal generation from primer-dimer synthesis. On the other hand, amplicons derived from amplfication of target sequences have segments where only compound XVIII is in sufficient proximity to the SYBR for energy transfer to take place and target dependent signals are generated as synthesis proceeds.

Example 11

Energy Transfer Between a Probe and an Incorporated Nucleotide

PCR can be carried out with the same primers used in Example 8. In this reaction mixture, potential donors are supplied in the form of dUTP labeled with Compound XVIII form Example 7. The reaction mixture also contains a DNA probe labeled with Texas Red moieties that can act as energy acceptors. The probe has the sequence

5' U$^F$AATGGU$^F$GAGTATCCCU$^F$GCCTAACTCU$^F$ 3' (SEQ ID NO:3)

where $U^F$ indicates a Uridine labeled with Texas Red. The position of this probe in the amplicon is shown in FIG. 12. The probe is also blocked at the 3' end such that it is incapable of being extended. As amplification is carried out, hybridization of the probe to labeled amplicon strands allow energy transfer to take place between Compound XVIII and Texas Red that should increase as more amplicon strands are generated.

Example 12

Endonuclease Digestion and Strand Extension Using a Homopolymeric Target as a Substrate The steps in this example are shown in FIG. 13. A CNAC with three segments can be synthesized that has the sequence:

5' -UUUUUUUUUUTTTTQQQQQQQQ-3' (SEQ ID NO:4)

where U is a uridine ribonucleotide, T is a thymidine deoxyribonucleotide and Q is an inosine ribonucleotide and the 3' end has been modifed to prevent extension. In this example, the ribonuicleotides are 2'-O-methyl as described by Shibahara et al., (1987) Nucl. Acids Res.15; 4403-4415 and Baranov et al., (1997) Nucl. Acids Res. 25; 2266-2273 (both of which are incorporated by reference). The CNAC can be hybridized to a library of poly A mRNA (step A) forming:

a first complex with the oligo-uridine first segment bound to a portion of the poly A tail, a second complex with the oligo-thymidine second segment bound to a second portion of the poly A tail; and a third complex with the oligo-inosine third segment bound to a third portion of the poly A tails.

In this example, the first and third complexes will be resistant to the actions of RNase H and the second complex should form a substrate for RNAse activity since four deoxyribonucleotides are known to be sufficient. Digestion with RNase H at 20-25° C. (step B) should induce cleavage in the poly A segment bound to the oligoT's in the second complex and release of the cleaved poly A tail. Provision of dATP, dCTP and Reverse transcriptase allows extension of the 3' end of the mRNA (step C). Additionally, if these reagents are present during the RNase H digestion step they may help stabilize the binding of the CNAC to the 3' end after endonucleolytic cleavage as described previously. It should be noted that although the inosine is capable of binding to the poly A segment, when it is used as a template, it preferentially incorporates cytosine thereby introducing a new oligo-C segment into the end of the mRNA. Removal of the CNAC allows the oligo-C segment to be used as primer binding site for an oligonucleotide containing a complementary oligo-G segment and an RNA promoter sequence. Synthesis of a cDNA strand, production of a second cDNA strand and generation of a labeled library can then be carried out by any method described previously including U.S. Pat. No. 5,891,636 and Rabbani et al. in U.S. patent application Ser. No. 09/896,897 filed Jun. 30,2001.

Example 13

Addition of an RNA Polymerase Sequence to an Analyte

This example is carried out as described in Example 12 except that the third segment of the CNAC comprises unmodified ribonucleotides and contains the sequence for an RNA promoter. As such, after strand extension in step (c), a new third complex is formed where the extended nucleotides are deoxyribonucleotides and the CNAC third segment comprises ribonucleotide. This is a substrate for RNase H digestion which can then be used to generate a single-stranded segment at the 3' end of the mRNA that is complementary to the RNA promoter sequence. A primer with promoter sequence can then be hybridized to the extended segment of the mRNA to synthesize a cDNA with a promoter at the 5' end. Subsequent events can be carried out as described in Example 12. The remaining portion of the CNAC can be removed prior to binding of the primer or extension of the primer can allow a strand displacement event.

Example 14

Figure 14:
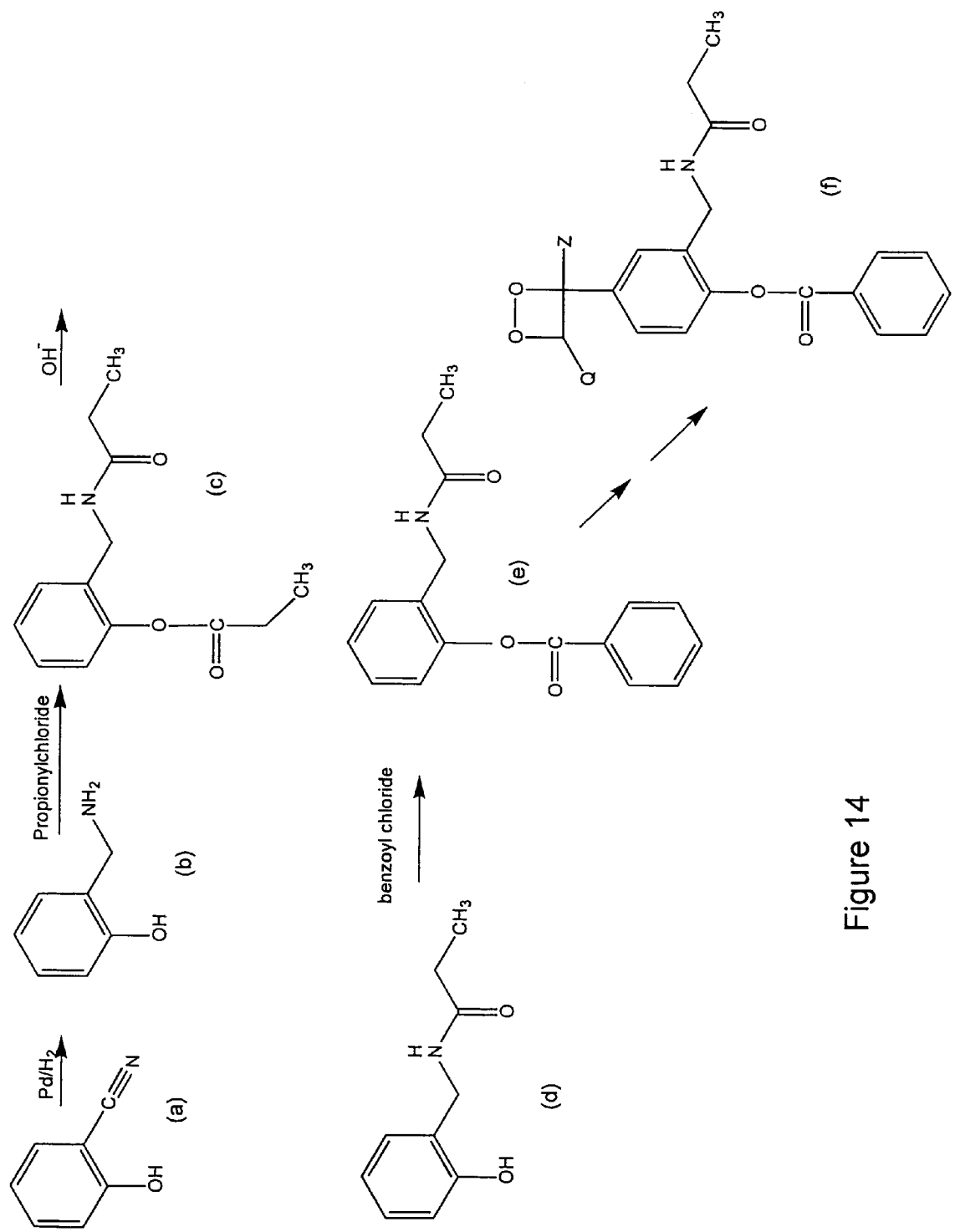
FIG. 14 shows various steps for the synthesis of a dioxetane derivative.

Preparation of a Dioxetane Derivative that is Capable of Light Generation After an Enzyme Catalyzed Intrachain Rearrangement A schematic of the steps that can be used to synthesize an intermediate compound for derivatization of a dioxetane is shown in FIG. 14. The series of steps shown in this schematic can be carried out using standard chemistry methods. In the last step of this procedure, compound (e) can be attached to a dioxetane derivative where both "Q" and "Z" are as described previously. This dioxetane derivative (f) comprises an R1 and an R2 group joined to adjacent sites of a cyclic ring as disclosed and defined in the present invention.

Example 15

Potential Series of Enzyme Dependent Events with Compound (f) from Example 14

Figure 15:
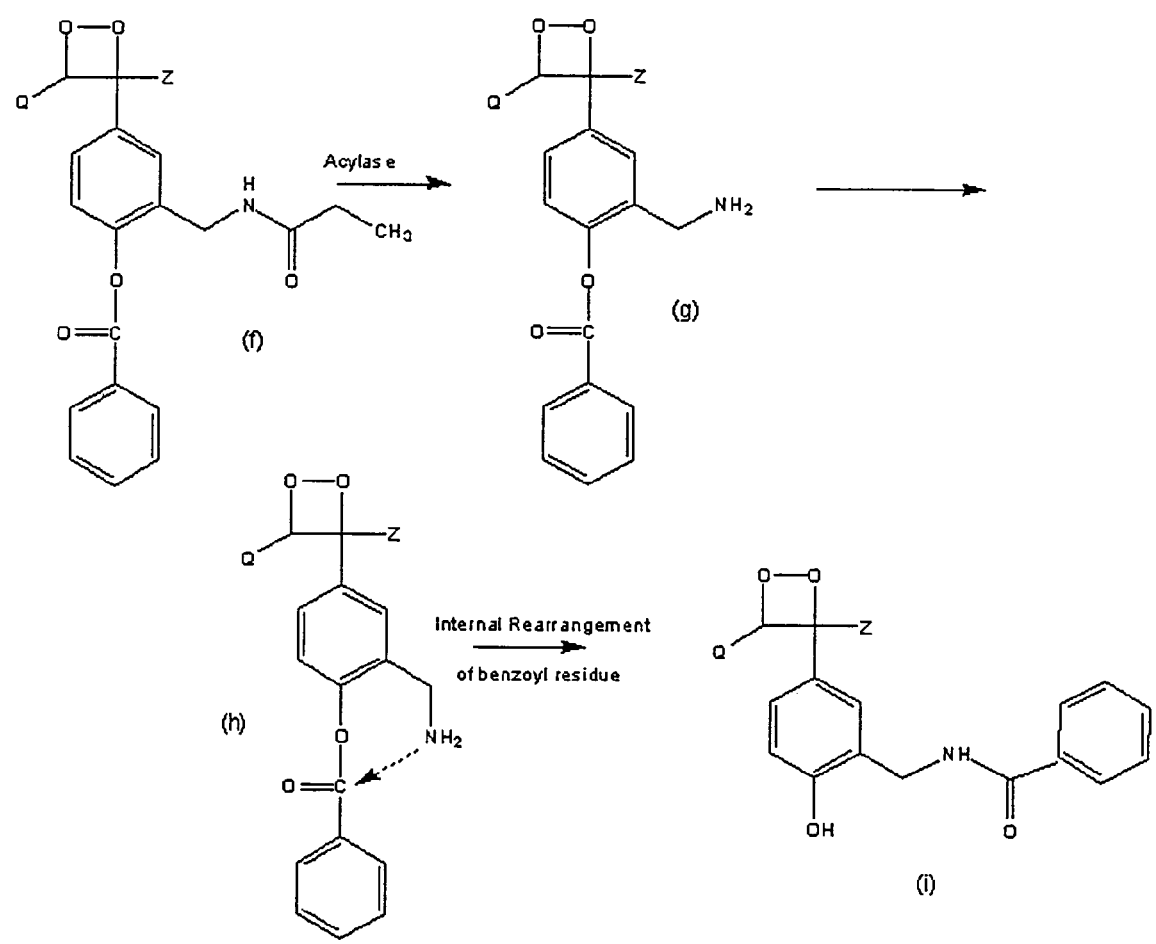
FIG. 15 shows the enzymatic production of an unstable light emitting form of a dioxetane.

In the presence of Acylase I, a cleavage event takes place that generates a free primary amine as shown by compound (f) being converted to compound (g) in FIG. 15. Due to the proximity of the released primary amine to the benzoyl residue in compound (g) and subsequent formation of a six-membered ring in the transition state, compound (h), the internal rearrangement to produce compound (i) is a very rapid reaction. The presence of the phenoxy group in compound (i) makes it an unstable dioxetane that should generate light as it decomposes. It has been previously described in the literature that a similar displacement can take place with an acyl residue and a primary amine or thiol at the end of a chain attached to the acyl group. These previously described reactions should not have the favorable kinetics of the reaction shown in this example.

This example shows an enzymatic reaction that converts R1 into R1* thereby producing a reactive group G1 that is at the end of a chain attached to one site of a cyclic ring. In this particular example, Acylase I is the enzyme and G1 is a free primary amine. The reaction continues with G1 interacting with a benzoyl group (G2) that is attached to a different site on the cyclic ring. This intermediate is shown as (h) in FIG. 15. An internal rearrangement takes place between the amine and benzoyl group (G1 and G2 respectively) leading to the intrachain transfer of the benzoyl group and generation of an unstable light emitting dioxetane.

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A labeling reagent comprising an aphenylic analog of a rhodamine dye, said analog comprising at least one reactive group for attaching said labeling reagent to a target, said at least one reactive group being attached directly to said analog or indirectly through a linker arm.

2. The labeling reagent of claim 1, said reagent having the structure

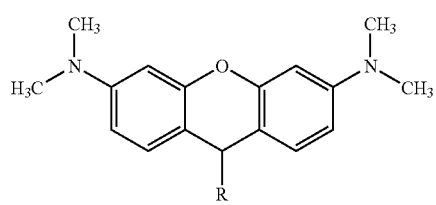

wherein R is a reactive group for attaching said labeling reagent to a target, and wherein R is attached directly or indirectly through an aphenylic linker arm.

3. The labeling reagent of claim 1, said reagent having the structure

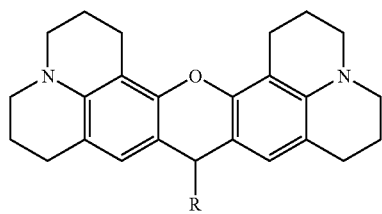

wherein R is a reactive group for attaching said labeling reagent to a target, and wherein R is attached directly or indirectly through an aphenylic linker arm.

4. The labeling reagent of claim 1, 2 or 3, wherein said reactive group comprises sulfhydryl, hydroxyl, amine, isothiocyanate, isocyanate, monochlorotriazine, dichlorotriazine, mono- or di-halogen substituted pyridine, mono- or di-halogen substituted diazine, maleimide, aziridine, sulfonylhalide, acid halide, hydroxysuccinimide ester, hydroxysulfosuccinimide ester, imidoester, hydrazine, azidonitrophenyl, azide, 3-(2-pyridyl dithio)-proprionamide, glyoxal or aldehyde.

5. The labeling reagent of claim 1, 2 or 3, wherein said reactive group is capable of forming a carbon-carbon linkage with a target.

6. The labeling reagent of claim 5, wherein said reactive group comprises an alkene group, an alkyne group, a halogenated compound or a metallo-organic compound.

7. The labeling reagent of claim 6, wherein said metallo-organic compound comprises mercury, zinc, copper or platinum.

8. The labeling reagent of claim 6, wherein said metallo-organic compound comprises an alkene group or an alkyne group.

9. The labeling reagent of claim 1, wherein said aphenylic linker arm has a backbone comprising one or more carbon atoms.

10. The labeling reagent of claim 1, wherein said aphenylic linker arm has a backbone comprising at least one non-carbon atom.

11. A labeled nucleotide comprising an aphenylic analog of a rhodamine dye, wherein said dye is attached directly to said nucleotide or indirectly through a linker.

12. The labeled nucleotide of claim 11, said labeled nucleotide having the structure:

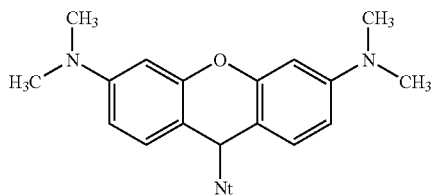

wherein Nt comprises a nucleotide.

13. The labeled nucleotide of claim 11, said labeled nucleotide having the structure:

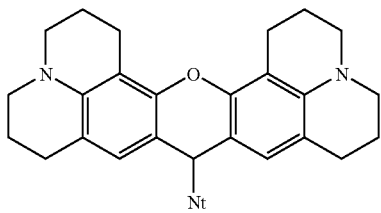

wherein Nt comprises a nucleotide.

14. The labeled nucleotide of claims 11, 12 or 13, wherein said nucleotide comprises a mono-phosphate, a di-phosphate or a tri-phosphate.

15. The labeled nucleotide of claims 11, 12 or 13, wherein said linker arm has a backbone comprising one or more carbon atoms.

16. The labeled nucleotide of claims 11, 12 or 13, wherein said linker arm has a backbone comprising at least one non-carbon atom.

17. The labeled nucleotide of claims 11, 12 or 13, wherein said linker arm comprises two or more consecutive peptide bonds.

* * * * *